United States Patent
Whitsett et al.

(10) Patent No.: US 9,370,555 B2
(45) Date of Patent: *Jun. 21, 2016

(54) SURFACTANT PROTEIN D FOR THE TREATMENT OF DISORDERS ASSOCIATED WITH LUNG INJURY

(71) Applicant: Children's Hospital Medical Center, Cincinnati, OH (US)

(72) Inventors: Jeffrey A. Whitsett, Cincinnati, OH (US); Machiko Ikegami, Cincinnati, OH (US)

(73) Assignee: CHILDREN'S HOSPITAL MEDICAL CENTER, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 14/572,421

(22) Filed: Dec. 16, 2014

(65) Prior Publication Data

US 2015/0182599 A1 Jul. 2, 2015

Related U.S. Application Data

(63) Continuation of application No. 13/021,629, filed on Feb. 4, 2011, now Pat. No. 8,933,032, which is a continuation-in-part of application No. 10/000,978, filed on Oct. 31, 2001, now abandoned, which is a continuation-in-part of application No. 09/558,576, filed on Apr. 26, 2000, now Pat. No. 6,838,428, which is a continuation-in-part of application No. PCT/US99/24675, filed on Oct. 20, 1999, said application No. 13/021,629 is a continuation-in-part of application No. 12/111,900, filed on Apr. 29, 2008, now abandoned, which is a continuation of application No. PCT/US2006/043055, filed on Nov. 3, 2006, said application No. 13/021,629 is a continuation-in-part of application No. 10/000,978, filed on Oct. 31, 2001, now abandoned.

(60) Provisional application No. 60/104,941, filed on Oct. 20, 1998, provisional application No. 60/734,017, filed on Nov. 3, 2005, provisional application No. 60/296,541, filed on Jun. 6, 2001.

(51) Int. Cl.
| | |
|---|---|
| A61K 35/42 | (2015.01) |
| C07K 14/785 | (2006.01) |
| A61K 9/12 | (2006.01) |
| A61K 38/17 | (2006.01) |

(52) U.S. Cl.
CPC ............ *A61K 38/395* (2013.01); *A61K 9/12* (2013.01); *A61K 38/17* (2013.01); *C07K 14/785* (2013.01)

(58) Field of Classification Search
CPC ........................ A61K 9/12; A61K 38/17
See application file for complete search history.

(56) References Cited

U.S. PATENT DOCUMENTS

| | | | |
|---|---|---|---|
| 3,561,444 | A | 2/1971 | Boucher |
| 3,703,173 | A | 11/1972 | Dixon |
| 4,624,251 | A | 11/1986 | Miller |
| 4,635,627 | A | 1/1987 | Gam |
| 5,670,328 | A | 9/1997 | Inoue et al. |
| 6,013,619 | A | 1/2000 | Cochrane et al. |
| 6,046,158 | A | 4/2000 | Ariizumi et al. |
| 6,136,295 | A | 10/2000 | Edwards et al. |
| 6,180,142 | B1 | 1/2001 | Taeusch |
| 6,211,162 | B1 | 4/2001 | Dale et al. |
| 6,838,428 | B2 | 1/2005 | Whitsett |
| 6,921,527 | B2 | 7/2005 | Platz et al. |
| 2003/0172389 | A1 | 9/2003 | Whitsett |
| 2003/0221199 | A1 | 11/2003 | Whitsett |
| 2004/0037781 | A1 | 2/2004 | McCormack, Jr. |

FOREIGN PATENT DOCUMENTS

| | | |
|---|---|---|
| WO | WO 86/06959 | 12/1986 |
| WO | WO 91/00871 | 1/1991 |
| WO | WO 94/23582 | 10/1994 |
| WO | WO 98/46245 | 10/1998 |
| WO | WO 00/12078 A | 3/2000 |
| WO | WO 00/23569 | 4/2000 |
| WO | WO 03/035679 | 5/2003 |
| WO | WO 2006/128025 | 11/2006 |

OTHER PUBLICATIONS

Adamson, et al. 1974. The type 2 cell as progenitor of epithelial regeneration. A cytodynamic study in mice after exposure to oxygen. *Lab Invest.* 30(1):35-42.

Aderibigbe, et al., 1999. Brief exposure to 95% oxygen alters surfactant protein D and mRNA in adult rat alveolar and bronchiolar epithelium. *Am J Respir Cell Mol Biol.* 20(2):219-227.

Akeson, et al., 2000. Embryonic vasculogenesis by endothelial precursor cells derived from lung mesenchyme. *Dev Dyn.* 217(1):11-23.

Angus, et al., 2001. Epidemiology of severe sepsis in the United States: analysis of incidence, outcome, and associated costs of care. *Crit Care Med.* 29(7):1303-1310.

Ardekani, et al., 1998. Two repressor inhibit expression of the von Willebrand factor gene promoter in vitro. *Thromb Haemost.* 80(3):488-494.

Awasthi, et al. 1999 Surfactant proteins A and D in premature baboons with chronic lung injury (Bronchopulmonary dysplasia). Evidence for an inhibition of secretion. *Am J Respir Crit Care Med.* 160(3):942-949.

(Continued)

*Primary Examiner* — Marsha Tsay
(74) *Attorney, Agent, or Firm* — Knobbe, Martens, Olson & Bear LLP

(57) ABSTRACT

Surfactant protein D (SP-D) is a 43-kDa member of the collectin family of collagenous lectin domain-containing proteins that is expressed in epithelial cells of the lung. Described herein are methods and compositions for the treatment of disorders associated with lung injury, including methods and compositions for the treatment of bronchopulmonary disorder (BPD) using recombinant human surfactant protein D and surfactant formulations.

21 Claims, 37 Drawing Sheets

(56) References Cited

OTHER PUBLICATIONS

Bachurski, et al. 2003. Nuclear factor I/thyroid transcription factor 1 interactions modulate surfactant protein C transcription. *Mol. Cell. Biol.* 23:9014-9024.

Besnard et al., 2005. Stage-specific regulation of respiratory epithelial cell differentiation by Foxa1. *Am. J. Physiol.* 289:L750-L759.

Bland et al., 1989. Lung fluid balance in lambs before and after premature birth. *J Clin Invest*, 84(2):568-576.

Bohinski, et al., 1994. The lung-specific surfactant protein B gene promoter is a target for thyroid transcription factor 1 and hepatocyte nuclear factor 3, indicating common factors for organ-specific gene expression along the foregut axis. *Mol. Cell. Biol.* 14:5671-5681.

Bone, 1996. Why sepsis trials fail. *Jama.* 276(7):565-566.

Borron et al. 1998. Recombinant rat surfactant-associated protein D inhibits human T lymphocyte proliferation and IL-2 production. *The Journal of Immunology*, 161:4599-4603.

Borthwick, et al., 2001. Evidence for stem-cell niches in the tracheal epithelium. *Am J Respir Cell Mol Biol.* 24(6):662-670.

Botas, et al. 1998. Altered surfactant homeostatis and alveolar type II cell morphology in mice lacking surfactant protein D. *Proc. Natl. Acad. Sci. USA*, 95(20):11869-11874.

Brodie, et al. 2000. Occurrence of neosocomial bloodstream infections in six neonatal intensive care units. *Pediatr Infect Dis J.* 19(1):56-65.

Brody, et al., 2000. Ciliogenesis and left-right axis defects in forkhead factor HFH-4-null mice. *Am. J. Respir. Cell. Mol. Biol.* 23:45-51.

Bruno, et al., 1995. Lung cell-specific expression of the murine surfactant protein A (SP-A) gene is mediated by interactions between the SP-A promoter and thyroid transcription factor-1. *J. Biol. Chem.* 270:6531-6536. Erratum in: *J. Biol. Chem.* 1995 270(12):, 16482.

Cao, et al., 2004. IL-4 induces production of the lung collectin surfactant protein-D. *J Allergy Clin Immunol.* 113(3):439-444.

Chen, et al., 1998. Mutation of the mouse hepatocyte nuclear factor/forkhead homologue 4 gene results in an absence of cilia and random left-right asymmetry. *J. Clin. Invest.* 102:1077-1082.

Chen, et al., 2002. NKX-3.1 interacts with prostate-derived Ets factor and regulates the activity of the PSA promoter. *Cancer Res.* 62:338-340.

Cieslik, et al., 1998. Transcriptional regulation of endothelial nitric-oxide synthase by lysophosphatidylcholine. *J Biol Chem.* 273(24):14885-14890.

Clark, et al. 1995 Targeted disruption of the surfactant protein B gene disrupts surfactant homeostasis, causing respiratory failure in newborn mice, Proc Natl Acad Sci U S A. 92(17):7794-8.

Clark, et al. 2002 Surfactant protein D reduces alveolar macrophage apoptosis in vivo. *J Immunol.* 169(6):2892-2899.

Clark, et al. 2002. Structural requirements for SP-D function in vitro and in vivo: therapeutic potential of recombinant SP-D. *Immunobiology.* 205(4-5):619-631.

Clark, et al., 2003. The potential of recombinant surfactant protein-D therapy to reduce inflammation in neonatal chronic lung disease, cystic fibrosis, and emphysema. *Arch Dis Child.* 88(11):981-984.

Costa, et al., 2001. Transcription factors in mouse lung development and function. *Am J Physiol Lung Cell Mol Physiol.* 280(5):L823-L838.

Crouch, et al., 1991. Developmental expression of pulmonary surfactant protein D (SP-D). *Am J Respir Cell Mol Biol.* 5(1):13-18.

Crouch, et al., 1992. Surfactant protein D: subcellular localization in nonciliated bronchiolar epithelial cells. *Am J Physiol.* 263(1 Pt 1):L60-L66.

Crouch, et al., 1993. Genomic organization of human surfactant protein D (SP-D). *The Journal of Biological Chemistry*, 268(4):2976-2983.

Crouch, 1998. Collectins and pulmonary host defense, *Am J Resp Cell and Mol Bio*, 19:177-201.

Crouch; 1998.Structure, biologic properties, and expression of surfactant protein D (SP-D). *Biochim Biophys Acta.* 1408(2-3):278-289.

Crouch, 2000 Surfactant protein-D and pulmonary host defense. *Respir. Res.*, 1:93-108.

Crouch, et al. 2001 Surfactant proteins A and D and pulmonary host defense. *Annu Rev Physiol.* 63:521-554.

Davé, et al., 2004. Nuclear factor of activated T cells regulates transcription of the surfactant protein D gene (Sftpd) via direct interation with thyroid transcription factor-1 in lung epithelial cells. *J Biol Chem.* 279(33):34578-34588.

deFelice, et all., 2003. TTF-1 phosphorylation is required for peripheral lung morphogenesis, perinatal survival, and tissue-specific gene expression. *J. Biol. Chem.* 278:35574-35583.

Demayo, et al. 2002. Mesenchymal-epithelial interactions in lung development and repair: are modeling and remodeling the same process? *Am J Physiol Lung Cell Mol Physiol.* 283:L510-L517.

Dempsey et al., 2005. Outcome of neonates less than 30 weeks gestation with histologic chorioamnionitis. *Am J Perinatol*, 22(3):155-159.

Dong, et al., 1998. Degradation of surfactant protein D by alveolar macrophages. *Am J Physiol.* 274(1 Pt 1):L97-105.

Eggleton, et al. 1999. Lung surfactant proteins involved in innate immunity. *Current Opinion in Immunology*, 11(1):28-33.

Endo, et al., 2002. Surfactant protein A and D (SP-A, AP-D) levels in patients with septic ARDS. *Res Commun Mol Pathol Pharmacol.* 111(5-6):245-251.

Erpenbeck, et al., 2005. Surfactant protein D increases phagocytosis and aggregation of pollen-allergen starch granules. *Am J Physiol Lung Cell Mol Physiol.* 288(4):L692-698.

Fisher, et al., 1995. Expression of pulmonary surfactant protein D in rat gastric mucosa. *Am J Respir Cell Mol Biol.* 12(1):13-18.

Fisher, et al., 2000. Pulmonary-specific expression of SP-D corrects pulmonary lipid accumulation of SP-D gene-targeted mice. *Am. J. Physiol. Lung Cell. Mol. Physiol.*, 278(2):L365-L373.

Ford, et al., 1992. Basal cells are the progenitors of primary tracheal epithelial cell cultures. *Exp Cell Res.* 198(1):69-77.

French, et al., 1996. The influence of formulation on emission, deaggregation and deposition of dry powders for inhalation. *J Aerosol Science* 27(5):769-783.

Fujita, et al. 2005. Serum surfactant protein D is increased in acute and chronic inflammation in mice. *Cytokine* 31(1):25-33.

Gardai, et al., 2003. By binding SIRPalpha or calreticulin/CD91, lung collectins act as dual function surveillance molecules to suppress or enhance inflammation. *Cell.* 115(1):13-23.

Glauser, et al., 1991. Septic shock: pathogenesis. *Lancet.* 3388(8769):732-736.

Gonda, 1990. Aerosols for delivery of therapeutic and diagnostic agents to the respiratory tract. *Crit Rev Ther Drug Carrier Syst.* 6(4):273-313.

Gotoh, et al., 1997. The glucocorticoid-responsive gene cascade. Activation of the rat arginase gene through induction of C/EBPbeta. *J Biol Chem.* 272(6):3694-3698.

Grandel, et al., 2003. Endothelial responses to bacterial toxins in sepsis. *Crit Rev Immunol.* 23(4):267-299.

Greene, et al., 1999. Serial changes in surfactant-associated proteins in lung and serum before and after onset of ARDS. *Am J Respir Crit Care Med.* 160(6):1843-1850.

Greene, et al., 2002. Serum surfactant proteins-A and -D as biomarkers in idiopathic pulmonary fibrosis. *Eur Respir J.* 19(3):439-446.

Guazzi, et al., 1990. Thyroid nuclear factor 1 (TTF-1) contains a homeodomain and displays a novel DNA binding specificity. *EMBO J.* 9:3631-3639.

Haczku, et al., 2004. Surfactant protein D and asthma. *Clin Exp Allergy.* 34(12):1815-1818.

Hansen, et al., 2006. Surfactant protein D augments bacterial association but attenuates major histocompatibility complex class II presentation of bacterial antigens. *Am J Respir Cell Mol Biol.* 36(1):94-102.

Hartl, et al., 2006. Surfactant protein D in human lung diseases. *Eur J Clin Invest.* 36(6):423-435.

Hartshorn, et al., 1994. Evidence for a protective role of pulmonary surfactant protein S (SP-D) against influenza A virus. *J Clin Invest.*, 94(1):311-319.

(56) References Cited

OTHER PUBLICATIONS

Hartshorn, et al. 1996. Interactions of recombinant human pulmonary surfactant protein D and SP-D multimers with influenza A. *Am J Physiol Lung Cell Mol Physiol.* 271:L753-L762.
Hartshorn, et al. 1998. Pulmonary surfactant proteins A and D enhance neutrophil uptake of bacteria. *Am J Physiol.* 274(6 Pt 1):L958-L969.
Hartshorn, et al. 2000. Enhanced anti-influenza activity of a surfactant protein D and serum conglutinin fusion protein. *American Journal of Physiology*, 278(1):L90-L98.
Hawgood, et al. 2001. The pulmonary collectins and surfactant metabolism. *Annu Rev Physiol.* 63:495-519.
He, et al., 2000. Proximal promoter of the surfactant protein D gene: regulatory roles of AP-1, forkhead box, and GT box binding proteins. *J Biol Chem.* 275(40):31051-31060.
Herbein, et al., 2000. Binding and uptake of surfactant protein D by freshly isolated rat alveolar type II cells. *Am J Physiol Lung Cell Mol Physiol.* 278(4):L830-L839.
Hickling, et al. 1999. A recombinant trimeric surfactant protein D carbohydrate recognition domain inhibits respiratory syncytial virus infection in vitro and in vivo. *European Journal of Immunology*, 29(11):3478-3484.
Hokuto, et al., 2004. Stat-3 is required for pulmonary homeostasis during hyperoxia. *J Clin Invest.* 113(1):28-37.
Holt, et al. 2002. Interactions between RSV infection, asthma, and atopy: Unraveling the complexities. *J Exp Med* 196(10): 1271-1275.
Honda, et al. 1995. Pulmonary surfactant protein D in sera and bronchoalveolar lavage fluids. *Am J Respir Crit Care Med.* 152(6 Pt 1):1860-1866.
Hong et al., 20001. Clara cell secretory protein-expressing cells of the airway neuroepithelial body microenvironment include a label-retaining subset and are critical for epithelial renewal after progenitor cell depletion. *Am J Respir Cell Mol Biol.* 24(6):671-681.
Ikegami, et al., 1980. The quantity of natural surfactant necessary to prevent the respiratory distress syndrome in premature lambs. *Pediatr Res.* 14(9):1082-1085.
Ikegami, et al., 1981. Phospholipid composition of fetal lung fluid and amniotic fluid during late gestation in sheep. *Am J Obstet Gynecol.* 141(2):227-229.
Ikegami, et al., 1993. Surfactant metabolism. *Semin Perinatol.* 17(4):233-240.
Ikegami, et al., 2000. Surfactant metabolism in SP-D gene-targeted mice. *Am J Physiol Lung Cell Mol Physiol.* 279(3):L468-L476.
Ikegami, et al., 2004. Initial responses to ventilation of premature lambs exposed to intra-amniotic endotoxin 4 days before delivery. *Am J Physiol Lung Cell Mol Physiol.* 286(3):L573-L579.
Ikegami, et al., 2006. Intratracheal recombinant surfactant protein D prevents endotoxin shock in the newborn preterm lamb. *Am J Resp Crit Care Med.* 173(12):1342-1347.
Jackson; 2001. Airway goblet-cell mucus secretion. *Trends Pharmacol. Sci.* 22:39-45.
Jain-Vora, et al., 1997. Interleukin-4 alters epithelial cell differentiation and surfactant homeostasis in the postnatal mouse lung. *Am. J. Respir. Cell. Mol. Biol.* 17:541-551.
Jain-Vora, et al. 1998. Interleukin-4 enhances pulmonary clearance of pseudomonas aeruginosa, *Infection and Immunity*, 66(9):4229-4236.
Jiang et al., 2004. Neonatal sepsis in the neonatal intensive care unit: characteristics of early versus late onset. *J Microbiol Immunol Infect.* 37(5):301-306.
Jobe et al., 1985. Lung protein leaks in ventilated lambs: effects of gestational age. *J Appl Physiol.* 58(4):1246-1251.
Jobe, et al., 1996. Surfactant effects on aerosolized and instilled adenoviral-mediated gene transfer. *Hum Gene Ther.* 7(6):697-704.
Jobe, et al. 1997. Surfactant for the treatment of respiratory distress syndrome. *Am. Rev. Respir. Dis.* 136:1256-1275.
Johansson, et al. 1994. The protein of the surfactant system. *Eur. Respir. J.*, 7:372-391.
Kamachi, et al., 2000. Pairing SOX off: with partners in the regulation of embryonic development. *Trends Genet.*, 16(4):182-187.

Kanai, et al., 1996. Identification of two Sox17 messenger RNA isoforms, with and without the high mobility group box region, and their differential expression in mouse spermatogenesis. *J Cell Biol.* 133(3):667-681.
Kanai-Azuma, et al., 2002. Depletion of definitive gut endoderm in *Sox17*-null mutant mice. *Development* 129(10):2367-2379.
Karim, et al., 1990. The ETS-domain: a new DNA-binding motif that recognizes a purine-rich core DNA sequence. *Genes Dev.* 4(9):1451-1453.
Kasper, et al., 2002. Increased surfactant protein D in rat airway goblet and Clara cells during ovalbumin-induced allergic airway inflammation. *Clin Exp Allergy.* 32(8):1251-1258.
Katoh; 2002. Molecular cloning and characterization of human *SOX17. Int J Mol Med.* 9:153-157.
Katoh; 2002. Expression of human SOX7 in normal tissues and tumors. Int J Mol Med. 9:363-368.
Kaufman, et al., 2004. Clinical microbiology of bacterial and fungal sepsis in very-low-birth-weight infants. *Clin Microbiol Rev*, 17(3):638-680.
Kaza, et al., 2002. Keratinocyte growth factor enhances post-pneumonectomy lung growth by alveolar proliferation. *Circulation* 106(12 Suppl 1):I120-124.
Kelly, et al., 1996. Transcription of the lung-specific surfactant protein C gene is mediated by thyroid transcription factor 1. *J. Biol. Chem.* 271(12):6881-6888.
Khoor, et al., 1993. Developmental expression of SP-A and SP-A mRNA in the proximal and distal respiratory epithelium in the human fetus and newborn. *J. Histochem. Cytochem.* 41(9):1311-1319.
Kimura, et al., 1996. The *T/ebp* null mouse: thyroid-specific enhancer-binding protein is essential for the organogenesis of the thyroid, lung, ventral forebrain, and pituitary. *Genes Dev.* 10(1):60-69.
Kingma, et al., 2006. Correction of pulmonary abnormalities in Sftpd-/-mice requires the collagenous domain of surfactant protein D. *J Biol Chem.* 281(34):24496-24505.
Kishore, et al. 1996. The $\alpha$-helical neck region of human lung surfactant protein D is essential for the binding of the carbohydrate recognition domains to lipopolysaccharides and phospholipids. *Biochem J.* 318(Pt 2):505-511.
Kitamura, et al., 2003. Study of surfactant protein D (SP-D) in spetic ards: report of three cases. *Critical care and shock, Indonesian Society of Critical Care Medicine.* 6(2):114-117.
Korfhagen, et al. 1996. Altered surfactant function and structure in SP-A gene targeted mice. *Proc. Natl. Acad. Sci. USA*, 93:9594-9599.
Korfhagen, et al. 1998. Surfactant protein-D regulates surfactant phospholipid homeostatis in vivo. *The Journal of Biological Chemistry*, 273(43):28438-28443.
Kou, R. et al., 2005. Differential regulation of vascular endothelial growth factor receptors (VEGFR) revealed by RNA interference: interactions of VEGFR-1 and VEGFR-2 in endothelial cell signaling. *Biochemistry.* 44(45):15064-15073.
Kramer, et al., 2001. Surfactant protein A recruits neutrophils into the lungs of ventilated preterm lambs. *Am J Respir Crit Care Med.* 163(1):158-165.
Kramer, et al., 2002. Intratracheal endotoxin causes systemic inflammation in ventilated preterm lambs. *Am J Respir Crit Care Med.* 165(4):463-469.
Kramer, et al. 2001. Exogenous surfactant changes the phenotype of alveolar macrophages in mice. *Am J Physiol Lung Cell Mol Physiol.* 280(4):L689-L694.
Krause, et al. 2001. Multi-organ, multi-lineage engraftment by a single bone marrow-derived stem cell. *Cell*, 105(3):369-377.
Kuan, et al., 1991. Interactions of surfactant protein-D with *Escherichia coli. J Cell Biol.* 115(3 Pt 2):236A.
Kuan, et al. 1992. Interactions of surfactant protein D with bacterial lipopolysaccharides. *J. Clin. Invst. The American Society for Clinical Investigation Inc.* 90:97-106.
Kuperman, et al., 2002. Direct effects of interleukin-13 on epithelial cells cause airway hyperreactivity and mucus overproduction in asthma. *Nat. Med.* 8:885-889.
Kuroki, et al., 1998. Surfactant proteins A and D: disease markers. *Biochim Biophys Acta.* 1408(2-3):334-345.

(56) References Cited

OTHER PUBLICATIONS

Laros, et al., 1987. Dilatation, compensatory growth, or both after pneumonectomy during childhood and adolescence. A thirty-year follow-up study. *J Thorac Cardiovasc Surg.* 93(4):570-576.
Lawson, et al., 1999. Genomic organization of the mouse gene for lung surfactant protein D. *Am J Respir Cell Mol Biol.* 20(5):953-963.
Lecuona, et al., 1999. Ventilator-associated lung injury decreases lung ability to clear edema and downregulates alveolar epithelial cell Na,K-adenosine triphosphatase function. *Chest.* 116(1 Suppl):29S-30S.
Leth-Larsen, et al., 2004. Surfactant protein D in the female genital tract. *Mol Hum Reprod.* 10(3):149-154.
Leuwerke, et al., 2002. Inhibition of compensatory lung growth in endothelial nitric oxide synthase-deficient mice. *Am J Physiol Lung Cell Mol Physiol* 282(6):L1272-1278.
LeVine, et al. 1997. Surfactant protein A-deficient mice are susceptible to group B streptococcal infection. *J Immunol.* 158(9): 4336-4340.
LeVine, et al., 1998. Surfactant protein-A-deficient mice are susceptible to Pseudomonas aeruginosa infection. *Am J Respir Cell Mol Biol.* 19(4):700-708.
LeVine, et al., 1999. Surfactant protein-A binds group B *Streptococcus* enhancing phagocytosis and clearance from lungs of surfactant protein-A-deficient mice. *Am J Respir Cell Mol Biol.* 20:279-286.
LeVine, et al., 1999. Surfactant protein-A enhances respiratory syncytial virus clearance in vivo. *J Clin Invest.* 103(7):1015-1021.
LeVine, et al., 2000. Distinct effects of surfactant protein A or D deficiency during bacterial infection on the lung. *J Immunol.* 165(7):3934-3940.
LeVine, et al., 2001. Pulmonary collectins and innate host defense of the lung. *Microbes and Infection*, 3:161-166.
LeVine, et al., 2001. Surfactant protein D enhances clearance of influenza A virus from the lung in vivo. J Immunol, 167(10):5868-5873.
LeVine, et al., 2004. Surfactant protein-D enhances phagocytosis and pulmonary clearance of respiratory syncytial virus. *Am J Respir Cell Mol Biol*, 31(2):193-199.
Li, et al., 1998. Cloning of the amino-terminal and 5'-flanking region of the human MUC5AC mucin gene and trancriptional up-regulation by bacterial exoproducts. *J. Biol. Chem.* 273(12):6812-6820.
Li, et al., 2002. Microbial infection and inflammation in the development of chronic lung disease of prematurity. *Microbes Infect.* 4(7):723-732.
Lim, et al., 1994. Expression of the carbohydrate recognition domain of lung surfactant protein D and demonstration of its binding to lipopolysaccharides of gram-negative bacteria. *Biochem Biophys Res Commun.* 202(3):1674-1680.
Lin, et al., 2006. Erm/thyroid transcription factor 1 interactions modulate surfactant protein C transcription. *J. Biol. Chem.* 281(24):16716-16726.
Liu, et al., 2002. GATA-6 is required for maturation of the lung in late gestation. *Am. J. Physiol.* 283(2):L468-L475.
Liu, et al., 2002. GATA-6 and thyroid transcription factor-1 directly interact and regulate surfactant protein-C gene expression. *J. Biol. Chem.* 277(6):4519-4525.
Liu, et al., 2003. Role for ETS domain transcription factors Pea3/Erm in mouse lung development. *Dev. Biol.* 261(1):10-24.
Liu, et al., 2005. Therapeutic effect of surfactant protein D in allergic inflammation of mite-sensitized mice. *Clin Exp Allergy.* 35(4):515-521.
Lu, et al. 1992. Purification, characterization and cDNA cloning of human lung surfactant protein D. *Biochem. J.*, 284:795-802.
Mahvi, et al. 1977. Morphology of a naphthalene-induced bronchiolar lesion. *Am J Pathol.* 86(3):558-572.
Mason, et al. 1998. Surfactant protein A and surfactant protein D in health and disease. Invited Review. *The American Physiological Society*, L1-L13.
McCormack; 1995. Molecular biology of the surfactant apoproteins. *Seminars Resp Crit Care Med.* 16(1):29-38.
McIntosh, et al., 1996. Surfactant proteins A and D increase in response to intratracheal lipopolysaccharide. *Am J Respir Cell Mol Biol.* 15(4):509-519.
McKenzie, et al., 1999. Impaired development of Th2 cells in IL-13-deficient mice. *Immunity* 9:423-432.
Miyamura, et al. 1994. Surfactant proteins A (SP-A) and D (SP-D): levels in human amniotic fluid and localization in the fetal membranes. *Biochim Biophys Acta.* 1210(3):303-307.
Motwani, et al., 1995. Mouse surfactant protein-D. cDNA clongin, characterization, and gene localization to chromosome 14. *J Immunol.* 155(12):5671-5677.
Mucenski, et al., 2003. β-Catenin is required for specification of proximal/distal cell fate during lung morphogenesis. *J Biol Chem.*, 41(10):40231-40238.
Mucenski, et al., 2005. β-Catenin regulates differentiation of respiratory epithelial cells in vivo. *Am. J. Physiol.* 289:L971-L979.
Mulligan, 1991. The basic science of gene therapy. *Science*, 260:926-932.
Mullis, et al., 1986. Specific enzymatic amplification of DNA in vitro: the polymerase chain reaction. *Cold Spring Harb Symp Quant Biol.* 51(1):263-273.
Murakami, et al., 2002. Surfactant protein A inhibits peptidoglycan-induced tumor necrosis factor-alpha secretion in U937 and alveolar macrophages by direct interaction with toll-like receptor 2. *J Biol Chem.* 277(9):6830-6837.
Murphy, et al., 1998. Molecular biology of septic shock. *New Horiz.* 6(2):181-193.
Nadel, et al. 2001. The role of epidermal growth factor in mucus production. *Curr. Opin. Pharmacol.* 1:254-258.
Naik, et al., 2001. Effects of ventilation with different positive end-expiratory pressures on cytokine expression in the preterm lamb lung. *Am J Respir Crit Care Med.* 164(3):494-498.
Nakajima, et al., 1998 Longitudinal follow-up of pulmonary function after lobectomy in childhood—factors affecting lung growth. *Pediatr Surg Int.* 13(5-6):341-345.
Naltner, et al., 2000. Retinoic acid stimulation of the human surfactant protein B promoter is thyroid transcription factor 1 site-dependent. *J. Biol. Chem.* (275(1):56-62.
Newman, Therapeutic aerosols—The inhaled route for respiratory drugs. *Aerosols and the lung*, Ed. Clarke, et al. 9:196-224.
Ni, et al., 2005. Surfactant protein D is present in human tear fluid and the cornea and inhibits epithelial cell invasion by Pseudomonas aeruginosa. *Infect Immun.* 73(4):2147-2156.
Noah, et al. 2003. Bronchoalveolar lavage fluid surfactant protein-A and surfactant protein-D are inversely related to inflammation in early cystic fibrosis. *Am J Respir Crit Care Med.* 168(6):685-691.
Oberley, et al., 2004. Surfactant protein D is present in the human female reproductive tract and inhibits Chlamydia trachomatis infection. *Mol Hum Reprod.* 10(12):861-870.
Oettgen, et al., 2000. PDEF, a novel prostate epithelium-specific ets transcription factor, interacts with the androgen receptor and activates prostate-specific antigen gene expression. *J. Biol. Chem.* 275:1216-1225.
Ohya, et al., 2006. Human pulmonary surfactant protein D binds the extracellular domains of Toll-like receptors 2 and 4 . . . *Biochemistry*, 45(28):8657-8664.
Okubo, et al., 2004 Hyperactive Wnt signaling changes the developmental potential of embryonic lung endoderm. *J Biol.* 3(3):11-28.
Ortiz, et al., 2003. Mesenchymal stem cell engraftment in lung is enhanced in response to bleomycin exposure and ameliorates its fibrotic effects.
Otake, et al. 1998. Nonspecific inflammation inhibits adenovirus-mediated pulmonary gene transfer and expression independent of specific acquired immune responses. *Hum Gene Ther.* 9(15):2207-2222.
Park, et al., 2004. TAZ interacts with TTF-1 and regulates expression of surfactant protein-C. *J. Biol. Chem.* 279(17):17384-17390.
Park, et al. 2004. Sox17 regulates differentiation of progenitor cells in the airway epithelium in the lung. *Develop Biol.* 271(2):582 (Abstract 167).
Park, et al., 2006. Sox17 influences the differentiation of respiratory epithelial cells. *Dev. Biol.* 294:192-202.

(56) References Cited

OTHER PUBLICATIONS

Pendergrast, et al., 2005. Nucleic acid aptamers for target validation and therapeutic applications. *J Biomol Tech.* 16(3):224-234.
Perl, et al., 2002. Conditional gene expression in the respiratory epithelium of the mouse. *Transgenic Res.* 11(1):21-29.
Perl, et al., 2002. Early restriction of peripheral and proximal cell lineages during formation of the lung. *Proc Natl Acad Sci USA.* 99(16):10482-10487.
Perl, et al.., 2005. Conditional recombination reveals distinct subsets of epithelial cells in trachea, bronchi, and alveoli. *Am. J. Respir. Cell. Mol. Biol.* 33:455-462.
Pikaar, et al., 1995. Opsonic activities of surfactant proteins A and D in phagocytosis of gram-negative bacteria by alveolar macrophages. *J Infect Dis.* 172(2):481-489.
Postle, et al. 1999. Deficient hydrophilic lung surfactant proteins A and D with normal surfactant phospholipid molecular species in cystic fibrosis. *Am J Respir Cell Mol Biol.* 20(1):90-98.
Pringle, 1986. Human fetal lung development and related animal models. *Clin Obstet Gynecol*, 29:502-513.
Rankin, et al., 1996. Phenotypic and physiologic characterization of transgenic mice expressing interleukin 4 in the lung: lymphocytic and eosinophilic inflammation without airway hyperreactivity. *Proc. Natl. Acad. Sci. USA.* 93(15):7821-7825.
Ray, et al., 1996. Transcriptional regulation of a mouse Clara cell-specific protein (mCC10) gene by the NKx transcription factor family members thyroid transcription factor 1 and cardiac muscle-specific homeobox protein (CSX). *Mol. Cell. Biol.* 16(5):2056-2064.
Reading, et al. 1998. Antiviral activity of bovine collectins against rotaviruses. *Journal of General Virology*, 79:2255-2263.
Reid; 1998. Interactions of surfactant protein D with pathogens, allergens and phagocytes. *Biochimica et Biophysica Acta*, 1408(2-3):290-295.
Reid; 1998. Functional roles of the lung surfactant proteins SP-A and SP-D in innate immunity. *Immunobiol.*, 199:200-207.
Reynolds, et al., 2000. Neuroepithelial bodies of pulmonary airways serve as a reservoir of progenitor cells capable of epithelial regeneration. *Am J Pathol.*, 156(1):269-278.
Rice, et al., 2002. Maintenance of the mouse type II cell phenotype in vitro. *Am J Physiol.* 283:L256-L264.
Rogers. 2004. Airway mucus hypersecretion in asthma: an undervalued pathology? *Curr. Opin. Pharmacol.* 4(3):241-250.
Sambrook, et al., 1989. Molecular Clonging—A laboratory manual, 2nd Ed. *Cold Harbor Press, NY* (Contents Only) pp. 1-30.
Sanghavi, et al., 2002. Surfactant protein D levels are increased in tracheal lavage samples from incubated neonates with sepsis. Neonatology; *Pediatr Res.* 51(4 Pt 2):346-347A.
Sano, et al., 2000. Surfactant proteins A and D bind CD14 by different mechanisms. *J Biol Chem.* 275(29):22442-22451.
Sartori, et al., 2002. Alveolar epithelial fluid transport in acute lung injury: new insights. *Eur Respir J.* 20(5):1299-1313.
Sato, et al., 2003. Direct binding of Toll-like receptor 2 to zymosan, and zymosan-induced NF-Kappa B activation and TNF-alpha secretion are down-regulated by lung collectin surfactant protein A. *J Immunol.* 171(1): 417-425.
Schaub, et al. 2004. Surfactant protein D deficiency influences allergic immune responses. *Clin Exp Allergy.* 34(12):1819-1826.
Senft, et al., 2005. Surfactant protein-D regulates soluble CD14 through matrix metalloproteinase-12. *J Immunol.* 174(8):4953-4959.
Shannon, et al. 2004 Epithelial-mesenchymal interactions in the developing lung. *Annu Rev Physiol.* 66:625-645.
Shimizu, et al. 1992. Primary structure of rat pulmonary surfactant protein D. *The Journal of Biological Chemistry*, 267(3):1853-1857.
Singh, et al. 1996. Strategies and applications of DNA level diagnosis in genetic diseases: Past experiences and future directions. *Elsevier Science B.V., Biotechnology Annual Review*, 2:409-445.
Sinner, et al., 2004. Sox17 and β-catenin cooperate to regulate the transcription of endodermal genes. *Development*, 131(13):3069-3080.
Sorensen, et al. 2006. Surfactant protein D is proatherogenic in mice. *Am J Physiol Heart Circ Physiol.* 290(6): H2286-H2294.

Sorensen, et al. 2006. Genetic and environmental influences of surfactant protein D serum levels. *Am J Physiol Lung Cell Mol Physiol.* 290(5): L1010-L1017.
Stahlman, et al. 2002. Immunolocalization of surfactant protein-D (SP-D) in human fetal, newborn, and adult tissues. *J Histochem Cytochem.* 50(5):651-660.
Stoll, et al., 2002. Late-onset sepsis in very low birth weight neonates: the experience of the NICHD Neonatal Research Network. *Pediatrics.* 110(2 Pt 1):285-291.
Stoll, et al., 2005. Very low birth weight infants with early onset of neonatal sepsis: the predominance of gram-negative infections continues in the National Institute of Child Health and Human Devleopment Neonatal Research Network, 2002-2003. Pediatr Infect Dis J, 24(7):635-639.
Stripp, et al., 1995. Plasticity of airway cell proliferation and gene expression after acute naphthalene injury. *Am J Physiol.* 269(6 Part 1):L791-799.
Strong, et al., 1998. A novel method of purifying lung surfactant proteins A and D from the lung lavage of alveolar proteinosis patients and from pooled amniotic fluid. *J Immunol Methods.* 220(1-2):139-149.
Takash, et al., 2001. SOX7 transcription factor: sequence, chromosomal localisation, expression, transactivation and interference with Wnt signalling. *Nucleic Acids Res.*, 29(21):4274-4283.
Tokieda, et al, Pulmonary dysfunction in neonatal SP-B-deficient mice., Am J Physiol. Oct. 1997;273(4 Pt 1):L875-82.
Tomkinson, et al., 2001. Temporal association between airway hyper-responsiveness and airway eosinophilia in ovalbumin-sensitized mice. *Am. J. Respir. Crit. Care. Med.* 163(3 Pt 1):721-730.
Tryka, et al., 1986. Patterns of cell proliferation during recovery from oxygen injury. Species differences. *Am Rev Respir Dis.* 133(6):1055-1059.
van de Wetering, et al. 2004. Collectins: players of the innate immune system. *Eur J Biochem.* 271(7):1229-1249.
van Eijk, et al., 2000. Procine lung surfactant protein D: Complementary DNA cloning, chromosomal localization, and tissue distribution. *The Journal of Immunology*, 164(3):1442-1450.
van Iwaarden, et al., 1992. Rat surfactant protein D enhances the production of oxygen radicals by rat alveolar macrophages. *Biochem. J.*, 286:5-8.
van Iwaarden, et al., 1994. Binding of surfactant proein A to the lipid A moiety of bacterial lipopolysaccharides. *Biochem J*, 303 (Pt 2):407-411.
van Rozendaal, et al. 1997. Pulmonary surfactant proteins A and D are involved in the early response to intratracheally aerosolized lipopolysaccharide. *Biochem Soc Trans.* 25(4):S656.
van Rozendaal. et al. 1999. Aerosolized endotoxin is immediately bound by pulmonary surfactant protein D in vivo. *Biochim Biophys Acta.* 1454(3):261-269.
van Winkle, et al., 1995. Cellular response in naphthalene-induced Clara cell injury and bronchiolar epithelial repair in mice. *Am J Physiol.* 269(6 Part 1):L800-818.
van Winkle, et al., 1996. Repair of naphthalene-injured microdissected airways in vitro. *Am J Respir Cell Mol Biol.* 15(1):1-8.
von Bredow, et al. 2003. Proteolysis of surfactant protein D by cystic fibrosis relevant proteases. *Lung*, 181(2):79-88.
Voorhout, et al., 1992. Immunocytochemical localization of surfactant protein D (SP-D) in type II cells, Clara cells, and alveolar macrophages of rat lung. *J Histochem Cytochem.* 40(10):1589-97.
Vuk-Pavlovic, et al., 2003. Unique chemotypes of *E. coli* LPS exhibit differential interactions with lung surfactant protein-D. *Faseb J.* 17(7):C53 & Enlargement; 2 pages.
Wan, et al., 2004. Foxa2 regulates alveolarization and goblet cell hiperplasia. *Development* 131(4):953-964.
Wan, et al., 2004. Foxa2 is required for transition to air breathing at birth. *Proc. Natl. Acad. Sci. USA* 101(40):14449-14454.
Wan, et al., 2005. Compensatory roles of Foxa1 and Foxa2 during lung morphogenesis. *J. Biol. Chem.* 280(14):13809-13816.
Wang, et al., 1998. Inhibitory effect of pulmonary surfactant proteins A and D on allergen-induced lymphocyte proliferation and histamine release in children with asthma. *Am. J. Respir. Crit. Care Med.*, 158:510-518.

(56) References Cited

OTHER PUBLICATIONS

Wearley; 1991. Recent progress in protein and peptide delivery by noninvasive routes. *Crit Rev Ther Drug Carrier Syst.* 8(4):331-394.
Wegner; 1999 From head to toes: the multiple facets of Sox proteins, *Nucleic Acids Res.* 27(6):1409-1420.
Wenstrom, et al., 1998 Elevated second-trimester amniotic fluid interleukin-6 levels predict preterm delivery. *Am J Obstet Gynecol.*, 178(3):546-550.
Wert, et al., 1993. Transcriptional elements from the human SP-C gene direct expression in the primordial respiratory epithelium of transgenic mice. *Dev. Biol.* 156(2):426-443.
Wert, et al. 2000. Increased metalloproteinase activity, oxidant production, and emphysema in surfactant protein D gene-inactivated mice. *PNAS*, 97(11):5972-5977.
Wert, et al., 2002. Increased expression of thyroid transcription factor-1 (TTF-1) in respiratory epithelial cells inhibits alveolarization and causes pulmonary inflammation. *Dev. Biol.* 242(2):75-87.
Whitsett; 2005. Surfactant proteins in innate host defense of the lung. *Biol Neonate.* 88(3):175-180.
Wills-Karp, et al., 1998. Interleukin-13: central mediator of allergic asthma. *Science.* 282:2258-2261.
Wilson, et al., 2002. Matching SOX: partner proteins and co-factors of the SOX family of transcriptional regulators. *Curr Opin Genet Dev.*, 12(4):441-446.
Wright, Jo Rae, Immunomodulatory Functions of Surfactant, Physiological Reviews. Oct. 1997; vol. 77, No. 4: 1-32.
Wu, et al., 2003. Surfactant proteins A and D inhibit the growth of Gram-negative bacteria by increasing membrane permeability. *J Clin Invest.* 111(10):1589-1602.
Yamada, et al. 2000. Cloning and expression of the mouse Pse gene encoding a novel Ets family member. *Gene.* 241:267-274.
Yan, et al., 2001. Protein-protein interaction of retinoic acid receptor alpha and thyroid transcription factor-1 in respiratory epithelial cells. *J. Biol. Chem.* 276(24):21686-21691.
Yang, et al., 2002. GATA6 regulates differentiation of distal lung epithelium. *Development.* 129(9):2233-2246.
Yi, et al., 2002. Role of CBP/p300 and SRC-1 in transcriptional regulation of the pulmonary surfactant protein-A (SP-A) gene by thyroid transcription factor-1 (TTF-1). *J. Biol. Chem.* 277(4):2997-3005.
Yoshida, et al. 2001. Surfactant protein D regulates NF-kappa B and matrix metalloproteinase production in alveolar macrophages via oxidant-sensitive pathways. *Jour. Immunol.*, 166(12):7514-7519.
You, et al., 2004. Role of f-box factor foxj1 in differentiation of ciliated airway epithelial cells. *Am J Physiol.*, 286:L650-L657.
Zhang, et al., 2001. Activity of pulmonary protein-D (SP-D) in vivo is dependent on oligomeric structure. *J Biol Chem.* 276(22):19214-19219.
Zhang, et al., 2002. Reversibility of pulmonary abnormalities by conditional replacement of surfactant protein D (SP-D) in vivo. *J Biol Chem.* 277(41):38709-38713.
Zhang, et al., 2003. The β-Catenin/VegT-regulated early zygotic gene *Xnr5* is a direct target of SOX 3 regulation. *Development*, 130(23):5609-5624.
Zhou, et al., 1996. Thyroid transcription factor-1, hepatocyte nuclear factor-3beta, surfactant protein B, C, and Clara cell secretory protein in developing mouse lung. *J. Histochem. Cytochem.* 44(10):1183-1193.
Zhou, et al., 1996. Arrested lung morphogenesis in transgenic mice bearing an SP-C-TGF-beta 1 chimeric gene. *Dev Biol.* 175(2):227-238.
Zorn, et al., 1999. Regulation of Wnt signaling by Sox proteins: XSox17α/β and Xsox3 physically interact with β-Catenin. *Mol Cell.* 4(4):487-498.
Zsengeller, et al., 1998 Adenovirus-mediated granulocyte-macrophage colony-stimulating factor improves lung pathology of pulmonary alveolar proteinosis in granulocyte-macrophage colony-stimulating factor-deficient mice. *Hum Gene Ther.* 9(14):2101-2109.
International Search Report and Written Opinion from International Application No. PCT/US06/03055, dated Jul. 19, 2007.

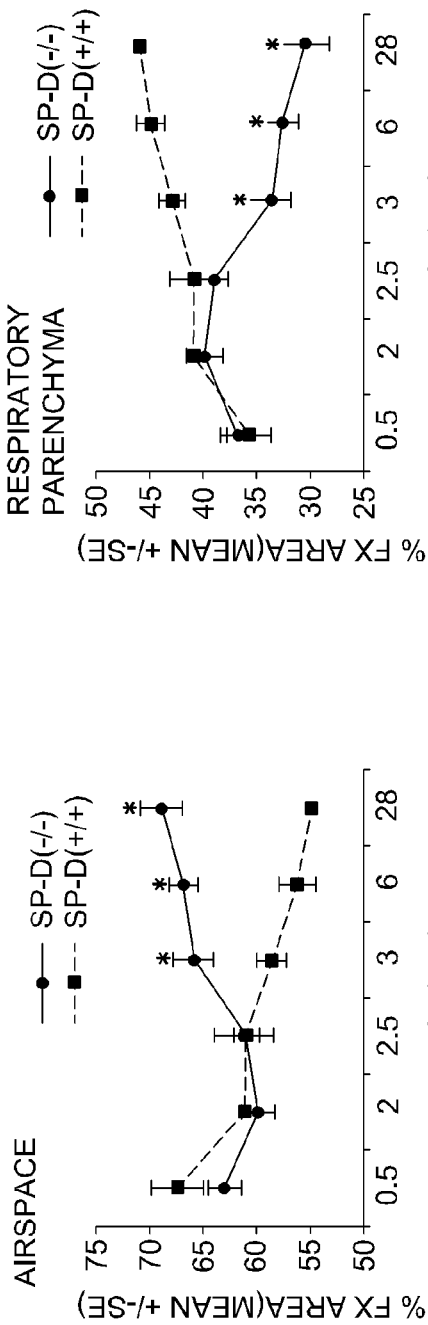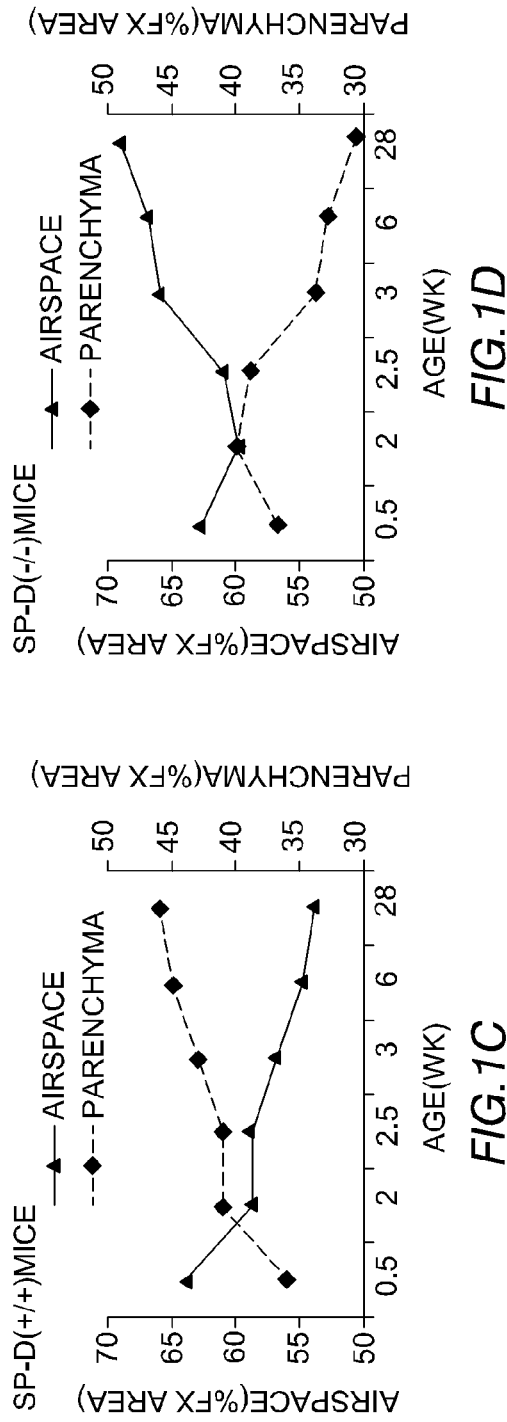

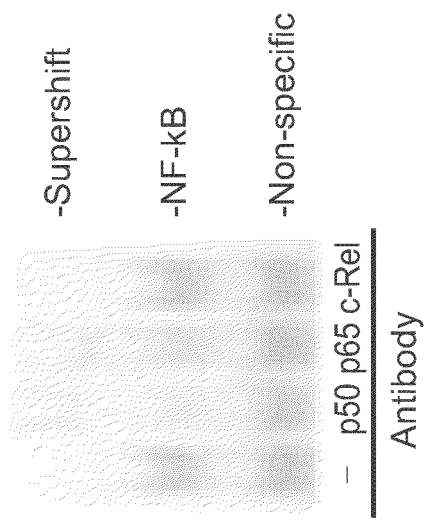
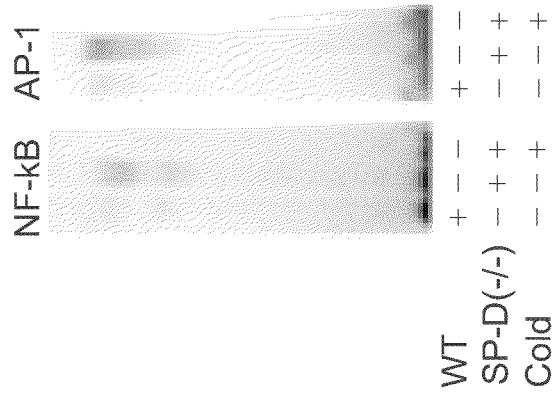
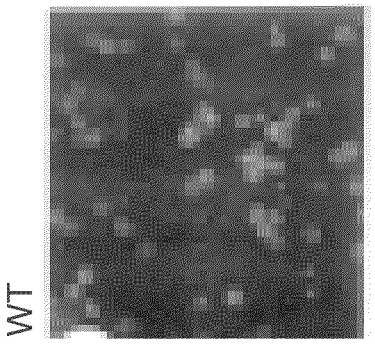

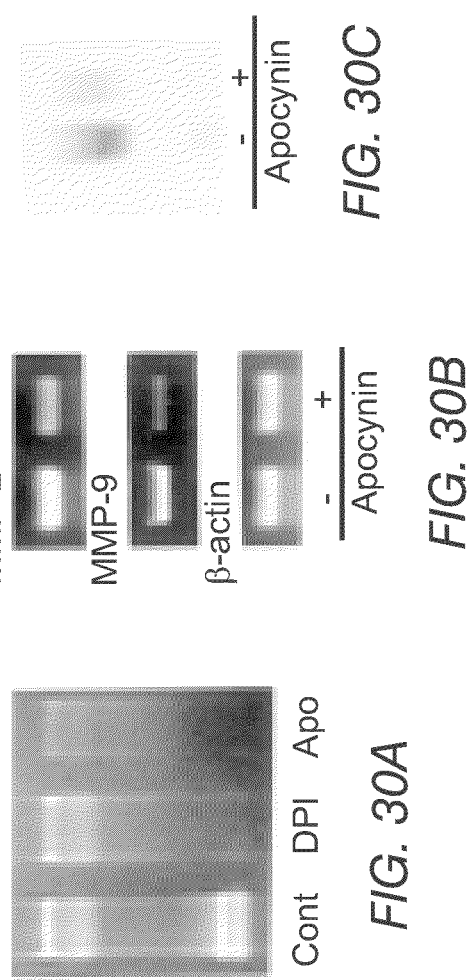

SURFACTANT PROTEIN D FOR THE TREATMENT OF DISORDERS ASSOCIATED WITH LUNG INJURY

RELATED APPLICATIONS

This application is a continuation of U.S. patent application Ser. No. 13/021,629 filed Feb. 4, 2011 which is a continuation-in-part of U.S. patent application Ser. No. 10/000,978, filed on Oct. 31, 2001, which claims priority under 35 U.S.C. 119(e) to U.S. Provisional Application No. 60/296,541, filed on Jun. 6, 2001. U.S. patent application Ser. No. 13/021,629 is a also continuation-in-part of U.S. patent application Ser. No. 09/558,576, filed on Apr. 26, 2000, now U.S. Pat. No. 6,838,428, issued Jan. 4, 2005, which is a continuation-in-part of PCT/US99/24675, filed on Oct. 20, 1999, which claims priority under 35 U.S.C. 119(e) to U.S. Provisional Application No. 60/104,941, filed on Oct. 20, 1998. U.S. patent application Ser. No. 13/021,629 is also a continuation-in-part of U.S. patent application Ser. No. 12/111,900, filed on Apr. 29, 2008, which is a continuation of PCT/US2006/043055, filed on Nov. 3, 2006, which claims priority to U.S. Provisional Application No. 60/734,017, filed Nov. 3, 2005, all of the foregoing are hereby incorporated by reference in their entireties.

STATEMENT REGARDING FEDERALLY SPONSORED R&D

This invention was made with government support under HL041320, HL056387, HL058795, HL003905, HL028623 and HL085610 awarded by the National Institutes of Health. The government has certain rights in the invention.

REFERENCE TO SEQUENCE LISTING

The present application includes a Sequence Listing in electronic format. The Sequence Listing is provided as a file entitled AIRWY001P3C1.TXT, created Feb. 9, 2015, which is approximately 4 KB in size. The information in the electronic format of the Sequence Listing is incorporated herein by reference in its entirety.

BACKGROUND OF THE INVENTION

Pulmonary surfactant is essential for normal lung mechanics and gas exchange in the lung. Pulmonary surfactant is produced by type II epithelial cells and is made up of a phospholipid component which confers the ability of surfactant to lower surface tension in the lung. In addition, there are proteins associated with the surfactant called collectins which are collagenous, lectin domain-containing polypeptides. Two of these, surfactant protein A (SP-A) and surfactant protein D (SP-D), have been postulated as being involved in surfactant structure and function and host defense. Both quantitative and qualitative deficiencies in pulmonary surfactant are associated with neonatal respiratory distress, adult respiratory distress syndrome, congenital deficiencies of surfactant protein B, and allergic asthma. In addition, deficiency in pulmonary surfactant may contribute to the increased susceptibility of some individuals to microbial challenge, especially in the setting of inadequate or impaired specific immunity. These disorders as well as some disorders associated with increased risk of pneumonia (cystic fibrosis, asthma, prematurity, chronic bronchitis, diffuse alveolar damage) may also be associated with acquired defects or deficiency in collectin function. Alveolar surfactant pools are regulated at multiple levels including intracellular synthesis, secretion, re-uptake and degradation of these components by alveolar macrophages. The synthesis and clearance of surfactant phospholipids and proteins is further influenced by developmental, mechanical, and humoral stimuli that serve to maintain steady-state surfactant concentrations after birth.

The role of the collectins in surfactant and normal lung function has been extensively investigated. The collectin family of C-type lectins includes a number of molecules with known host defense functions. SP-A and SP-D, also C-type lectins, bind influenza and herpes simplex viruses as well as gram positive and gram-negative bacteria and various fungi. By binding, they enhance uptake by alveolar macrophages and neutrophils. Various cellular binding sites for SP-A and SP-D have been identified on alveolar macrophages or, in the case of SP-A, on type II epithelial cells. The critical role of SP-A in host defense was supported by the observation that SP-A-deficient mice are susceptible to infections by group B *streptococcus, Pseudomonas aeruginosa*, respiratory syncytial virus, adenovirus, and mycoplasma in vivo. Collectins may also participate in the recognition or clearance of other complex organic materials, such as pollens and dust mite allergens.

SP-D is a 43 kilodalton protein that has been proposed to play a role in host defense in the lung. Its cDNA and gene have been sequenced in various mammals, including humans. SP-D shares considerable structural homology with other C-type lectins, including surfactant protein A (SP-A), conglutinin, bovine collectin-43, and mannose binding protein. In vitro studies and its close structural relationship to a mammalian $Ca^{2+}$-dependent lectin family (particularly shared structural motifs) support its role in host defense. SP-D is synthesized primarily and at relatively high concentrations by Type II epithelial cells and nonciliated bronchiolar epithelial cells in the lung, but may also be expressed in the gastrointestinal tract, heart, kidney, pancreas, genitourinary tract and mesentery cells. In vitro studies demonstrated that SP-D binds to the surface of organisms via its lectin domain (or sugar binding domain), which leads to binding, aggregation, opsonization and, in some instances, activation of killing by phagocytes in vitro. SP-D binds to lipopolysaccharide, various bacteria, fungi and viruses, including influenza virus. It also binds to both alveolar macrophages and polymorphonuclear cells.

In vitro studies support the concept that surfactant proteins may be important in the regulation of surfactant homeostasis. Although the hydrophobic surfactant proteins SP-B and SP-C have roles in production of the surfactant monolayer, in vitro studies indicated that surfactant protein A may also facilitate surfactant uptake and/or secretion by type II epithelial cells. In fact, it was widely believed that SP-A would have a major role in surfactant homeostasis. However, studies of SP-A null mice have not supported the primary role of surfactant protein A in surfactant secretion or re-uptake. For example, the absence of SP-A does not lead to obvious physiologic or morphologic structural abnormalities of the lung. Further, SP-A null mutant mice lack tubular myelin figures, but produce highly functional surfactant that absorbs rapidly and produces monolayers. Surfactant lipid synthesis, secretion, and re-uptake were essentially normal in SP-A null mice, and although both SP-A and SP-D have immunomodulatory properties, addition of SP-A to surfactant for treatment did not reduce lung inflammation in the ventilated premature newborn lamb (Kramer B W, et al, *Am J Respir Crit Care Med* 2001; 163:158-165).

SUMMARY OF THE INVENTION

One embodiment of the invention is a non-human mammalian model for emphysema comprising an SP-D(−/−) non-human mammal.

A further embodiment is a method for the purification and treatment of pulmonary disease by introducing mammalian SP-D protein, or vectors expressing the mammalian SP-D protein, into a human or mammal in an amount effective to reduce the symptoms of the disease or to prevent the disease.

A further embodiment is a pharmaceutical composition effective in treating pulmonary disease which is a mixture of SP-D protein with a pharmaceutically acceptable carrier.

A further embodiment is a biologically active agent for treating pulmonary disease in mammals which is an agent that up-regulates SP-D.

A further embodiment is a biologically active agent for treating pulmonary disease in mammals which is an agent that interacts with the SP-D protein.

A further embodiment is a method for diagnosing susceptibility to pulmonary disease in mammals by identifying a mutation in the SP-D gene which results in deficient SP-D, identifying that mutation in a test mammal by PCR, hybridization, or ELISA.

A further embodiment is a method of identifying pharmaceutical agents useful in treating pulmonary disease by allowing the SP-D null mouse to develop pulmonary disease, administering a pharmaceutical agent to the mammal, and identifying the agent as effective is the pulmonary disease improves.

A further embodiment is a method of purifying SP-D antibodies with a solid phase lung homogenate from any mouse which does not produce SP-D protein.

A further embodiment is a method for the prevention of pulmonary disease by introducing mammalian SP-D protein, or vectors expressing the mammalian SP-D protein into a human in an amount effective to reduce the symptoms of or prevent pulmonary disease, wherein the pulmonary disease is selected from the group consisting of: reactive oxygen-mediated disease, chemically induced lung injury, injury due to oxygen radicals, injury due to ozone, injury due to chemotherapeutic agents, inflammatory and infectious diseases, reperfusion injury, drowning, transplantation, and rejection.

A further embodiment of the invention is a method for the treatment of viral disease by introducing mammalian SP-D protein, or vectors expressing the mammalian SP-D protein into a human in an amount effective to reduce the number of viruses or symptoms of the viral disease. Preferably, the viruses are adenovirus, RSV, and influenza virus.

In some embodiments, a method for the treatment of pulmonary inflammation associated with a lung injury in a mammal in need thereof is provided, comprising introducing recombinant human surfactant protein D (rhSP-D) and a surfactant formulation to the mammal in an amount effective to reduce the pulmonary inflammation associated with the lung injury, where the surfactant formulation comprises at least one phospholipid. In certain embodiments, the lung injury is associated with a condition selected from the group consisting of oxidant injury, lung abscesses, secondary diseases, cystic fibrosis, interstitial pulmonary fibrosis (IPF), and chronic obstructive pulmonary disease (COPD), various lung infections, respiratory distress syndrome (RDS), bronchopulmonary dysplasia (BPD), chemotherapy-induced lung injury, lung fibrosis secondary to primary abscess, and asthma. In certain embodiments, the lung injury is associated with bronchopulmonary dysplasia (BPD). In certain embodiments, the surfactant formulation further comprises at least one protein selected from the group consisting of surfactant protein A (SP-A), surfactant protein B (SP-B), surfactant protein C (SP-C), and fragments and mimics thereof. In certain embodiments, the surfactant formulation further comprises a synthetic surfactant protein. In certain embodiments, the dosage of the rhSP-D is about 0.1 mg to about 10 mg per kg body weight. In certain embodiments, the composition is introduced intratracheally. In certain embodiments, the mammal is an infant.

In some embodiments, a method for reducing the risk of developing bronchopulmonary dysplasia (BPD) is provided, comprising administering recombinant human SP-D (rhSP-D) and a surfactant formulation to a mammal in an amount effective to reduce the risk of developing BPD in the mammal, where the surfactant formulation comprises at least one phospholipid. In certain embodiments, the BPD is associated with injury from mechanical ventilation. In certain embodiments, the surfactant formulation further comprises at least one protein selected from the group consisting of surfactant protein A (SP-A), surfactant protein B (SP-B), surfactant protein C (SP-C), and fragments and mimics thereof. In certain embodiments, the surfactant formulation further comprises a synthetic surfactant protein. In certain embodiments, the dosage of the rhSP-D is about 0.1 mg to about 10 mg per kg body weight. In certain embodiments, the composition is administered intratracheally. In certain embodiments, the mammal is an infant.

In some embodiments, a composition is provided, comprising recombinant human SP-D (rhSP-D); and a surfactant formulation, where the surfactant formulation comprises at least one phospholipid. In certain embodiments, the surfactant formulation further comprises at least one protein selected from the group consisting of surfactant protein A (SP-A), surfactant protein B (SP-B), surfactant protein C (SP-C), and fragments and mimics thereof. In certain embodiments, the surfactant formulation further comprises a synthetic surfactant protein. In certain embodiments, the composition is formulated for intratracheal administration. In certain embodiments, the composition is formulated for aerosol administration.

BRIEF DESCRIPTION OF THE DRAWINGS

FIGS. 1A and 1B depict a comparison of changes in fractional areas (% Fx Area) of airspace (a), and respiratory parenchyma (b) with age in SP-D (−/−) mice and age-matched SP-D (+/+) controls, respectively. FIGS. 1C and 1D depict an analysis of changes in these parameters with age for SP-D (+/+) and SP-D (−/−) mice, respectively. Data are expressed as % fractional area and represent the mean±SE.

FIGS. 28A, 28B, and 28C depict NF-κB activation in AMs from SP-D (−/−) mice. FIG. 28A depicts Immunofluorescence staining for NF-κB p65 in AMs from WT and SP-D (−/−) mice. Lavaged cells from SP-D (−/−) mice and age matched controls were prepared for immunohistochemistry. Intense staining for NF-κB was observed in the cytoplasm and nuclei of AMs from SP-D (−/−) compared to WT mice. FIG. 28B depicts EMSA for NF-κB. Nuclear extracts of AMs were obtained from WT and SP-D (−/−) mice and NF-κB activation assessed by EMSA. Enhanced DNA binding activities of NF-κB were detected in the nuclear extracts from SP-D (−/−) compared to those from WT mice. Specific competition with a excess of unlabeled NF-κB oligonucleotide eliminated the NF-κB band. Likewise AP-1 binding activities were enhanced in the nuclear extracts from SP-D (−/−) mice. FIG. 28C depicts a supershift assay which demonstrated bands containing the p50 and p65 subunit, but not c-Rel.

FIGS. 30A, 30B, and 30C depict NADPH oxidase inhibitors decrease MMP production by AMs from SP-D (−/−) mice. AMs from SP-D (−/−) mice were treated with 1 μM diphenylene iodonium chloride (DPI) and 1 mM apocynin. (FIG. 30A) Conditioned media from AMs were analyzed by SDS-PAGE zymography. DPI and apocynin markedly decreased MMP activity. (FIG. 30B) MMP-2 and 9 mRNA were detected by RT-PCR using specific primers for the cDNA sequences of MMP-2 and 9 as follows: Total RNA from macrophages was extracted by TRIzol reagent (GIBCO, BRL, Gaithersburg, Md.) according to the manufacture's protocol. Reverse transcription was carried out for 45 min at 42° C. with oligo(dT) and Moloney murine leukemia virus reverse transcriptase (GIBCO, BRL). cDNA were amplified using various primers specific for the cDNA sequences of the following molecules: MMP-2 (5'-TCT GCG GGT TCT CTG CGT CCT GTG C-3' (SEQ ID NO:1), 5'-GTG CCC TGG AAG CGG AAC GGA AAC T-3' (SEQ ID NO:2), MMP-9 (5'-TTC TCT GGA CGT CAA ATG TGG-3')(SEQ ID NO:3), 5'-CAA AGA AGG AGC CCT AGT TCA AGG-3')(SEQ ID NO:4), β-actin (5'-GTG GGC CGC TCT AGG CAC CAA-3' (SEQ ID NO:5), 5'-CTC TTT GAT GTC ACG CAG GAT TTC-3')(SEQ ID NO:6). The PCR products were electrophoresed in 1% agarose gels and stained with ethidium bromide-stained gels that were imaged using the Alpha-Imager 2000 Documentation and Analysis Software (Alpha Innotech, San Leandro, Calif.). MMP-2 and 9 mRNA were also decreased by the NADPH oxidase inhibitor. (FIG. 30C) EMSA analysis demonstrated that treatment of apocynin reduced DNA binding activity of NF-κB in AMs isolated from SP-D (−/−) mice.

DETAILED DESCRIPTION OF THE INVENTION

Figure 2:
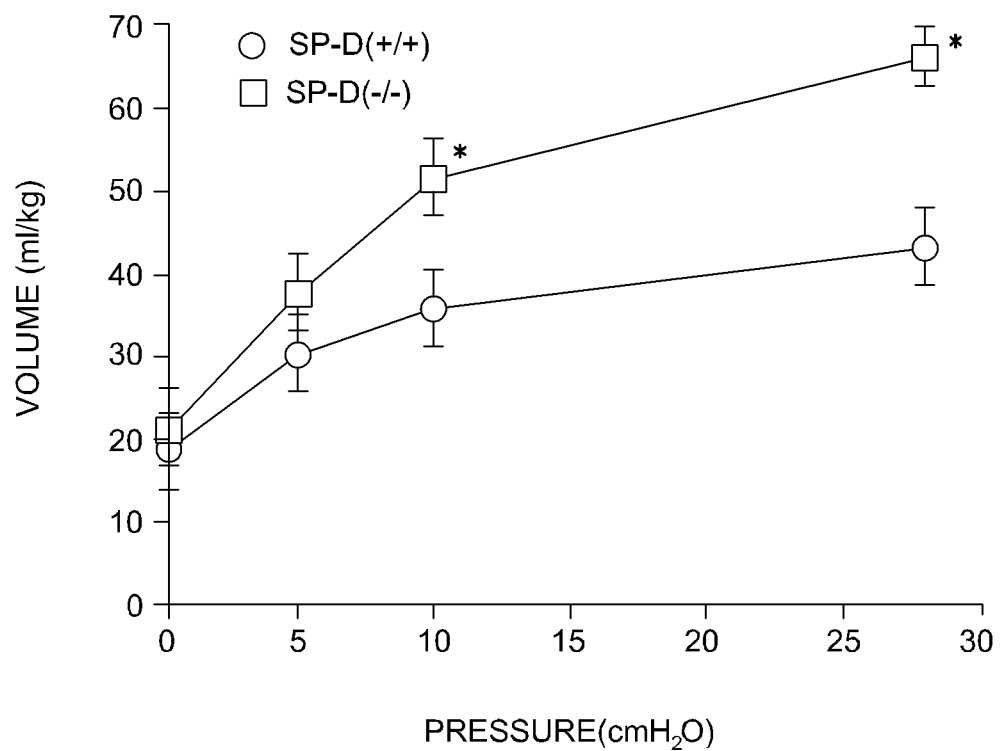
FIG. 2: Deflation limbs of pressure-volume curves from SP-D (+/+) and SP-D (−/−) mice. Data are expressed as ml/kg and represent the mean±SE.

Premature newborns are routinely resuscitated by manual ventilation in the delivery room, followed by mechanical ventilation and surfactant treatment in the neonatal intensive care unit. The premature lung requires high inflating pressures and oxygen for adequate ventilation and oxygenation and is highly susceptible to injury because of its structural immaturity, surfactant deficiency, presence of fetal lung fluid, and immature immune system—factors that are likely to contribute to the development of the chronic lung disease bronchopulmonary dysplasia (BPD). Surfactant treatment is routinely given to very low birth weight (i.e., <1,500 g) preterm infants as early as possible after birth for the purpose of resuscitation in an effort to prevent and/or treat neonatal respiratory distress.

As described herein, rhSP-D can be added to resuscitation surfactant to improve surfactant distribution, minimize inhibition of surfactant function by leaked proteins, and prevent bronchopulmonary dysplasia (BPD)—a frequent consequence of the resuscitation process. Some embodiments relate to methods and compositions for the treatment of disorders associated with lung injury, including BPD. In one embodiment, recombinant human surfactant protein D (rhSP-D) is given in combination with a surfactant formulation to a mammal in need of treatment for a lung disorder.

In some embodiments, the mammal is a human. The human can be, e.g., an adult, a child, or an infant. In some embodiments, the infant is a newborn infant or a premature newborn infant. In some embodiments, the premature newborn infant is born at about 21, 22, 23, 24, 25, 26, 27, 28, 29, 30, 31, 32, 33, 34, 35, 36, or 37 weeks gestational age. In some embodiments, the newborn infant has a low birth weight. For example, in some embodiments, the birth weight of the newborn infant is less than about 500, 600, 700, 800, 900, 1000, 1100, 1200, 1300, 1400, 1500, 1600, 1700, 1800, 1900, 2000, 2100, 2200, 2300, 2400, or 2500 grams. In a preferred embodiment, the mammal is a premature newborn infant with respiratory disease (such as neonatal respiratory distress syndrome (nRDS)), or an infant at risk of developing or with symptoms of BPD.

In the embodiments described herein, a surfactant formulation can encompass one or more proteins, protein fragments, or mimics thereof. For example, in some embodiments, the surfactant formulation contains surfactant protein A (SP-A), surfactant protein B (SP-B), or surfactant protein C (SP-C). In some embodiments, the surfactant formulation contains a combination of surfactant proteins, such as the combination of SP-B and SP-C. In some embodiments, the surfactant formulation contains a fragment of a surfactant protein. In some embodiments, the surfactant formulation contains surfactant lipids. For example, in some embodiments, the surfactant formulation contains dipalmitoylphosphatidylcholine (DPPC). In some embodiments, the formulation contains DPPC and at least one of phosphatidylglycerol (PG) and phosphatidylinositol (PI). In a preferred embodiment, the surfactant formulation contains SP-B, SP-C, and DPPC.

In some embodiments, the surfactant formulation contains an animal derived surfactant. In some embodiments, the animal derived surfactant is a commercially available surfactant, such as ALVEOFACT®, CUROSURF®, INFASURF®, or SURVANTA®. In some embodiments, the animal derived surfactant is BLES®, SURFACEN®, or CLSE®. In some embodiments, the surfactant formulation contains a synthetic surfactant. In some embodiments, the synthetic surfactant is a commercially available synthetic surfactant, such as EXOSURF®, PUMACTANT®, SURFAXIN®, AEROSURF®, VENTICUTE®, or CHF 5633. In some embodiments, a combination treatment of rhSP-D and an animal surfactant is provided. In some of these embodiments, the animal surfactant contains at least one surfactant protein and at least one lipid. In some embodiments, a combination treatment of rhSP-D and a synthetic surfactant is provided. In some of these embodiments, the synthetic surfactant contains at least one recombinant protein, at least one surfactant protein fragment or mimic of a surfactant protein, and at least one lipid.

In some embodiments, the surfactant formulation contains a purified surfactant protein. In some embodiments, the surfactant formulation contains a surfactant protein that is not SP-D. In some embodiments, the surfactant formulation does not contain a surfactant protein. In some embodiments, the surfactant formulation contains a lipoprotein complex. For example, in some embodiments, the surfactant formulation contains a phospholipoprotein complex.

The compositions described herein can be administered by any suitable route, including orally, intratracheally, parentally, by inhalation spray, rectally, or topically in dosage unit formulations containing conventional pharmaceutically acceptable carriers, adjuvants, and vehicles. As used herein, the term "parenteral" includes subcutaneous, intravenous, intraarterial, intramuscular, intrasternal, intratendinous, intraspinal, intracranial, intrathoracic, infusion, or intraperitoneal administration. In a preferred embodiment, rhSP-D and a surfactant formulation are administered intratracheally. In another preferred embodiments, rhSP-D and a surfactant formulation are administered in an aerosolized form.

The compositions described herein can be administered as a single dose or in multiple doses. In some embodiments, the composition is administered once. In some embodiments, the composition is administered more than once. In a preferred embodiment, the composition is administered to a premature newborn infant in one or two doses. In some embodiments, rhSP-D and the surfactant formulation are each administered once per day. In some embodiments, rhSP-D and the surfactant formulation are administered together once per day. In some embodiments, rhSP-D and the surfactant formulation are administered together more than once per day.

In some embodiments, one or both of rhSP-D and the surfactant formulation is administered one, two, three, four, or more times per day. However, either or both can be administered less than once per day, e.g., about once every 2, 3, 4, 5, 6, 7, 8, 9, 10, 11, 12, 13, or 14 days.

Suitable dosage ranges vary, but in general, the rhSP-D can be administered in a dosage of about 0.1, 0.2, 0.3, 0.4, 0.5, 0.6, 0.7, 0.8, 0.9, 1, 2, 3, 4, 5, 6, 7, 8, 9, or 10 mg/kg body weight. In a preferred embodiment, the rhSP-D is provided in a dosage of about 1 mg/kg to about 2 mg/kg body weight. In general, the surfactant formulation can be administered in a dosage of about 25, 50, 75, 100, 125, 150, 175, 200, 300, 400, or 500 mg/kg body weight In a preferred embodiment, the surfactant formulation is provided in a dosage of about 100 mg/kg to about 200 mg/kg. For example, in a preferred embodiment, the rhSP-D is provided in a dosage of about 2 mg/kg body weight, and the surfactant formulation is provided in a dosage of about 100 mg/kg body weight. In another preferred embodiment, the rhSP-D is provided in a dosage of about 7 mg/kg body weight, and the surfactant formulation is provided in a dosage of about 100 mg/kg body weight.

The selection of a particular dosage may be based on the weight or identity of a mammal, the dosage, and/or the dosing schedule of another co-administered compound. However, in some embodiments, it may be necessary to use dosages outside these ranges. In some embodiments, the daily dosage of rhSP-D and a surfactant protein is the same, and in some embodiments, the daily dosage is different. In some embodiments, the daily dose is administered in a single dosage form. In some embodiments, the daily dose is administered in multiple dosage forms.

In some embodiments, at least one of rhSP-D and the surfactant formulation is administered in consistent daily dosages throughout the period of treatment. In some embodiments, at least one of rhSP-D and the surfactant formulation is administered in varying daily dosages during the period of treatment. In some of these embodiments, the daily dosages comprise increasing daily dosages over time. In some of these embodiments, the daily dosages comprise decreasing daily dosages over time.

In some embodiments, the dosage is adjusted so that the mammal maintains or exhibits reduced symptoms of a disorder. For example, in some embodiments, the dosage is adjusted so that a patient exhibits a reduction in symptoms of BPD. However, the dosage may also be adjusted by a treating physician based on a patient's particular needs. Further, the exact formulation, route of administration, and dosage can be chosen by a physician in view of the patient's condition.

In some embodiments, at least one of rhSP-D and the surfactant formulation is administered with varying frequency during treatment. In some of these embodiments, the varying frequency comprises a decreased frequency over time. For example, one or both of rhSP-D and the surfactant formulation can be initially administered more than once per day, followed by administration only once per day at a later point in treatment. In some embodiments, the daily dosage of at least one of rhSP-D and the surfactant formulation is consistent despite the varying frequency of administration.

In some embodiments, rhSP-D and the surfactant formulation are administered in a single pharmaceutical composition, such as a pharmaceutical composition comprising rhSP-D, a purified surfactant protein, a lipid, and pharmaceutically acceptable carriers.

In some embodiments, administration is continued for a certain amount of time or until a particular outcome is achieved. For example, in some embodiments, administration of the compositions provided herein is continued for a period of at least about 1, 2, 3, 4, 5, 6, 7, 8, 9, 10, 11, 12, 16, 20, 24, 36, 48, 72, 84, 96, 108, or 120 hours. In some embodiments, administration of rhSP-D and the surfactant formulation is continued until the reduction in symptoms of respiratory distress is stabilized for a period of at least about 12, 16, 20, 24, 36, 48, 72, 84, 96, 108, or 120 hours. In a preferred embodiment, symptoms of respiratory distress are stabilized for a period of about 72 hours to about 96 hours. In some embodiments, administration is continued for the duration of the life of a mammal. For example, in some embodiments, administration is continued daily, weekly, or monthly for the life of a human.

The compositions described herein may be accompanied by instructions for administration. Such notice, for example, may be the labeling approved by the U.S. Food and Drug Administration for prescription drugs, or the approved product insert. Compositions formulated in a compatible pharmaceutical carrier may also be prepared, placed in an appropriate container, and labeled for treatment of an indicated condition.

Instructions and/or information may be present in a variety of forms, including printed information on a suitable medium or substrate (e.g., a piece or pieces of paper on which the information is printed), computer readable medium (e.g., diskette, CD, etc., on which the information has been recorded), or a website address that may be accessed via the internet. Printed information may, for example, be provided on a label associated with a drug product, on the container for a drug product, packaged with a drug product, or separately provided apart from a drug product, or provided in a manner in which a patient can independently obtain the information (e.g., a website). Printed information may also be provided to a medical caregiver involved in treatment of a patient.

The compositions described herein can be provided prior to, simultaneously with, or subsequent to ventilation and/or oxygen treatment. In some embodiments, the mammal receives ventilation and/or oxygen treatment for a period of time prior to receiving a composition. For example, in some embodiments, the mammal receives ventilation and/or oxygen treatment for about 1, 2, 3, 4, 5, 10, 15, 20, 25, 30, 35, 40, 45, 50, 55, 60, 75, 90, 105, or 120 minutes prior to receiving a composition. In some embodiments, the mammal receives ventilation and/or oxygen treatment for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 hours prior to receiving a composition. In a preferred embodiment, a premature infant receives ventilation immediately following birth, and treatment with rhSP-D and a surfactant formulation within about 20 minutes of birth. For example, a premature infant can be intubated with an endotracheal tube and placed on a ventilator at birth, then receive rhSP-D and a surfactant formulation through the endotracheal tube about 20 minutes following birth. In some embodiments, the ventilation is manual ventilation. In some embodiments, the ventilation is mechanical ventilation. In some embodiments, the ventilation is both manual and mechanical. For example, in some embodiments, a premature infant is resuscitated by manual ventilation in the delivery room, followed by mechanical ventilation and treatment with rhSP-D and a surfactant formulation in the neonatal intensive care unit. In some embodiments, the mammal receives a composition about 1, 2, 3, 4, 5, 10, 15, 20, 25, 30, 35, 40, 45, 50, 55, 60, 75, 90, 105, or 120 minutes prior to ventilation and/or oxygen treatment for a lung disorder. In some embodiments, the mammal receives a composition about 1, 2, 3, 4, 5, 6, 7, 8, 9, 10, 11, 12, 13, 14, 15, 16, 17, 18, 19, 20, 21, 22, 23, or 24 hours prior to treatment for a lung disorder. For example, in some embodiments, a patient with cystic fibrosis receives a composition within an hour of undergoing ventilation treatment. However, this timeframe can be adjusted by a treating physician based on a patient's particular needs.

In some embodiments, the mammal receives alternating treatment with a composition and ventilation and/or oxygen. For example, in some embodiments, the mammal receives ventilation, followed by a composition, followed by ventilation. In some embodiments, the mammal receives alternating and simultaneous treatment with a composition and ventilation and/or oxygen. For example, in some embodiments, the mammal receives a composition, followed by ventilation, followed by the composition and ventilation.

In some embodiments, the mammal is administered a composition described herein within a defined period of time following birth. In some embodiments, the mammal is administered a composition immediately following birth. In some embodiments, the mammal is administered a composition within about 1, 2, 3, 4, 5, 6, 7, 8, 9, 10, 15, 20, 25, 30, 35, 40, 45, 50, 55, 60, 75, 90, 105, or 120 minutes of birth.

The term "treatment" can include any intervention performed with the intention of preventing the development or altering the pathology of a disorder. Accordingly, "treatment" refers to both therapeutic treatment and prophylactic or preventative measures. Those in need of treatment include those already with a disorder, as well as those in which the disorder is to be prevented. In some embodiments, the compositions described herein are useful to reduce the risk of developing BPD. In some embodiments, the compositions described herein are useful for reducing pulmonary inflammation associated with lung injury. In some embodiments, the compositions described herein are useful for reducing the symptoms of BPD resulting from lung injury.

The terms "protein," "polypeptide," and "peptide" are used interchangeably herein to refer to a polymer of amino acid residues. The terms can apply to amino acid polymers in which one or more amino acid residue is an analog or mimic of a corresponding naturally occurring amino acid, as well as to naturally occurring amino acid polymers. Polypeptides can be produced via several methods known in the art. For example, polypeptide products can be biochemically synthesized by employing standard solid phase techniques. Such methods include, but are not limited to, exclusive solid phase synthesis, partial solid phase synthesis methods, fragment condensation, and classical solution syntheses known to those of skill in the art. Polypeptides can also be generated using recombinant techniques known to those of skill in the art. For example, polypeptides can be synthesized by cloning a polynucleotide comprising the cDNA of a gene into an expression vector and culturing the cell harboring the vector to express the encoded polypeptide. In addition, polypeptides can be purified using methods known to those of skill in the art, including preparative high performance liquid chromatography. As used herein, the term "purified" does not require absolute purity; rather, it is intended as a relative definition. In some embodiments, a polypeptide is about 75%, 80%, 85%, 90%, 95%, or 99% pure. Polypeptides can also be modified, e.g., by the addition of carbohydrate residues to form glycoproteins. The terms "protein," "polypeptide," and "peptide" include glycoproteins, as well as non-glycoproteins.

The compositions described herein can include pharmaceutically acceptable carriers, such as adjuvants, excipients, and/or stabilizers that are nontoxic to the cell or mammal being exposed thereto at the dosages and concentrations employed. In some embodiments, the pharmaceutically acceptable carrier is an aqueous pH buffered solution. For example, in some embodiments, compositions are pH adjusted with sodium bicarbonate. Examples of pharmaceutically acceptable carriers include, but are not limited to, adjuvants, lipids, preservatives, stabilizers, wetting agents, emulsifiers, and buffers. In some embodiments, the compositions contain a lipid. For example, in some embodiments, the compositions contain phosphatidylcholine (PC), dipalmitoylphosphatidylcholine (DPPC), phosphatidylglycerol (PG), phosphatidylethanolamine (PE), phosphatidylinositol (PI), sphingomyelin, tripalmitoylglycerol, palmitic acid, or mixtures thereof, In a preferred embodiment, compositions contain a rhSP-D, a surfactant protein, DPPC, and PI. Further, compositions can be prepared in solid form (including granules, powders or suppositories) or liquid form (e.g., solutions, suspensions, or emulsions). For example, in some embodiments, compositions are suspended in sodium chloride solution. In a preferred embodiment, the composition is in an aerosolized formulation.

Also described herein is an SP-D (−/−) knockout mouse useful for identifying the role of SP-D in normal lung function and development and to demonstrate the temporal progression of postnatal airspace enlargement and spontaneous inflammatory changes in the lungs of these mice. SP-D (−/−) mice develop progressive pulmonary emphysema, associated with chronic inflammation and increased oxidant production by alveolar macrophages. The lung abnormalities make this mouse an excellent model for emphysema. Because there are very few existing therapies for treatment of emphysema, the most common being lung volume reduction surgery, the model is urgently needed. Described herein are a number of ways to test SP-D protein and expression vectors, and potential pharmaceuticals in the mouse model for efficacy in treating emphysema or other forms of chronic lung injury. Described herein is the use of SP-D protein and expression vectors to treat various other diseases of aberrant surfactant production, pulmonary fibrosis, sarcoidosis, lung injury, toxicant/oxygen exposure, infection, increased oxidant exposure. Also described herein is the use of SP-D cDNA, SP-D antibodies, PCR, and differential hybridization techniques to identify patients at risk for emphysema, pulmonary distress syndromes, and other types of respiratory diseases. Although other materials and methods similar or equivalent to those described herein can be used in the practice or testing of the present invention, the preferred methods and materials are now described. Example 1 describes steps for producing a SP-D (−/−) mouse.

TABLE 1

Comparison of Body Weights, Lung Volumes, and Volume-to-Body Weight Ratios
(Mean ± SE)

| AGE | BODY WEIGHTS (g) | | LUNG VOLUMES (ml) | | LV:BW ($Ml/g \times 10^{-2}$) | |
|---|---|---|---|---|---|---|
| | SP-D (−/−) | SP-D (+/+) | SP-D (−/−) | SP-D (+/+) | SP-D (−/−) | SP-D (+/+) |
| 2 day | 1.8 ± 0.1* | 3.4 ± 0.1 | ND | ND | ND | ND |
| 5 day | 3.7 ± 0.3 | 4.6 ± 0.2 | ND | ND | ND | ND |
| 7 day | 3.9 ± 0.2* | 5.3 ± 0.2 | ND | ND | ND | ND |
| 14 day | 6.6 ± 0.2* | 7.7 ± 0.2 | ND | ND | ND | ND |
| 17 day | 10.9 ± 0.5 | 10.6 ± 0.7 | 0.36 ± 0.02 | 0.36 ± 0.03 | 3.25 ± 0.05 | 3.36 ± 0.03 |
| 3 wk | 10.9 ± 0.5* | 14.1 ± 1.2 | 0.36 ± 0.01 | 0.37 ± 0.03 | 3.43 ± 0.21** | 2.50 ± 0.18 |
| 6 wk | 23.2 ± 0.6 | 24.7 ± 0.5 | 0.63 ± 0.03 | 0.58 ± 0.02 | 2.71 ± 0.13** | 2.25 ± 0.18 |
| 9 wk | 25.2 ± 1.2 | 27.8 ± 1.3 | 0.55 ± 0.03 | 0.61 ± 0.02 | 2.10 ± 0.16 | 2.20 ± 0.09 |
| 28 wk | 36.9 ± 4.3 | 31.2 ± 1.6 | 0.67 ± 0.09 | 0.58 ± 0.06 | 2.03 ± 0.51 | 1.86 ± 0.10 |

*Significant statistical differences were observed in body weights at 2 day, p = 0.00001; 7 day, p = 0.0002; 2 wk, p = 0.007; and 3 wk, p = 0.04.
**Significant statistical differences in LV:BW ratios were observed at 3 wk (p = 0.02), due to differences in body weight, and at 6 wk (p = 0.03), although body weights and lung volumes were not statistically different at this latter time point. N = 3-71 animals per group.
LV:BW, lung volume-to-body weight ratio;
ND, not determined.

Example 1

SP-D (−/−) Knockout Mouse Construction

SP-D (−/−) mice were generated by targeted gene inactivation. Integration of a pGKneo targeting vector containing sequences from exon 2 of the SP-D gene generated a deletion of the second exon of the SP-D gene, which included removal of the initiating methionine and translation initiation sequences. The mouse SP-D gene sequence of Exons 1 and 2 can be found under Genbank accession No. AF047741. The targeting vector was designed using pGKneo by first subcloning a 5.1-kb blunt ended KpnI-tailed HindIII genomic fragment encoding intron 2 through exon 6 into a KpnI site between the neomycin-resistance cassette and the thymidine kinase cassette. Subsequently, a 1.5-kb genomic PstI fragment containing a portion of intron I was tailed with XhoI linkers and cloned into an XhoI site 5' from the neomycin-resistance cassette eight of 104 ES clones surviving the double selection process were correctly targeted as determined by both 5' and 3' PCR analyses. Clone 93, a highly undifferentiated and proliferative clone, was expanded and injected into C57/B16 blastocysts generating chimeric males. Chimeric males were bred to NIH Swiss Black females. A female bearing the targeted gene was obtained and bred to NIH Swiss Black males to generate normal SP-D (−/−) and SP-D (±) mice. The distribution of genotypes from heterozygotic matings followed a Mendelian pattern, with 30 (+/+), 45 (+/−), and 25% (−/−) of 115 offspring, indicating that there were no obvious abnormalities in survival related to SP-D alleles.

SP-D(−/−) mice survive and breed normally in the vivarium under barrier containment facilities at Children's Hospital Medical Center, Cincinnati, Ohio. Mice have been viral free as assessed by serology. No serological evidence of viral infection in SP-D(−/−) mice was detected at necropsy.

To determine genotype, DNA from tail clips was digested with BamHI and probed with a PCR product derived from genomic mouse DNA, containing exon 2 and part of intron 2, and with the G418 resistance cDNA clone. This demonstrated a simultaneous loss of exon 2 with appearance of sequences encoding G418 resistance in SP-D (±) and SP-D (−/−) mice.

To demonstrate that SP-D was not expressed in null animals, RNA blot analysis was conducted with total lung RNA from null, normal, and heterozygotic animals. The results showed approximately 50% reduction in the intensity of the SP-D hybridization band in heterozygous animals with a total absence of normally sized SP-D mRNA in null animals. After prolonged exposure, a diffuse mRNA band approximately 150 nucleotides smaller than the normal SP-D mRNA was detected. By scanning densitometry, this band represents less than 5% of the intensity of the normal SP-D transcript from heterozygous animals.

Western blot analysis of lung homogenates using rabbit anti-rat SP-D antiserum revealed SP-D was reduced approximately 50% in heterozygous SP-D (+/−) mice and was absent in SP-D (−/−) mice.

Both SP-D (−/−) and SP-D (+/−) mice survived normally in perinatal and postnatal periods. At selected ages, body, lung, and heart weights were obtained by direct measurement; and lung and heart volumes were obtained by fluid displacement. Lung protein and DNA content were assessed using bovine serum albumin and salmon sperm DNA, respectively, as standards. Body weights of SP-D (−/−) mice were slightly smaller prior to weaning, but were not significantly different from SP-D (+/+) mice after 3 weeks of age, Table 1. While lung volumes were not significantly different, lung-volume-to-body-weight ratios were increased in SP-D (−/−) mice at 3 and 6 weeks of age, Table 1. No significant differences were observed in heart volumes or heart-volume-to-body-weight ratios. At maturity (5 months), no changes in wet lung weight, total lung DNA or protein were noted.

However, while no abnormalities were observed in body weight, examples 2 through 5 describe the other abnormalities or changes found in SP-D (−/−) mice.

Example 2 demonstrates the effect on phospholipid levels. Alveolar and tissue phospholipid levels, specifically phosphatidylcholine pool levels, were markedly increased while total bronchoalveolar lavage (BAL) protein levels remained unchanged.

Example 2

Phospholipid Levels in the SP-D (−/−) Mouse

Alveolar, tissue and total saturated phosphatidylcholine (Sat-PC) (p<0.001) was increased about 3-fold in SP-D (−/−) mice. Levels of Sat-PC were not altered in SP-D (+/−) mice.

For alveolar lavage phospholipid composition analysis, two to four samples consisting of the pooled lavage from two to three mice were evaluated for the relative abundance of phosphatidylcholine, phosphatidylethanolamine, phosphatidylglycerol, phosphatidylinositol, sphingomyelin, and lyso-bis-phosphatidic acid. Phospholipid composition did not differ among genotypes. Incorporation of ($^3$H)choline into total lung Sat-PC was slightly increased 8 hr following injection, incorporation being approximately 20% greater in SP-D (−/−) mice ($p<0.05$).

This result was completely unexpected in that previous work suggested a definite role for SP-A and a limited role for SP-D in lung phospholipid homeostasis. Previous diseases associated with surfactant homeostasis involved accumulations of both surfactant proteins and lipids, thus the SP-D (−/−) null mouse demonstrates for the first time that SP-D is an important player in surfactant lipid homeostasis and that surfactant lipid and protein homeostasis can be dissociated in vivo, since the total protein concentration in the surfactant did not change. However, there was a modest decrease in the total concentration of SP-A as explained in Example 3.

Example 3

Reduction in SP-A Levels in the SP-D (−/−) Mouse

No differences in SP-B and SP-C mRNAs or proteins were observed in SP-D (−/−) mice. In contrast, Northern blot hybridization of total lung RNA from SP-D (+/+), SP-D (+/−), and SP-D (−/−) mice and hybridization with and SP-A probe showed that SP-A mRNA was reduced in SP-D (−/−) mice. Consistent with the reduction in SP-A mRNA, BAL SP-A protein was apparently reduced by about 25% in SP-D (−/−) mice as assessed by Western blot analysis of alveolar lavage from three mice.

Therefore, SP-D has a role in the regulation of SP-A production. Since SP-A is involved in host defense in the lungs, SP-D can affect host defense in two ways. By up-regulation of SP-A production and by direct interaction with immune and microbial cells.

The ultrastructure of the phospholipid rich material isolated form the BAL of the SP-D (−/−) mice was evaluated as explained in Example 4.

Example 4

Changes in Surfactant Structure in SP-D (−/−) Mouse

Large aggregate surfactant was isolated from pooled alveolar lavage of SP-D (−/−) and SP-D (+/+) mice and examined by EM using the technique outlined below. Lipid aggregates in SP-D (−/−) mice were enlarged and organized into electron dense phospholipid arrays and contained less tubular myelin compared with SP-D (+/+) mice. The ultrastructure proved to be markedly abnormal, containing reduced quantities of tubular myelin and forming unique densely packed lipid structures. Therefore, SP-D has a role in the structural organization of alveolar lipids.

Aggregate forms from alveolar lavage. Surfactant in alveolar was can be separated into large aggregate (heavy, dense) and small aggregate (light, visicular) fractions by centrifugation. Alveolar washes were centrifuged at 40,000×g over 0.8 M sucrose cushion for 15 min. The large aggregate surfactant then was collected from the interface, diluted with normal saline and centrifuged again at 40,000×g for 15 min. The supernatant from the first 40,000×g centrifugation that contains small aggregate surfactant is concentrated at 4° C. by ultrafiltration using a 300,000 molecular weight retention filter (Minitan, Miliore Corp., Bedford, Mass.) or centrifugal concentrators (Amicon Corp., Danvers, Mass.). The small aggregate surfactant is diluted with 50 ml normal saline and ultrafiltered 3 times to remove soluble proteins.

Lastly, the structure of the lung was analyzed. Although, normal in SP-D (+/−) mice, increased numbers of large foamy alveolar macrophages and enlarged alveoli were observed in SP-D (−/−) mice. In Example 5, the method and results for identifying lung abnormalities is outlined.

Example 5

Lung Abnormalities in the SP-D (−/−) Mouse

To determine whether absence of SP-D expression led to structural abnormalities, lungs from null, normal, and heterozygous mice were inflation fixed, and morphology and histochemical analysis was done on sections by light microscopy. There was no evidence of infection and no obvious alterations in airway epithelial cells at the level of light microscopy. However, heterogeneous abnormalities in lung parenchyma, with enlarged alveoli, were consistently observed in the SP-D (−/−) but not SP-D (+/−) or SP-D (+/+) controls.

Morphological and Histochemical Method

Lung tissue from SP-D (+/+) and SP-D (−/−) mice were sacrificed at 2 weeks, 3 weeks and 6 weeks. Animals were weighed, anesthetized with a 4:1:1 mixture of ketamine, acepromazine and xylazine, and exsanguinated by severing the inferior vena cava and descending aorta. The trachea was cannulated, and the lungs were collapsed by piercing the diaphragm. The lungs were inflation-fixed at 25 cm of water pressure with 4% paraformaldehyde in phosphate buffered saline (PBS) for 1 minute. The trachea was tied off as the cannula was removed in order to maintain the fixative in the inflated lung. Excised lungs and heart were allowed to equilibrate in cold fixative until they had sunk to the bottom of the container. Lung and heart volumes were then determined by fluid displacement. Each lobe was measured along its longest axis, bisected perpendicularly to the long axis, and processed into paraffin blocks. Five micron sections were cut in series throughout the length of each lobe, loaded onto polysine-coated slides, and stained with hematoxylin and eosin, Masson's trichrome stain for collagen, or ocein for elastin.

Lung Morphology

In more detail, examination within the first 2 weeks of life demonstrated no detectable abnormalities in lung morphology, although increased numbers of normal appearing alveolar macrophages were noted in the alveoli of SP-D (−/−) mice at 14 days of age. In contrast abnormalities in lung histology were observed in SP-D (−/−) mice at 3 and 6 weeks of age consisting of enlarged airspaces and infiltration with atypical, foamy, alveolar macrophages. Enlarged airspaces associated with the accumulation of hypertrophic, foamy, alveolar macrophages and perivascular/peribronchiolar monocytic infiltrates were observed by 6 to 7 months of age, although the extent of airspace enlargement in individual SP-D (−/−) mice varied from moderate to severe in this age group.

In 7 month old SP-D (−/−) mice, subpleural fibrotic lesions were observed that stained intensely for collagen. Abnormalities in elastin deposition were also observed in the parenchyma of lungs from SP-D (−/−) mice at this time point. These consisted of regions of lung parenchyma with short thick, and more highly coiled elastic fibers, as well as regions of inflammation where elastin staining was decreased in adjacent alveolar septa (adjacent to macrophage accumulation and fibrosis).

Increased bronchial-associated lymphocytic tissue (BALT) was noted in the SP-D (−/−) mice. Intensity of SP-B immunostaining in type II cells was similar among the three genotypes. Type II cells were purified as outlined below. However, there were focal areas of increased numbers of large, foamy intra-alveolar cells, which appeared to be alveolar macrophages containing abundant cytoplasmic vesicles. These cells increased in size as a result of increasing number and volume of cytoplasmic vesicles. The vesicles stained with Nile Red and fluoresced when excited with 520-550 nm green light after staining with Nile Blue and thus contained lipid or phospholipid. These macrophages were also stained by SP-B antiserum. In alveolar lavage, approximately 4-fold more macrophages ($1.2 \times 10^6$ per mouse) were observed in SP-D (−/−) compared with normal mice ($0.36 \times 10^6$/mouse), but there were no changes in relative neutrophil or lymphocyte cell counts. Macrophage size was estimated from the diameter of fixed and stained macrophages from cytospin preparations sedimented onto glass slides at 1500×g for 2 min. Mean diameter of macrophages from (+/+) was 11.75±1.75 μm compared with (−/−) mice 18.75±7.25 μm. Abnormally large macrophages, defined as those with a diameter of twice normal, comprised 22.4±0.6% of the macrophages from (−/−) mice compared with 18±1.0% from (+/+) mice. Numbers and morphology of alveolar macrophages were not different in SP-D (+/−) mice. Ultrastructural characteristics of type II cells were similar in SP-D (−/−) compared with SP-D (+/+) mice. The morphology of the alveolar macrophages is consistent with that of activated "foam" cells, known to be associated with inflammation.

Isolation of Murine Type II Cells.

Type II cells were isolated using the following method. Mice are anesthetized by intraperitoneal injection and pentobarbital (50 mg/ml 3.25 ml/kg body weight). After opening the abdominal cavity, mice are exsanguinated by severing the inferior vena cava. The trachea is exposed, cannulated with a 20 gauge luer stub adaptor, and secured by a suture. The chest plate is removed and lungs perfused with 10-20 ml sterile saline via the pulmonary artery until visually free of blood. Dispase (Collaborative Research, Inc., Bedford, Mass.) is instilled into the lungs via the tracheal catheter, followed by 1% low melt agarose, warmed to 45° C. Lungs are immediately covered with ice and incubated for 2 minutes to set the agarose. Lungs are dissected out, put in a culture tube containing an additional 1 ml Dispase, and incubated for 45 minutes at room temperature. Lungs are next transferred to a 60 mm culture dish containing 100 U/ml DNAase 1 (Sigma, St. Louis, Mo.) in 7 ml DMEM (Gibco BRL, Gaithersburgh, Md.). The tissue is gently teased away from the airways and swirled for 5 minutes. Cells are then placed on ice until being filtered. The cell suspension is successively filtered through 100 μm and 40 μm cell strainers, and then through 25 μm nylon gauze (Tetko, Briarcliff Manor, N.Y.). Cells are pelleted for 7 min at 130×g at 4° C. and resuspended in 10 ml DMEM with 10% FBS (Intergen Co., Purchase, N.Y.). Crude cell suspensions are added to 100 mm culture dishes that were previously coated with CD-45 and CD-32 antibodies (Pharmigen, San Diego, Calif.) and incubated for 102 hours at 37° in the presence of 5% $CO_2$. Plates are removed from the incubator and gently "panned" to free settled type II cells. The cell suspension is centrifuged at 130×g at 4° C. and resuspended in 10 ml DMEM with 10% FBS (Intergen Co., Purchase, N.Y.). Crude cell suspensions are added to 100 mm culture dishes that were previously coated with CD-45 and CD-32 antibodies (Pharmigen. San Diego, Calif.) and incubated for 102 hours at 37° C. in the presence of 5% $CO_2$. Plates are removed from the incubator and gently "panned" to free settled type II cells. The cell suspension is centrifuged at 130×g for 7 minutes and cells are resuspended in DMEM containing 10% FBS.

Airspace and Respiratory Parenchyma

Morphometric measurements were performed on mice at 5 days (0.5 weeks), 14 days (2 weeks) and 17 days (2.5 weeks), 3 and 6 weeks, and 6 to 7 months of age. the overall proportion (% fractional area) of respiratory parenchyma and airspace was determined using a point counting method. Measurements were performed on sections taken at intervals throughout the left, right upper, or right lower lobes. Slides were viewed using a 20× objective, and the images (fields) were transferred by video camera to a computer screen using Meta-Morph imaging software (Universal Imaging Corp., West Chester, Pa.). A computer-generated, 121-point lattice grid was superimposed on each field, and the number of intersections (points) falling over respiratory parenchyma (alveoli and alveolar ducts) or airspace was counted. Points falling over bronchioles, large vessels, and smaller arterioles and venules were excluded from the study. Fractional areas (% Fx Area) were calculated by dividing the number of points for each compartment (n) by the total number of points contained within the field (N), and then multiplying by 100:

$$\% \ Fx\ Area = n/N \times 100$$

Ten fields per section were analyzed to gather the data. The x and y coordinates for each field measured were selected using a random number generator.

While, as shown in FIGS. 1A-1D, no differences in the relative proportion (% fractional area) of airspace (a) and respiratory parenchyma (b) were observed at 5 days (0.5 weeks), 14 days (2 weeks), or 17 days (2.5 weeks) of age, the % fractional area of airspace was increased significantly (p=0.013) in SP-D (−/−) mice by 3 weeks of age. More specifically, the fractional area devoted to both airspace (a) and parenchyma (b) diverged significantly between the two different genotypes at 3 weeks (*p=0.013), 6 weeks (*p=0.0007), and 28 weeks (*p=0.004) of age. Likewise, the % fractional area of respiratory parenchyma was decreased in SP-D (−/−) mice compared to age-matched SP-D (+/+) controls (34% parenchyma/66% airspace compared to 42.5% parenchuma/57.5% airspace, respectively), FIGS. 1A-1D. Relative proportions of airspace and respiratory parenchyma continued to diverge significantly from controls at later time points, the % fractional areas ranging from 27% parenchyma/73% airspace to 37% parenchyma/63% airspace in 7 month old SP-D (−/−) mice (n=5). Age-matched SP-D (+/+) controls showed less variability, ranging from 45% parenchuma/55% airspace to 47% parenchyma/53% airspace, at this time point (n=4). The overall percent reduction in parenchyma at 7 months of age in the SP-D (−/−) mice was 32% of control values, while the percent increase in airspace in the SP-D (−/−) mice was 27% of control values.

Cellular Proliferation

Animals were pre-injected with BrdU 4 hours prior to sacrifice in order to assess alterations in cellular proliferation. Immunohistochemical detection of incorporated BrdU was performed using a commercially available kit (Zymed Laboratories, Inc., San Francisco, Calif.). Sections of small intestine from each animal were immunostained in parallel with the lung sections as a positive control for BrdU incorporation.

BrdU labeling indices were relatively low, and no changes in BrdU labeling of respiratory parenchymal cells or alveolar macrophages were observed in the lungs from SP-D (−/−) mice compared to controls.

Lung Volumes

Determination of lung volumes using pressure-volume curves was as follows: Twelve week-old mice were injected with sodium pentobarbital and placed in a chamber containing 100% oxygen to ensure complete collapse of alveoli by oxygen absorption. Mice were killed by exsanguination, the trachea cannulated and connected to a syringe linked to a pressure sensor via a three-way connector (Mouse Pulmonary Testing System, TSS Incorporated, Cincinnati, Ohio). After opening the diaphragm, lungs were inflated in 75 μl increments every 10 seconds to a maximum pressure of 28 cm of water and then deflated. Pressure-volume curves were generated for each animal, determining lung volumes (divided by body weight) at 10, 5, and 0 cm of water during the deflation curve. In FIG. 2, pressure-volume curves were generated in 5-6 mice at 12 weeks of age. Lung volumes associated with the deflation limbs of pressure-volume curves were significantly greater for 12 week old SP-D (−/−) mice compared age-matched to SP-D (+/+) mice at 10 cm $H_2O$ and at the maximum pressure of 28 cm $H_2O$ (*$p<0.05$).

Statistically significant differences were determined by using either analysis of variance for fractional areas and pressure-volume curves, followed by the Student-Newman-Keuls procedure, or the student's T test for comparison of body weights, lung and heart volumes, volume:body weight ratios, total protein and DNA content. Differences of $p<05$ were considered significant. Values are given as mean±SE.

Increased lung volumes were readily apparent in SP-D (−/−) mice at 12 weeks of age, consistent with histologic and morphometric studies demonstrating emphysema, see FIG. 2.

Alveoli

The enlarged alveoli were consistently observed in the SP-D (−/−) mice. Therefore, SP-D is very likely to be involved in the regulation of alveolar remodeling in the lungs. Because abnormalities and airspace remodeling is a defining characteristic of emphysema, the SP-D (−/−) mouse is an ideal model for emphysema.

Example 6

Cytokines, Hydrogen Peroxide Production, and Metalloproteinase Activities

Methods

Cytokine Measurements

Lung homogenates from 6 to 9 week-old mice were centrifuged at 2000 RPM and stored at −20° C. Tumor necrosis factor alpha (TNF-α), interleukin (IL)-1β, IL-6, and macrophage inflammatory protein (MIP)-2 were quantitated using murine sandwich ELISA kits (R&D Systems, Minneapolis, Minn.) according to the manufacturer's directions. All plates were read on a microplate reader (Molecular Devices, Menlo Park, Calif.) and analyzed with the use of a computer-assisted analysis program (Softmax; Molecular Devices). Only assays having standard curves with a calculated regression line value of >0.95 were accepted for analysis.

Hydrogen Peroxide Production

Alveolar macrophages were collected by bronchoalveolar lavage with 1 ml of dye-free RPMI media (Gibco, Grand Island, N.Y.) times three. Bronchoalveolar lavage fluid (BALF) from 8-10 mice was pooled to provide sufficient numbers of macrophages for analysis. The lavage was centrifuged at 1200 RPM for 10 minutes and one million macrophages were resuspended in PBS. Hydrogen peroxide production by macrophages was measured using a commercially available assay (Bioxytech $H_2O_2$-560 assay, OXIS International, Portland, Oreg.), based on the oxidation of ferrous ions ($Fe^{2+}$) to ferric ions ($Fe^{3+}$) by hydrogen peroxide under acidic conditions. Methods followed the manufacturer's recommendations. Hydrogen peroxide production was determined after activation with 100 ng/ml phorbol myristate acetate (PMA) or without stimulation.

Metalloproteinase Activity

Mouse lavage samples were centrifuged (100,000×g, 1 hour) in a SW-28 rotor (Beckman, Palo Alto, Calif.). The supernatants were concentrated using Centricon-30 filtration units (Amicon, Inc., Beverly, Mass.). Samples (200 μbprotein) were electrophoresed under nonreducing conditions (laemmli) into 10% Zymogram, gelatin and casein gels (Novex, San Diego, Calif.). Following electrophoresis, gels were washed twice with 2.5% Triton X-100 (37° C., 15 min.) and incubated for 16 hours with 40 mM Tris-HCl, pH 7.5, 10 mM $CaCl_2$, 1 uM $ZnCl_2$. Gels were stained with 0.5% (w/v) Coomassie Blue in 50% methanol, 10% acetic acid for 1 hour, then destained. Metalloproteinases were detected as clear bands against the blue background. Metalloproteinase 2 and 9 mRNA's were quantitated by Northern blot analyses of total lung mRNA from wild type and SP-D (−/−) mice using [$^{32}$P]-labeled cDNA probes (Chemicon International, Inc., Temecula, Calif.).

Results

Figure 3:
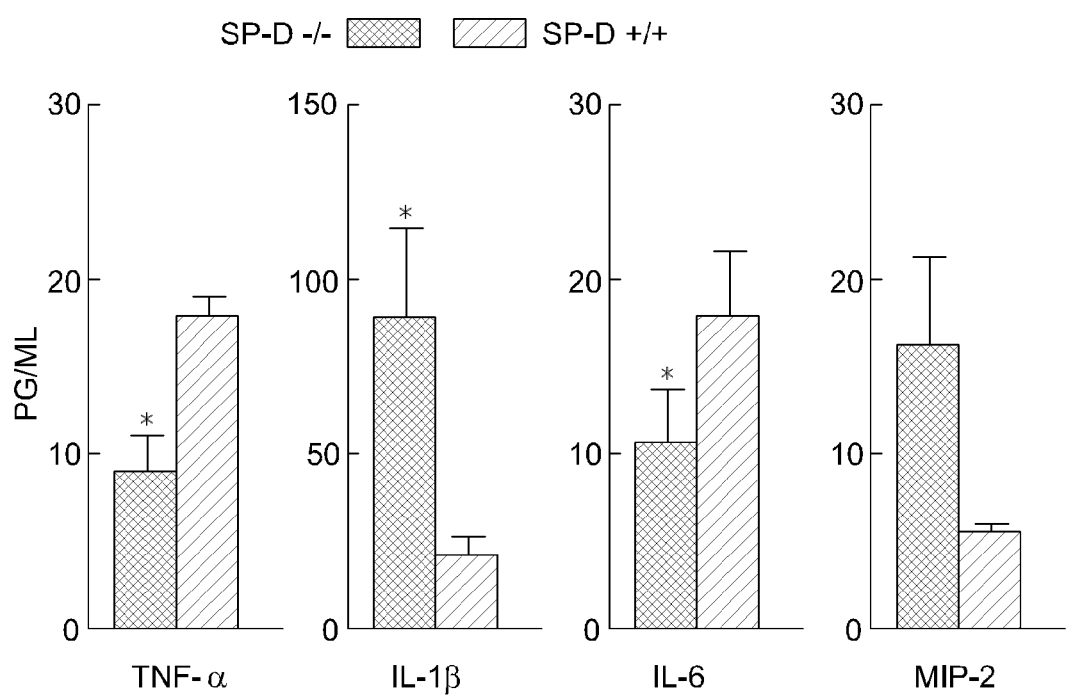
FIG. 3: Pro-inflammatory cytokines in lung homogenates from SP-D (−/−) mice. Concentrations of TNF-α, IL-1β, IL-6 and MIP-2 were assessed in lung homogenates from SP-D (−/−) (solid bar) and SP-D (+/+) (hatched bar) mice. Data are expressed as pg/ml and represent the mean±SE with n=5 mice per group; *$p<0.05$ compared to SP-D (+/+) mice.
Figure 4:
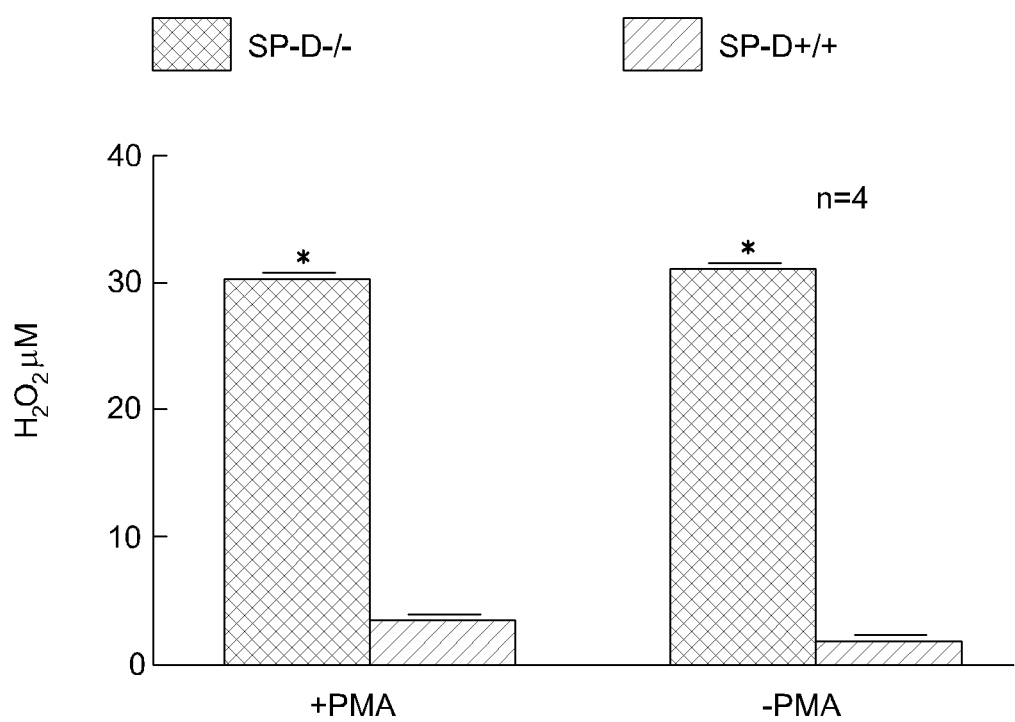
FIG. 4: Hydrogen peroxide production in alveolar macrophages from SP-D (−/−) (solid bar) was assessed from $1\times10^6$ macrophages isolated from bronchoalveolar lavage fluid (BALF) as compared to SP-D (+/+) mice (hatched bar) with and without PMA stimulation. Data are expressed as μM of $H_2O_2$ and represent the mean±SE with n=4 mice per group; *$p<0.05$ compared to SP-D (+/+) mice.

At 6 to 9 weeks of age, lung homogenates from SP-D (−/−) mice did not contain inflammatory levels of the pro-inflammatory cytokines TNF-α, IL-1β, IL-6 or MIP-2, although basal levels of IL-1β were increased significantly, FIG. 3. In contrast, oxidant production, as assessed by measuring hydrogen peroxide production by alveolar macrophages isolated from SP-D (−/−) mice, was increased 10 fold, FIG. 4. Hydrogen peroxide and superoxide production is a measure of macrophage activation, particularly the microbicidal activation. Since oxidant production has been associated with activation of a number of metalloproteinases and with emphysema in both human and animal studies, metalloproteinase activities were estimated by degradation of gelatin substrates after SDS-PAGE of BALF supernatants isolated from SP-D (−/−) and SP-D (+/+) mice. Bands of activity consistent with metalloproteinases −2 and −9 were readily detected in both genotypes, but were not altered in lung tissue from SP-D (−/−) mice. Likewise, the abundance of metalloproteinasese −2 and −9 mRNA's were similar in whole lung RNA samples from SP-D (−/−) and SP-D (+/+) mice as assessed by Northern blot analysis. However, production of MMP-2 and 9 by alveolar macrophages isolated from SP-D (−/−) mice were markedly increased. Likewise, immunostaining for MME (macrophage metalo-elastase) and MMP-9 were increased in the lungs of the SP-D (−/−) mice.

The results in Examples 1-6 were completely unexpected. There is nothing in the literature to suggest an SP-D null mouse is a model for emphysema.

In summary, the SP-D (−/−) mouse conclusively demonstrates a remarkable and surprising role for SP-D in regulation of surfactant homeostasis, the structure of alveolar surfactant in the lung, regulation of SP-A expression, or plays a critical inhibitory role in oxidant, hydrogen peroxide production in the lung. Therefore, its levels are important for suppression of ongoing oxidant production and injury and the regulation of alveolar remodeling and suppression of proteases that cause emphysema. This makes the SP-D (−/−) mouse an excellent model for emphysema. Example 7 will summarize the results for the mouse model of emphysema.

Example 7

SP-D (−/−) Mouse as a Model for Emphysema

SP-D deficiency caused inflammation, increased oxidant production by isolated alveolar macrophages, emphysema, and localized fibrosis in gene-inactivated SP-D (−/−) mice. The timing and progressive nature of these pulmonary abnormalities support the conclusion that alveolar enlargement in SP-D (−/−) mice is caused by alveolar remodeling associated with chronic inflammation, rather than with development abnormalities occurring during alveologenesis. The present findings are consistent with an important and unanticipated role of SP-D in the modulation of pulmonary inflammation and oxidant production and suggest that changes in the regulation or function SP-D may play a role in the pathologic processes leading emphysema following chronic lung injury.

Histologic and morphometric analyses of lungs from SP-D (−/−) mice revealed no abnormalities in lung structure until 3 weeks of postnatal age, one week after alveologenesis is completed in the mouse. This was consistent with the observation that the relative proportions of respiratory parenchyma and airspace were similar in both SP-D (−/−) and SP-D (+/+) mice between postnatal days 5 and 17. After 2 weeks of age, increased parenchymal-airspace ratios were observed in SP-D (−/−) mice, consistent with ongoing remodeling of the parenchyma and alveolar spaces. Enlarged airspaces were generally associated with focal accumulation of large, foamy, alveolar macrophages, although there was some heterogeneity in both localization and extent of inflammatory infiltrates and remodeling in older mice While focal accumulation of alveolar macrophages in lungs of SP-D (−/−) mice were observed as early as 2 weeks of age, macrophage morphology remained normal at this time. Abnormal alveolar macrophage morphology, consisting of enlarged foamy cells, was noted by 3 weeks of age and was coincident with enlargement of alveolar structures thereafter. Previous studies demonstrated increased numbers of enlarged alveolar macrophages in SP-D (−/−) mice by 8 weeks of age. Thus, the development of emphysema in SP-D (−/−) mice is consistent with the temporal and spatial accumulation of activated macrophages, and increased production of proteases MMP-2, 9 and MME, suggesting their role in the remodeling process. The present findings do not support a role for SP-D in normal long morphogenesis and alveologenesis, a process generally completed by approximately 2 weeks of postnatal age in mice.

The present findings do support an important role for SP-D in the modulation of alveolar macrophage activation and oxidant production, leading to protease activation, emphysema and fibrosis. Macrophage infiltration and lung remodeling in SP-D (−/−) mice were associated with modest but significant differences in inflammatory levels of various pro-inflammatory mediators, including IL-1b, MIP-2, but not TNF-α and IL-6, but rather with markedly increased hydrogen peroxide production by isolated alveolar macrophages. Although basal levels of IL-β1 were significantly increased in SP-D (−/−) mice, IL-β1 was not increased to levels typically detected in severe inflammation. While increased IL-1β and hydrogen peroxide production were observed in SP-D (−/−) mice, it remains unclear whether the pulmonary abnormalities seen in these mice were directly mediated by cytokine or oxidant-induced injury. Although SP-D has been proposed to play an important role in host defense, there was no histologic or serologic evidence of infection in the SP-D (−/−) colony.

Enhanced hydrogen peroxide production and increased numbers of alveolar macrophages found in the lungs of SP-D (−/−) mice support the concept that SP-D plays a critical anti-inflammatory role in the lung and regulates hydrogen peroxide production by alveolar macrophages in vivo. Relationships between oxidant injury and the development of emphysema and pulmonary fibrosis are well established in numerous animal and genetic models. For example, neonatal exposure to hyperoxia caused alveolar remodeling and fibrosis in newborn mice. Since activation of metalloproteinases has been associated with oxidant injury and emphysema, metalloproteinase activities were assessed in BALF from the SP-D (−/−) mice. While protease activity consistent with metalloproteinase −2 and −9 were readily detected by zymography in lung homogenates, but, no consistent changes in the activities of these proteinases or their mRNAs were detected in SP-D (−/−) mice. However, markedly increased production of MMP-2 and MMP-9 were demonstrated in isolated alveolar macrophages from SP-D (−/−) mice in vitro and immunostaining for MME and MMP-2 were increased in the lungs of SP-D (−/−) mice in vivo. Thus, localized increased concentrations of metalloproteinases and/or alterations in other proteases or antiproteases is associated with SP-D deficiency. Deficiencies in antiproteases, as well as smoking and oxidant injury from oxidizing toxicants (e.g., bleomycin or paraquat), have all been associated with emphysema or pulmonary fibrosis in human lung.

While surfactant phospholipid content was increased in SP-D (−/−) mice and was associated with increased numbers of large, foamy, alveolar macrophages, increased phospholipid content alone is not likely to be sufficient to cause the alveolar remodeling observed in SP-D (−/−) mice. In fact, the overall effect of surfactant phospholipids appears to be anti-inflammatory, altering phagocytosis, oxidant production, and cytokine release, and inhibiting lymphocyte proliferation, immunoglobulin production, and expression of adhesion molecules. On the other hand, transgenic mice in which GM-CSF was over-expressed in the respiratory epithelium had markedly increased numbers of normal appearing alveolar macrophages, but did not develop pulmonary alveolar proteinosis/lipoidosis, emphysema, or fibrosis. In contrast, surfactant phospholipids and proteins were markedly increased in lungs from both GM-CSF (−/−) and GM-receptor common beta subunit (βc) deficient mice in association with alveolar macrophage accumulation and perivascular/peribronchiolar monocyte infiltrates; however, neither model of pulmonary alveolar proteinosis/lipoidosis was associated with emphysema or fibrosis. Likewise, transgenic mice over-expressing IL-4 in the lung also exhibited increased amounts of surfactant protein and lipids, as well as increased numbers of inflammatory cells, but did not develop emphysema.

Although concentrations of SP-D in the lung change during development, increasing with advancing age, SP-D levels are also influenced by various clinical conditions. Recent studies demonstrated marked reduction of SP-D concentrations in BALF obtained from patients with cystic fibrosis (CF), supporting a potential role for SP-D in the pathogenesis of the chronic inflammation associated with CF lung disease. SP-D levels were also reduced in BALF of smokers, suggesting that decreased levels of SP-D may contribute to later development of chronic obstructive pulmonary disease (COPD) and emphysema in these patients. Although concentrations of SP-D in BALF were increased in patients with pulmonary alveolar proteinosis (PAP), patients with idiopathic pulmonary fibrosis (IPF) and interstitial pneumonia associated with collagen vascular disease (IPCD) had decreased BALF levels of SP-D. On the other hand, serum concentrations of SP-D were increased in patients with PAP, IPF, and IPCD; although serum levels of both SP-A and SP-D varied with the severity of IPF and during the course of anti-inflammatory therapies. These clinical findings, as well as the present study, demonstrating that SP-D is involved in the maintenance of normal lung architecture and suppression of oxidant production, support the concept that changes in SP-D concentrations may be involved in the pathogenesis of lung injury associated with various clinical conditions, including oxidant injury, lung abscesses, secondary diseases, cystic fibrosis, interstitial pulmonary fibrosis (IPF), and chronic obstructive pulmonary disease (COPD), various lung infections, respiratory distress syndrome (RDS), bronchopulmonary dysplasia (BPD), chemotherapy-induced lung injury, lung fibrosis secondary to primary abscess (ie: sarcoid), and asthma.

In previous studies, abnormalities were not seen in alveolar macrophages or lung morphology were observed in the heterozygous SP-D (+/−) mice, demonstrating that a 50% reduction in SP-D concentration in BALF is not sufficient to cause pulmonary abnormalities. The precise concentrations of SP-D that inhibit oxidant-induced injury and lung remodeling are unclear at present. Whether further injury or oxidant stress to the lungs of SP-D (+/−) or SP-D (−/−) mice will exacerbate emphysema and fibrosis in this animal model remains to be determined.

The modest reduction of lung SP-A concentrations found in SP-D (−/−) mice is not likely to contribute to the changes in lung morphology observed in these mice, since neither SP-A (+/−) nor SP-A (−/−) mice developed emphysema. Furthermore, lung morphology of SP-A deficient mice was normal, and, in contrast to SP-D (−/−) mice, SP-A deficiency was associated with decreased hydrogen peroxide production by isolated alveolar macrophages.

SP-D (−/−) mice developed severe and progressive emphysema. Alveolar remodeling and macrophage abnormalities were apparent as early as 3 weeks of age, while mild, focal, pulmonary fibrosis was observed at 6 to 7 months of age, demonstrating a role for SP-D in the regulation of inflammation and alveolar remodeling. The present study also demonstrated an unexpected role for SP-D in the regulation of hydrogen peroxide production and metalloprotease production by alveolar macrophages in vivo, which may contribute to the development of emphysema in the lungs of SP-D (−/−) mice. Whether SP-D deficiency contributes to ongoing inflammation or to the development of emphysema and fibrosis found in various human chronic lung diseases, including those caused by smoking and other oxidants, remains to be determined.

Testing Therapies in the Mouse Model

Because of the lack of pharmaceutical therapies for the treatment of emphysema, a model for testing possible therapies is imperative. The SP-D (−/−) mouse provides that model. Therefore, Example 6 provides a sample framework for testing pharmaceuticals, protein preparations, or genetic manipulations for the treatment of emphysema.

Example 8

A number of doses or concentrations of protein or pharmaceutical diluted in an appropriate buffer is administered to SP-D (−/−) mice intratracheally. Protein and pharmaceutical is purified as appropriate for in vivo use. Recombinant adenovirus or other genetic vectors containing the gene of interest is administered as follows. SP-D (−/−) mice are immunosuppressed to block specifically T cell-mediated immune responses, and treated with an adenoviral construct designed to express the gene of interest in transduced cells. Mice are injected intraperitoneally with H57 antibody 3 days prior to receiving the adenoviral construct. H57 alters immune recognition at the T cell receptor and decreases splenic and lung T and B lymphocytes. One dose is instilled intratracheally and another group is treated intraperitoneally with H57 followed by intratracheal administration of vehicle alone. Levels of the protein of interest is measured 1 week after administration to detect uptake and expression of the vector. Four mice are tested and untreated SP-D (−/−) mice are used as a control. Intratracheal inoculation involves anesthetizing with isofluorane, and an anterior midline incision is made to expose the trachea. A 30-gauge needle attached to a tuberculin syringe is inserted into the trachea, and a 100-μl inoculum of protein or pharmaceutical is dispersed into the lungs. The incision is closed with one drop of Nexaband. Nonpyogenic PBS is injected intratracheally as a control.

To test for efficacy of the protein, pharmaceutical, or genetic manipulation at diminishing the effects of emphysema, a number of tests are performed.

To determine the effects of the protein or pharmaceutical on the lung structure lungs are inflation fixed and sections evaluated by electron microscopy. Lungs from treated and untreated mice are inflated via a tracheal cannula at 20 cm of pressure with 4% paraformaldehyde and removed en bloc from the thorax. Lungs are dehydrated and embedded in paraffin. Tissue sections (5 μm) are stained with hematoxylin and eosin.

To test the number and morphology of macrophages: Staining with Nile Red detects vesicles and staining with Nile Blue and exciting with 520-550 mm green light is an additional method to detect lipid or phospholipid. Macrophage number is determined by staining with anti MAC-1 or other macrophage specific antiserum. Macrophage size is estimated from the diameter of fixed and stained macrophages from cytospin preparations sedimented onto glass slides at 1500×g for 2 min.

Surfactant composition and ultrastructure is analyzed as follows: The structure of surfactant is analyzed by isolating large aggregates from pooled alveolar lavage of SP-D (−/−) treated and untreated mice and examined by EM (see protocol below). For alveolar lavage phospholipid composition analysis, two to four samples consisting of the pooled lavage from two to three mice are evaluated for the relative abundance of phosphatidylcholine, phosphatidylethanolamine, phosphatidylglycerol, phosphatidylinositol, sphingomyelin, and lysobis-phosphatidic acid. Incorporation of ($^3$H)choline into total lung Sat-PC is evaluated to determine total phospholipid concentration Aggregate forms from alveolar lavage. Surfactant in alveolar was can be separated into large aggregate (heavy, dense) and small aggregate (light, visicular) fractions by centrifugation. Alveolar washes were centrifuged at 40,000×g over 0.8 M sucrose cushion for 15 min. The large aggregate surfactant then was collected from the interface, diluted with normal saline and centrifuged again at 40,000×g for 15 min. The supernatant from the first 40,000×g centrifugation that contains small aggregate surfactant is concentrated at 4° C. by ultrafiltration using a 300,000 molecular weight retention filter (Minitan, Miliore Corp., Bedford, Mass.) or centrifugal concentrators (Amicon Corp., Danvers, Mass.). The small aggregate surfactant is diluted with 50 ml normal saline and ultrafiltered 3 times to remove soluble proteins.

SP-D as a Treatment for Pulmonary Diseases

Because deletion of SP-D produced the mouse model for emphysema, SP-D is an obvious choice as a treatment for or prevention of emphysema. It is also an obvious treatment for other types of pulmonary disease since many of these diseases are characterized by aberrant surfactant production. In addition, its affect on SP-A and its possible role in host defense makes it a useful tool to augment immune function in the lungs. The feasibility of gene transfer to the respiratory epithelium is very promising as a treatment for various pulmonary diseases. A variety of viral and non-viral-based vectors have been developed to transfer genes to cells of the airways, including recombinant adenoviral vectors. These vectors are particularly promising for use in respiratory treatment because they have the potential of being aerosolized. Therefore, Example 9 is an experiment using purified mouse SP-D protein for treatment of emphysema in SP-D(−/−) mice. Example 10 is an experiment using adenovirus to express rat SP-D for treatment of emphysema in SP-D(−/−) mice. Example 11 provides a sample framework for the use of SP-D peptide, or vectors expressing SP-D for the prevention and treatment of these diseases. Emphysema is used as an exemplary pulmonary disease. Adenovirus is used as an exemplary vector.

Example 9

Treatment with Purified SP-D

Figure 12:
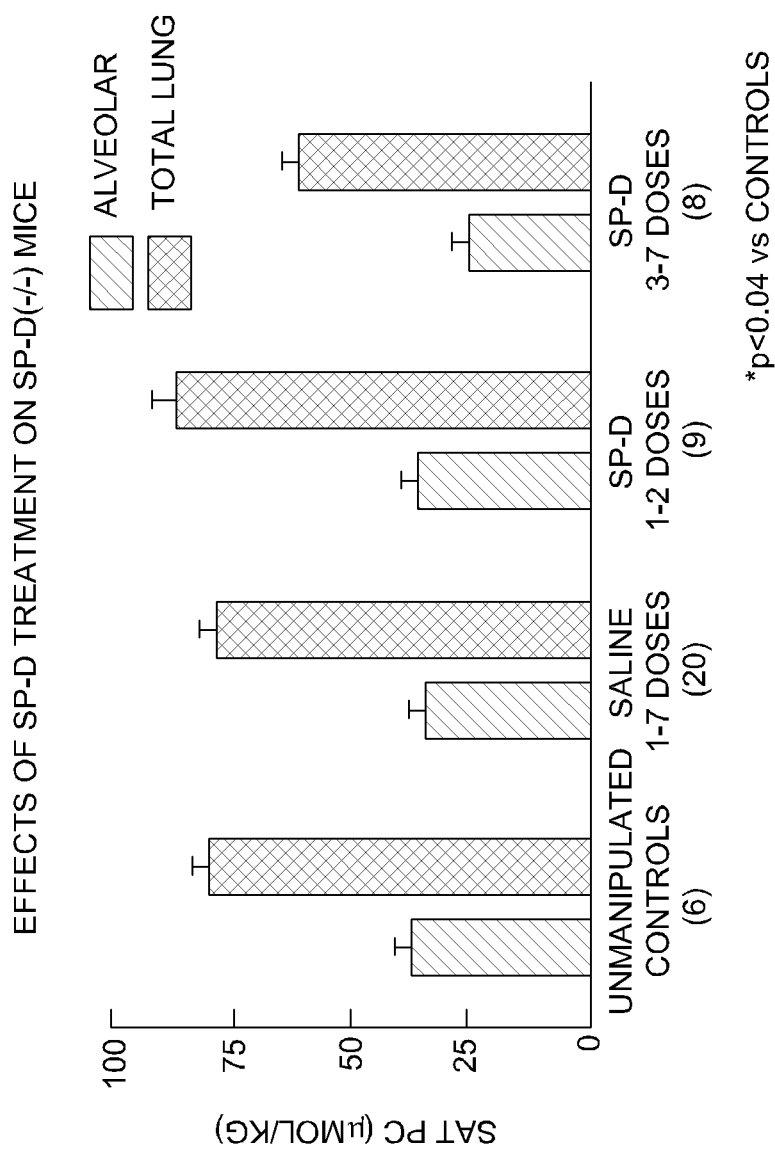
FIG. 12: Effects of SP-D protein treatment on SP-D (−/−) mice.

SP-D(−/−) mice were treated with purified mouse SP-D, purified as outlined below. Saturated PC levels were analyzed in alveolar lavage and total lung lavage. Repeated doses intratracheally at 24 hour intervals resulted in partial correction of lipid accumulation after 3 to 7 doses, see FIG. 12.

Figure 13A:
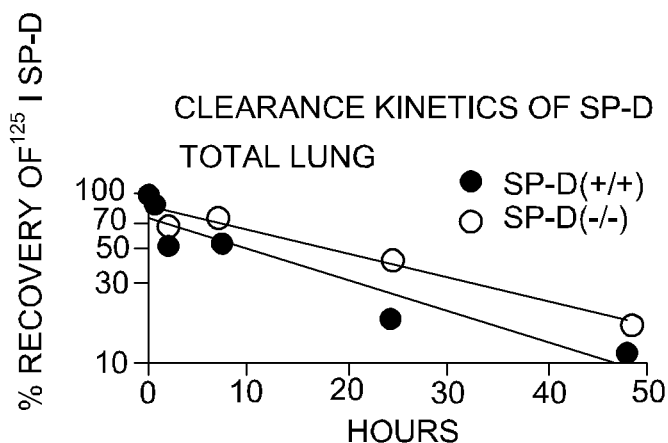
FIGS. 13A and 13B depict either Total lung or alveolar lavage clearance kinetics of SP-D protein in mice, respectively.
Figure 13B:
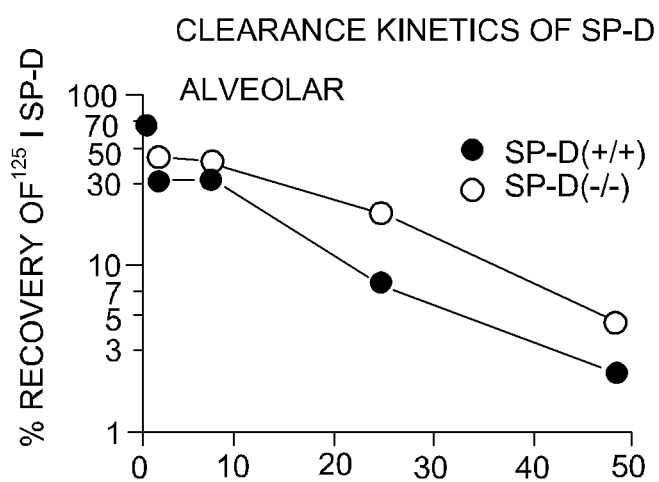

The half life of SP-D in the airway was determined as 13 hours in mouse (see FIGS. 13A and 13B) (the technique is outlined below); therefore, the SP-D deficiency can be treated by replacement of SP-D protein at a reasonable interval by aerosol or particulate inhaler or surfactant mixtures.

Purification of Mouse SP-D

Mouse bronchoalveolar lavage (BAL) fluid from GMCSF and SP-A double null mutant mice was collected, frozen, and pooled for later purification of SP-D. Maltosyl-agarose (Sigma) was packed in a gravity flow column (10×80 mm) and equilibrated with buffer containing 20 mM Tris-HCl, pH 7.4, 10 mM calcium chloride, 0.02% (W/V) sodium azide (TCB). The BAL was made 20 mM with respect to Tris-HCl, and 10 mM with respect to EDTA, ph 7.4 and stirred for one hour at room temperature. The turbid solution was centrifuged at 10,000×g for 40 minutes at 4° C. The supernatant was made 20 mM with respect to calcium chloride and readjusted to pH 7.4 before loading on the maltosyl-agarose column. The column was washed to background absorbence with TCB followed by washing with TCB containing 1.0 M Sodium Chloride. The SP-D, which has a specific requirement for calcium in binding to maltose was eluted with 50 mM manganese chloride, 20 mM Tris-HCl, 0.02% (W/V) sodium azide, pH 7.4. The fractions containing SP-D were determined by SDS polyacrylamide gel electrophoresis or by direct ELISA, pooled, and dialysed against three changes of 20 mM Tris-HCl, 100 mM sodium Chloride, 5 mM EDTA pH 7.4. This protocol was adapted from Strong, Peter; Kishore, Uday; Morgan, Cliff; Bernal, Andres Lopez; Singh, Mamta; and Reid, Kenneth B. M.; Journal of Immunological Methods 220 (1998) 139-149.

Treatment of mice with surfactant components. A technique for oral blind intubation with 26 g feeding tubes in mice under anesthesia with isoflurane was used for repetitively treating mice with SP-D daily for up to 7 days without problems. This approach avoids surgery and permits the type of experiments proposed for SP-D replacement and treatment with mutant SP-D proteins.

Figure 14:
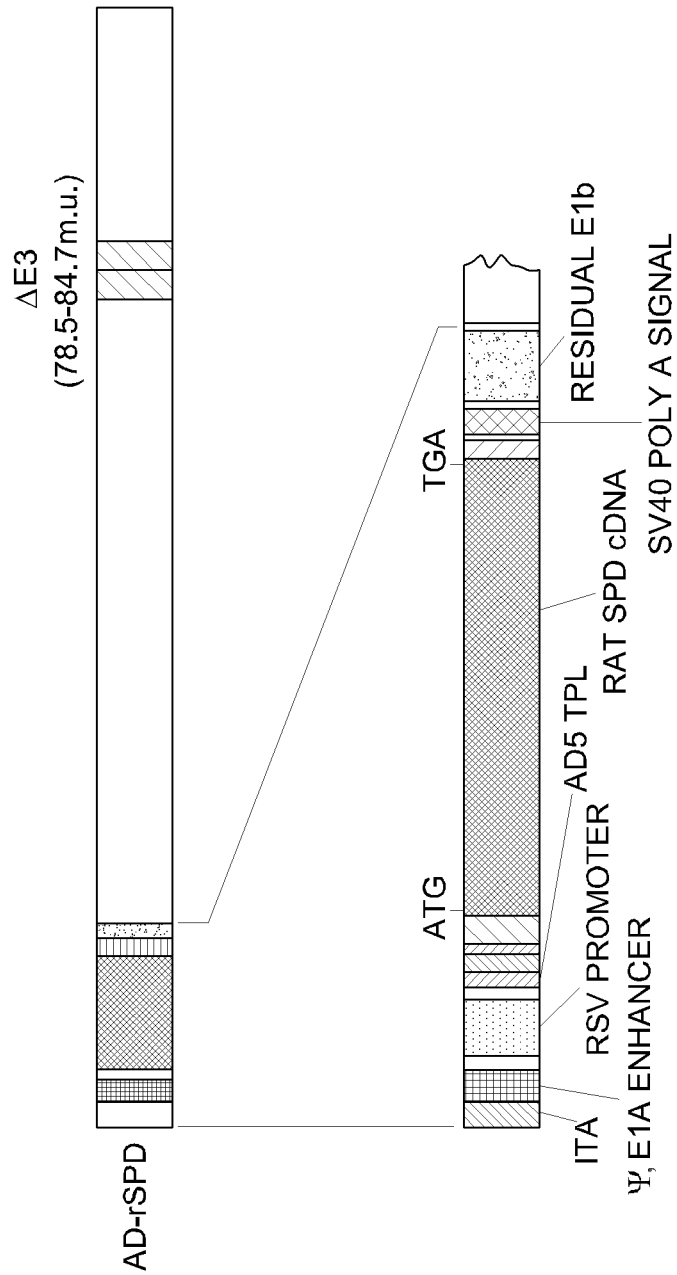
FIG. 14: Adenoviral vector Ad-rSPD containing rat SP-D cDNA.

Initially SP-D(−/−) mice were treated with purified mouse SP-D by tracheal instillation. Three or more doses of 2.9 μg SP-D given at 24 hour intervals decreased both alveolar and saturated PC pools (see FIG. 14). This dose of SP-D given is approximately the amount present in the endogenous pool in SP-D(+/+) mice. Given the lung association and clearance kinetics, this is a low dose. Thus, exogenous administration of SP-D directly influences surfactant lipid metabolism and provides an experimental model in which the function of modified SP-D molecules can be tested in vivo.

Biological half-life protocol: The biological half-life of SP-D in mice was measured in order to design experiments for treatment with SP-D. Iodinated purified mouse SP-D was generated with $^{125}I$ using the Bolton-Hunter reagent as previously performed for SP-A and the other surfactant proteins. The clearance of SP-D from alveolar lavages of SP-D(+/+) and SP-D (−/−) mice was similar with a half life of about 13 hours (see FIGS. 13A and 13B). The $t^{1/2}$ of 17 h for SP-D in the lungs of SP-D(−/−) mice was somewhat longer than the $t^{1/2}$ of 13 hours for SP-D(+/+) mice.

GM-CSF deficiency causes a 48 fold increase in SP-D, and the GM-CSF (−/−)×SP-A(−/−) cross has similarly elevated SP-D but no SP-A. SP-D was isolated from alveolar washes from GM-CSF(−/−)×SP-A (−/−) mice in high purity and in large amounts by the methods described by Persson et al. using an affinity column of mannose-Sepharose 6B in the presence of $Ca^{2+}$.

Example 10

Treatment with SP-D Expressed from an Adenovirus

We made a new adenovirus expressing rat SP-D. The virus produces SP-D in cells and in the lungs of normal or SP-D deficient mice. Western blots were performed for the rat SP-D produced in 293 cells and in mice.

Construction of Ad-rSPD adenovirus (see FIG. 14) Wild type rat SPD cDNA was liberated from plasmid WT-rSPD/pG3Z with EcoR I digestion and the 3' ends filled in with Klenow. The 1.3 kB rSPD cDNA was inserted into the EcoR V site of plasmid pAvS6a to make plasmid pAvS6a-rSPD. Plasmid pAvS6a-rSPD has a RSV promoter, a rSPC cDNA, an SV40 poly A signal and an Ad5 sequence (9.24-17.34 mu). Not I linearized pAvS6a-rSPD was co-transfected into 293 cells with Cla I digested large fragment of adenoviral DNA Ad dl327, which has E3 region (78.5-84.7 mu) deleted. After homologous recombination, individual plaques were analyzed by Western blot assay to determine rSPD protein expression. One rSPD positive clone was subject to one round of plaque purification. The Ad-rSPD adenovirus has deletions in E1 and E3 regions and is replication deficient. After amplification in 293 cells, the purified Ad-rSPD adenovirus was produced through two rounds of CsCl gradient ultracentrifugation. The adenovirus expressed SP-D and therefore could be used to restore pulmonary abnormalities by intratracheal administration. Therefore, this remains a very positive possibility for treatment of emphysema and many other SP-D deficiency illnesses as well as various other forms of pulmonary injury and deficiency.

Example 11

Treatment with SP-D Expressed from Other Vectors, Proteins, or Pharmaceuticals

The temporal, spatial and stoichiometric parameters for SP-D in that allow for restoration of phospholipid homeostasis were determined in Example 9. Initial studies to determine the kinetics of clearance of SP-D were performed with $^{125}$I labeled SP-D administered intratracheally; half-life was calculated and the information used in design of SP-D replacement experiments. The dose of SP-D that achieves normal physiologic concentrations of SP-D after administration was clarified.

Administration of purified SP-D protein was used to treat various pulmonary disease in Example 9. However, physiologic abnormalities in pulmonary disease may require long term correction of SP-D in the lungs. Therefore, recombinant adenovirus or other genetic vectors containing the mammalian SP-D gene will be used (see Example 10 and 11). Recombinant adenovirus vectors or Clara cell secretory protein (CCSP) and SP-C promoters can be used to selectively express SP-D in bronchiolar (Clara cell) and alveolar (Type II cell) compartments (see Example 10). Three days prior to treatment with adenoviral vector the mice are immunosuppressed by injection intraperitoneally with 200 ug of monoclonal anti-T cell receptor antibody, H57. Adenovirus was administered by intratracheal injection of 5×10$^8$ PFU of virus. Levels of SP-D protein were measured 1 week after administration to detect uptake and expression of the vector. Four mice were tested and SP-D (−/−) mice receiving no treatment are used as a control. To test for efficacy of the SP-D at diminishing the effects of emphysema, a number of tests are performed as follows.

To determine the effects of a protein or pharmaceutical on the lung structure (Example 11), lungs are inflation fixed and sections evaluated by electron microscopy. Lungs are inflated via a tracheal cannula at 20 cm of pressure with 4% paraformaldehyde and removed en bloc from the thorax. Lungs are dehydrated and embedded in paraffin. Tissue sections (5 μm) are stained with hematoxylin and eosin.

Number and morphology of macrophages are analyzed. Staining with Nile Red detects vesicles and staining with Nile Blue and exciting with 520-550 mm green light is an additional method to detect lipid or phospholipid. Macrophage number is determined by direct counting or macrophage cell surface markers. Macrophage size is estimated from the diameter of fixed and stained macrophages from cytospin preparations sedimented onto glass slides at 1500×g for 2 min.

Surfactant composition and ultrastructure are analyzed as follows: the structure of surfactant is analyzed by isolating large aggregates from pooled alveolar lavage of SP-D (−/−) treated and untreated mice and examined by EM. For alveolar lavage phospholipid composition analysis, two to four samples consisting of the pooled lavage from two to three mice are evaluated for the relative abundance of phosphatidylcholine, phosphatidylethanolamine, phosphatidylglycerol, phosphatidylinositol, sphingomyelin, and lyso-bis-phosphatidic acid. Incorporation of ($^3$H)choline into total lung Sat-PC is evaluated to determine total phospholipid concentration.

Once efficacy of the treatment is determined, treatment can be tested on other appropriate mammals.

Involvement of SP-D in Pulmonary Infection

The role of SP-D and SP-A in host defense in the lungs has been repeatedly demonstrated. SP-A and SP-D have specific interactions with various microorganisms in vitro, modifying pulmonary inflammation in vitro by altering cytokine and free radical production. The role of SP-D in bacterial clearance and inflammatory response of the lung was evaluated in vivo using a mouse model of SP-D deficiency. SP-A-deficient mice are known to be more susceptible to infections. A number of in vitro studies have shown a possible role for SP-D in host defense in addition to its role in up-regulating SP-A. Examples 8-11 outline sample protocols for testing SP-D as a therapy in the, bacterially, or fungally infected SP-D (−/−) mice as well as in the SP-A (−/−) mice. Examples 12-14 are experiments showing the role of SP-D in the response to bacterial, fungal, and viral infection. Example 13 is an experiment showing the effect of infecting SP-D(−/−) mice with Respiratory Syncytial Virus.

Example 12

Clearance of Bacterial Agents from SP-D(−/−) Mice

Figure 8A:
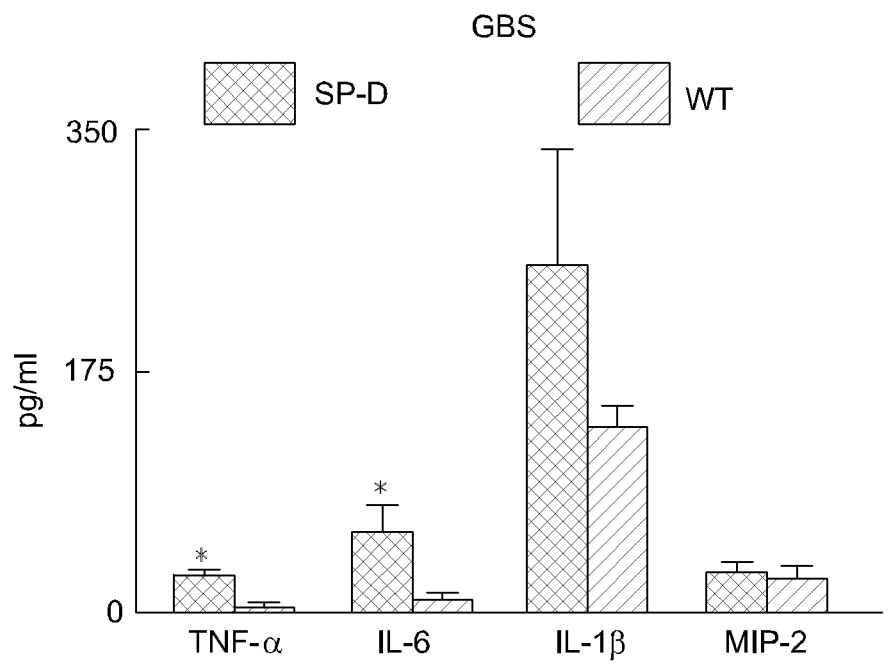
FIGS. 8A and 8B depict Cytokine levels in lung homogenates after infection with either GBS or *H. flu*, respectively.
Figure 8B:
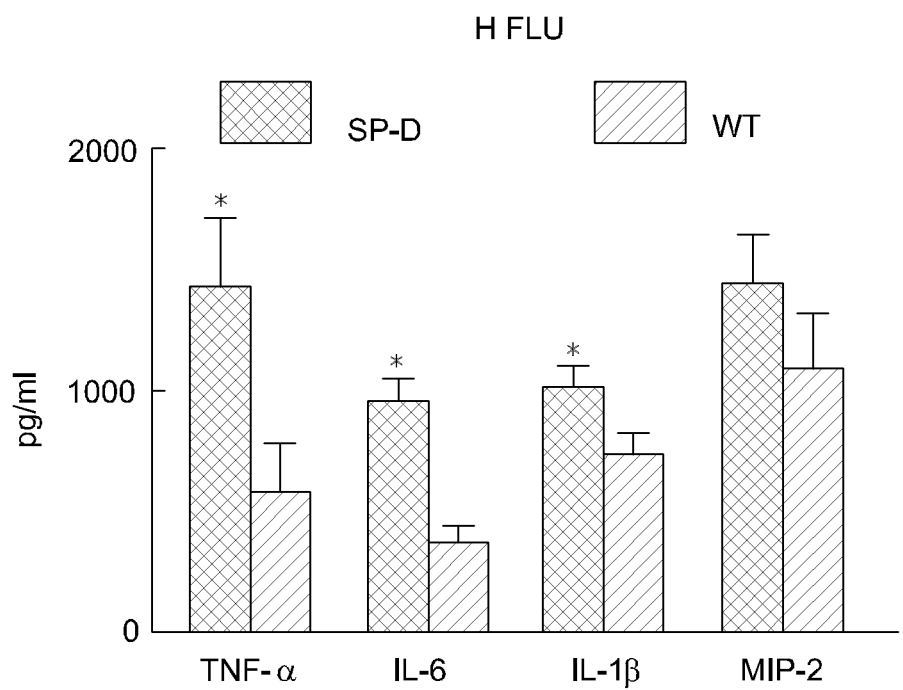
Figure 9A:
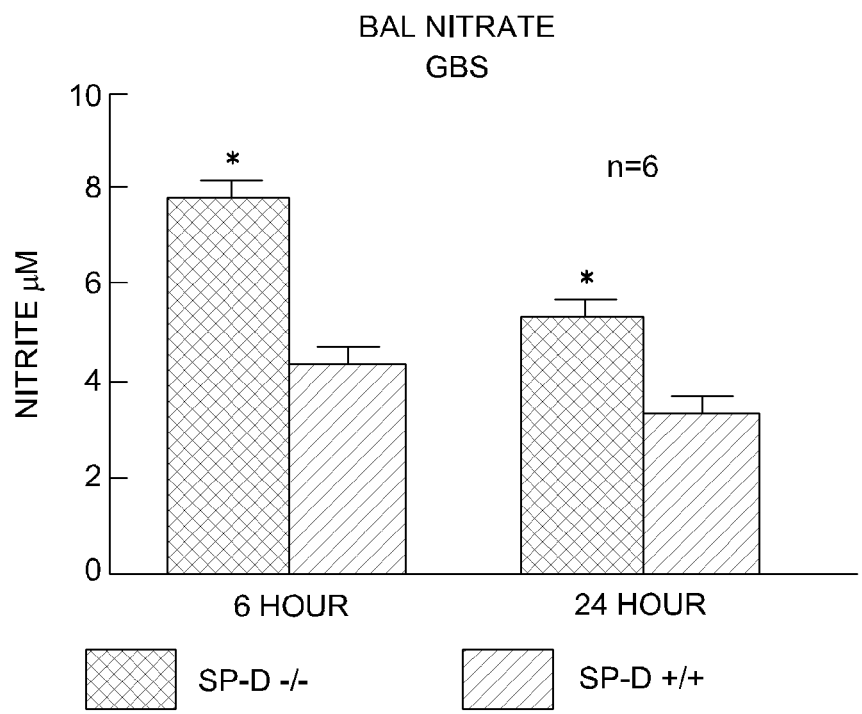
FIGS. 9A and 9B depict BAL nitrite levels after infection with either GBS or *H. flu*, respectively.
Figure 9B:
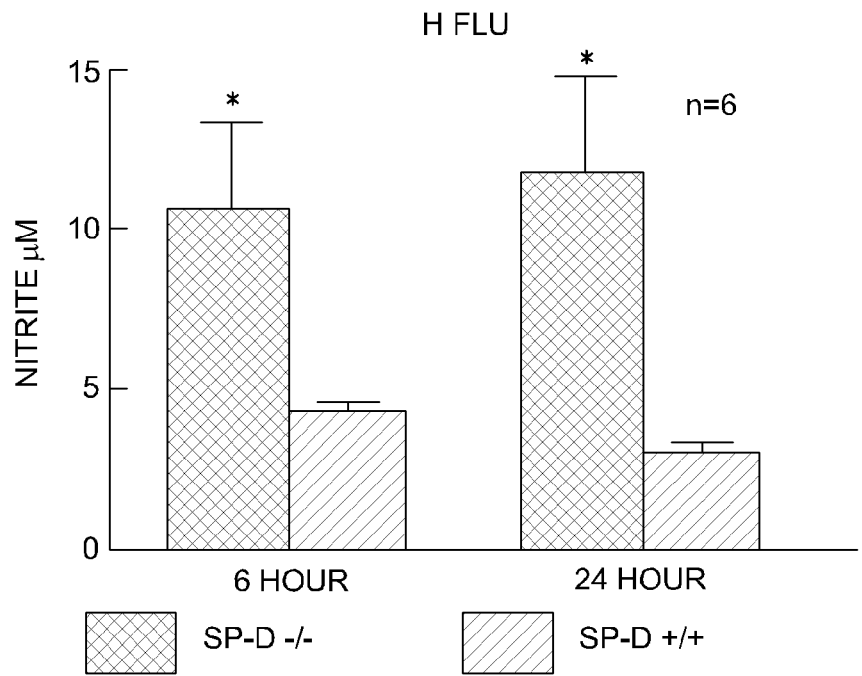

SP-D deficient mice (SP-D −/−) were intratracheally infected with Group B *streptococcus* (GBS) or *Hemophilus influenzae* (*H. flu*) to assess clearance compared to wild type mice. Group B *Streptococcus* was administered at 10$^4$ CFU. Pulmonary inflammation was also assessed by analysis of BAL fluid for total cells (FIGS. 5, 6, and 7A, 7B), cytokine levels in lung homogenates (FIGS. 8A and 8B), oxygen radical production by alveolar macrophages (FIGS. 11A and 11B) and nitrite levels in BAL (FIGS. 9A and 9B).

Figure 5:
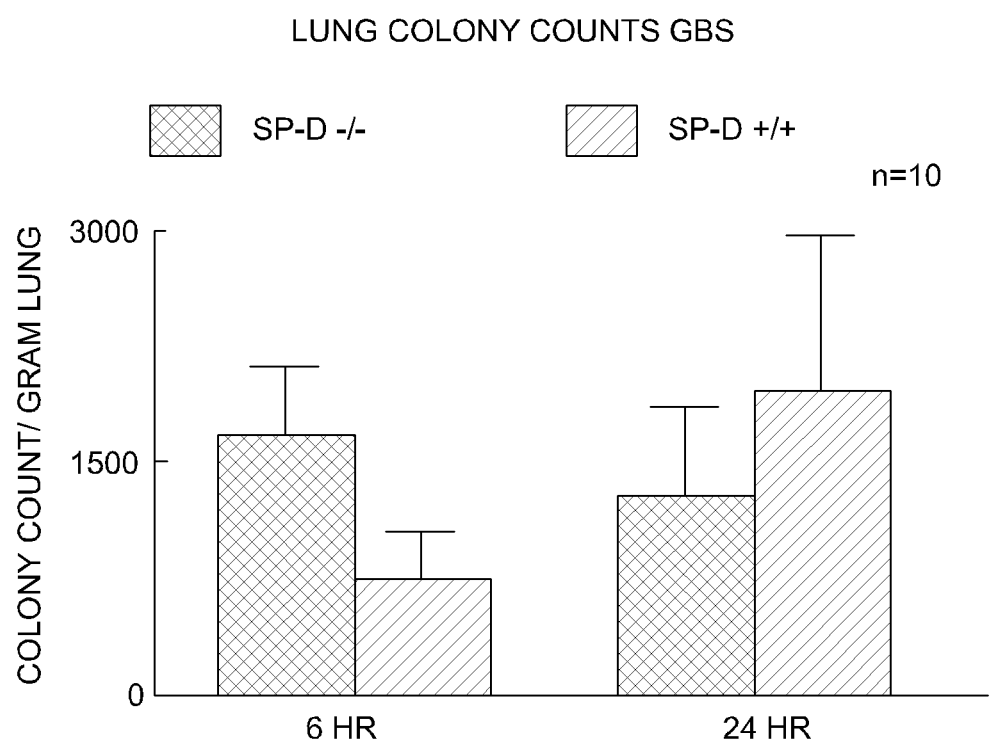
FIG. 5: Lung colony counts in SP-D(−/−) and SP-D(+/+) mice after infection with Gp B Streptococcus (GBS).
Figure 6:
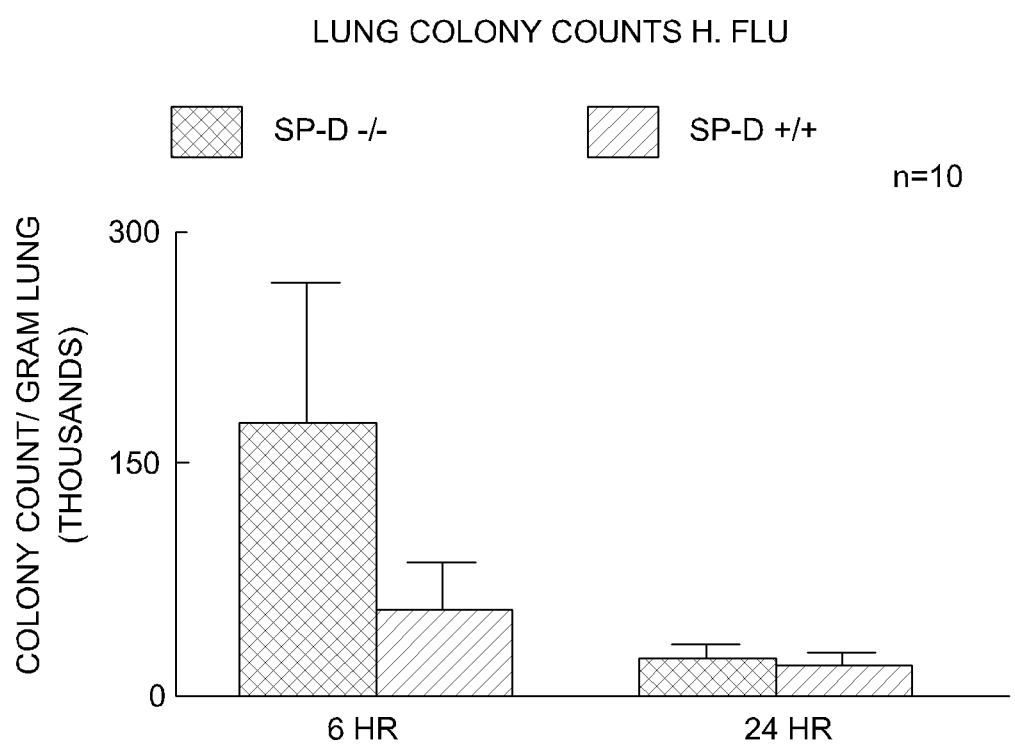
FIG. 6: Lung colony counts in SP-D(−/−) and SP-D(+/+) mice after infection with *Haemophilus influenzae* (*H. flu*).
Figure 7A:
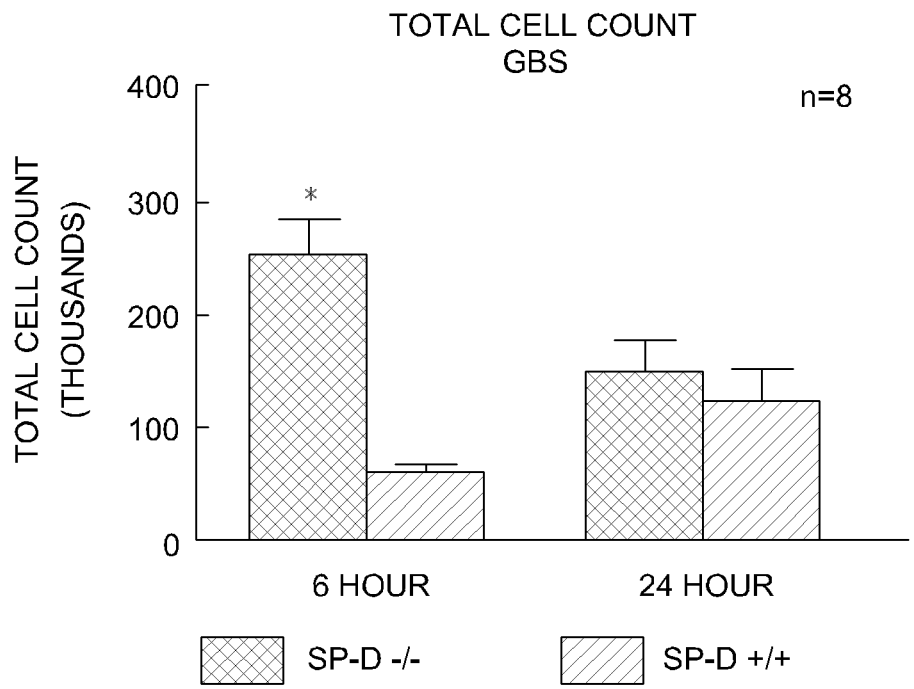
FIGS. 7A and 7B depict Total cell count in bronchoalveolar lavage (BAL) fluid after infection with either GBS or *H. flu*, respectively.
Figure 7B:
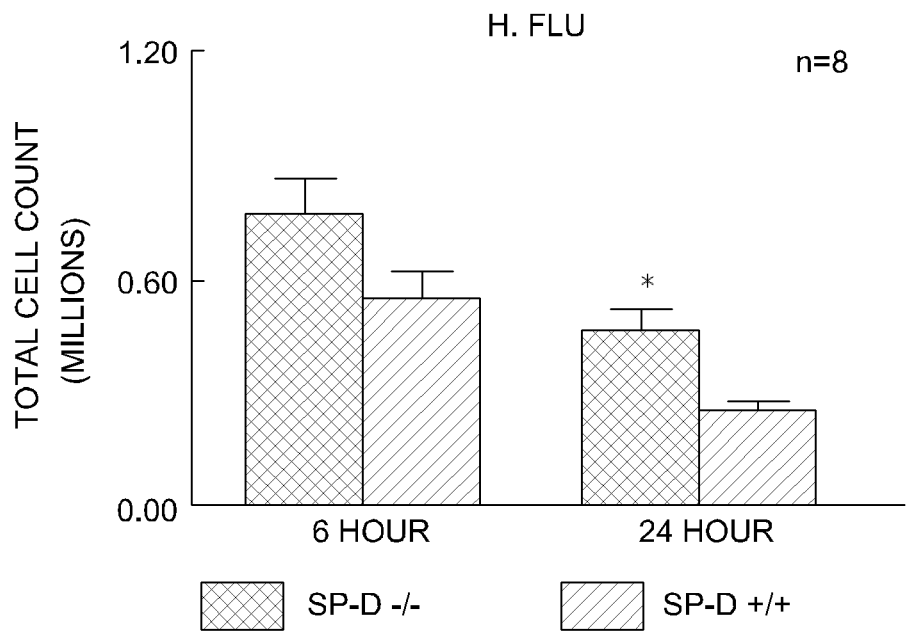
Figure 11A:
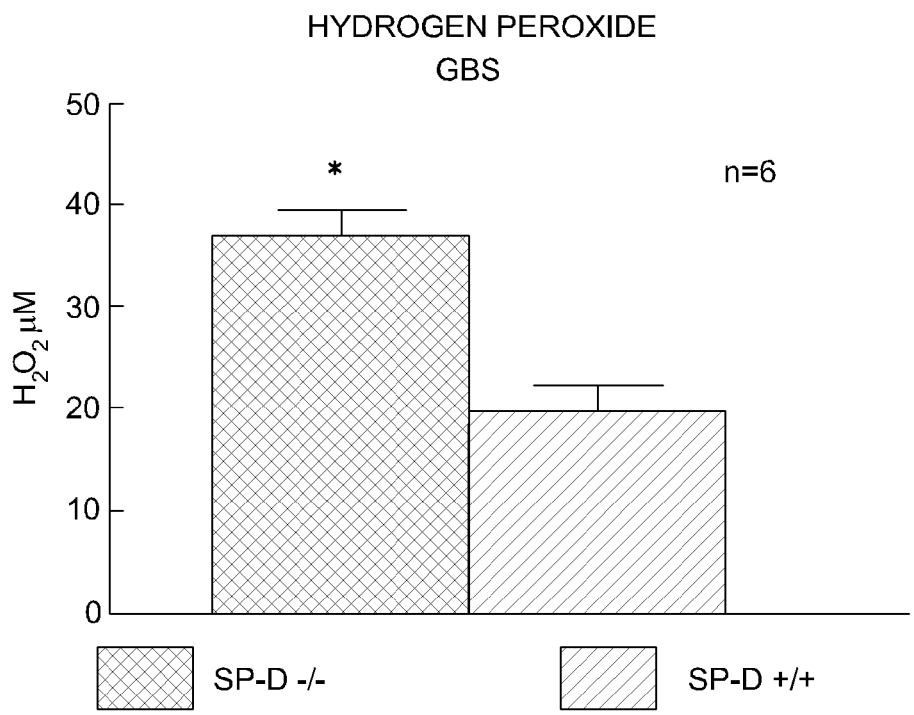
FIGS. 11A and 11B depict Hydrogen peroxide or superoxide levels in macrophages isolated from BAL after infection with GBS, respectively.
Figure 11B:
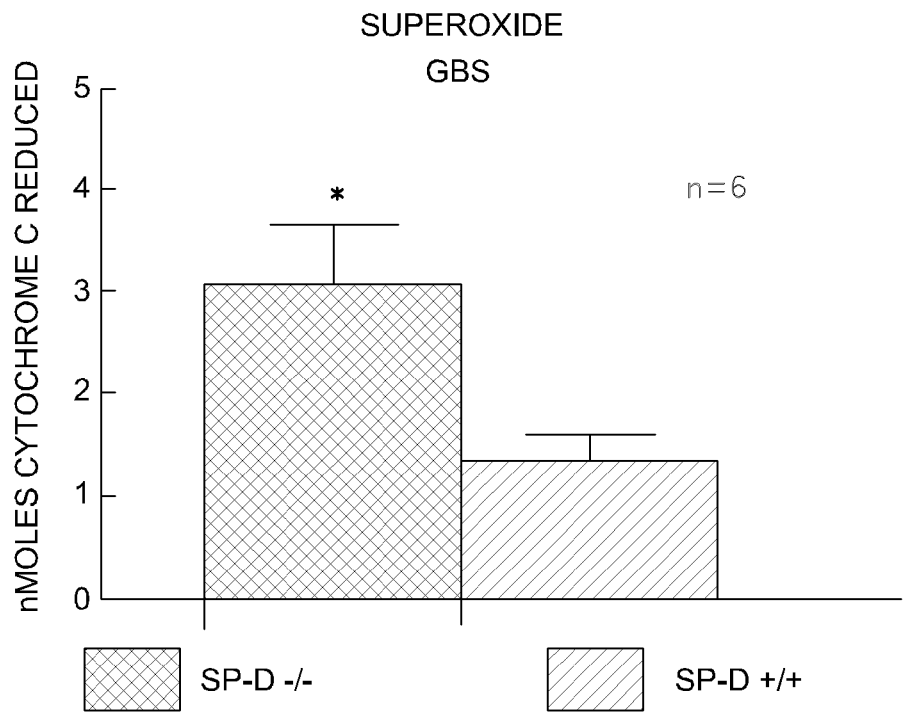

SP-D −/− mice cleared the bacteria similarly to wild type mice (see FIGS. 5 and 6). Infection with GBS and *H. flu* resulted in significantly greater total cells in the BAL fluid of the SP-D −/− mice compared to wild type mice (FIGS. 7A and 7B). Selective alterations of cytokine levels were detected in SP-D −/− mice. Tumor necrosis factor cc (TNF-α) and interleukin (IL)-6 levels were greater in lung homogenates from SP-D −/− mice early after infection with GBS or *H. flu* (FIGS. 8A and 8B). Macrophage inflammatory protein-2 (MIP-2), a neutrophil chemoattractant, was significantly greater in lung homogenates from SP-A −/− mice after *H. flu* but not GBS infection (FIGS. 8A and 8B). Macrophages from SP-D −/− mice generated significantly greater superoxide and hydrogen peroxide compared to wild type mice (FIGS. 11A and 11B).

BAL nitrite levels were increase in SP-D (−/−) mice as compared to wildtype mice. Nitric oxide production was measured as nitrite in BALF. Nitric oxide plays a role in host defense by contributing to bacterial killing. Nitric oxide reacts with superoxide to form peroxynitrite which is a potent bacteriocidal agent.

Figure 10A:
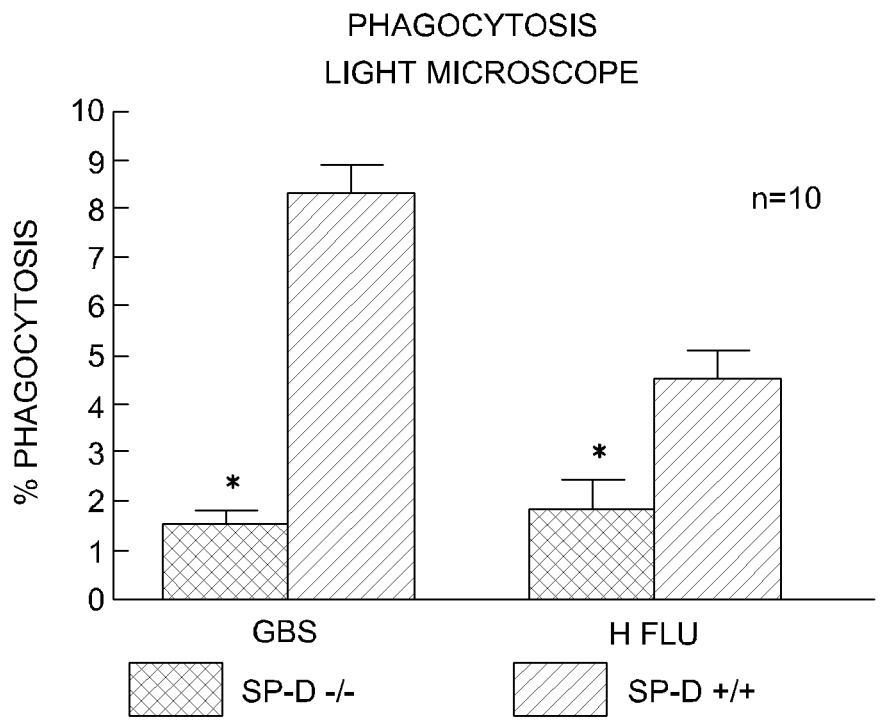
FIGS. 10A and 10B depict Phagocytosis analyzed by either light microscopy or FACS analysis after infection with GBS and *H. flu*, respectively.
Figure 10B:
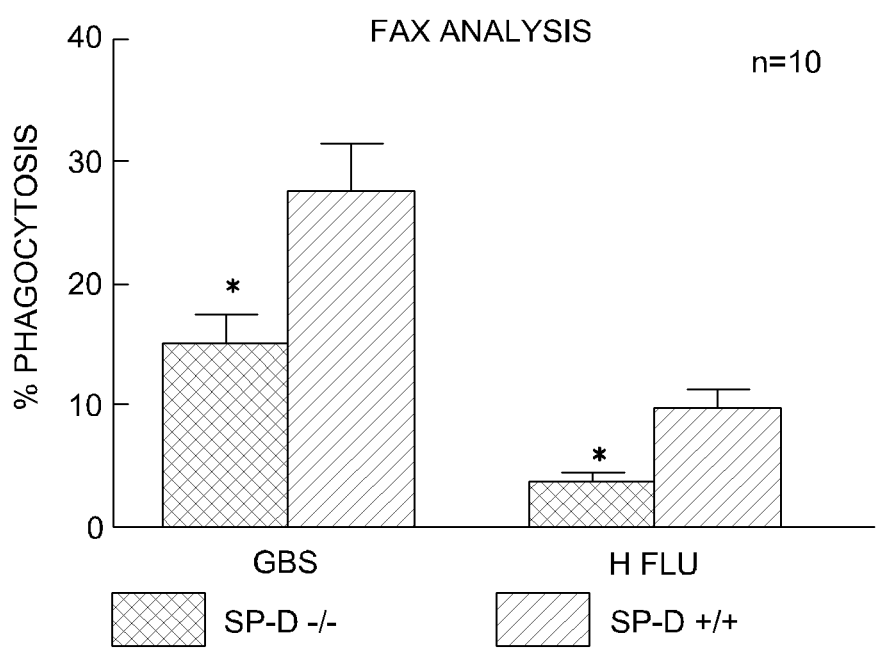

In FIGS. 10A and 10B phagocytosis was evaluated using light microscopy and flow cytometry. SP-D(−/−) mice showed significantly reduced phagocytosis of bacteria as compared to wildtype.

Therefore, in the absence of SP-D increased inflammatory responses were observed following bacterial infection of the lung with GBS or *H. flu*. Production of reactive oxygen species by alveolar macrophages was enhanced in SP-D −/− mice. These results support a critical and distinct role of SP-D in pulmonary immune and inflammatory responses to bacterial infection, in vivo.

In Example 13, the SP-D(−/−) mice were infected with Respiratory Syncytial Virus.

Host defense mechanisms have evolved to maintain the lung clear of microbial pathogens including innate mediators of bacterial and viral clearance and acquired immune responses.

Example 13

Clearance of Virus from SP-D(−/−) Mice

SP-D(−/−) mice were intratracheally infected with respiratory syncytial virus (RSV), a common respiratory pathogen in children. Viral titers and lung inflammation were assessed in SP-D (−/−) mice and wild type mice. RSV titers in lung homogenates were significantly increased in SP-D (−/−) compared to wild type mice 3 and 5 days after administration. However, significantly increased numbers of inflammatory cells were found in BAL fluid from SP-D (−/−) mice with a greater percentage of PMNs compared to wild type mice, 3 and 5 days after RSV infection. In addition, lung inflammation assessed by histology, 5 days after RSV infection was greater in SP-D (−/−) compared to wild type mice. Pro-inflammatory cytokines, including TNF-α, IL-1, IL-6 and MIP-2 were greater in lung homogenates from SP-D (−/−) mice 3 and 5 days after RSV infection. SP-D (−/−) mice had less efficient viral clearance from the lung and demonstrated greater inflammatory responses following RSV infection than wild type mice. These findings demonstrate that SP-D plays an important role in innate defense and regulation of inflammation in the lung after RSV infection in vivo. Similar findings were observed after influenza and adenovirus infected the lung.

Example 14

Clearance of Fungi from the SP-D(−/−) Mice

The mouse is infected as follows: an appropriate prototype of a fungal pathogen is used. The infectious agent is purified as appropriate and suspended in appropriate buffer and administered intratracheally with or without SP-D into the SP-D (−/−) mouse (as in Examples 12 and 13). The fungal prototype is administered at an appropriate dose. SP-D (−/−) and SP-D (+/+) mice are used to test the effect of SP-D on susceptibility of mice to infection. SP-D (−/−) mice with or without SP-D protein is used to test SP-D as a therapy for infection. Clearance of infection is evaluated as in Examples 12 and 13 and as follows:

Fungal clearance is determined by purifying lung and spleen homogenates at 6, 24, and 48 hours after inoculation of the animals with infectious agent or infectious agent with SP-D. Bacterial clearance from the lungs is determined after varying SP-D concentrations appropriately. Quantitative cultures are also determined for the SP-D (+/−) mice a to determine if 50% reduction in SP-D provides sufficient endogenous SP-D for bacterial or viral clearance.

Appropriate concentrations of mammalian SP-D are used in other mammals for treatment of pulmonary infections.

Pharmaceuticals that Regulate SP-D Levels

The importance of SP-D in normal function and development of the lung is clearly demonstrated by the SP-D (−/−) null mouse. Therefore, agents that regulate production, expression, or the action of SP-D are important future pharmaceuticals and experimental aids for identifying further such pharmaceuticals. Many techniques for identifying such agents would suggest themselves to one having ordinary skill in the art. Examples 15 and 16 outline a sample protocol for two of these techniques. Example 17 shows that IL-4 markedly increases SP-D levels in vivo and could thus be used to treat various pulmonary diseases with or without the addition of SP-D.

Example 15

Proteins that Interact with the SP-D Promoter

A one-hybrid technique is set up using the SP-D promoter to identify proteins that up-regulate expression of SP-D. These proteins are then tested on the SP-D (−/−) mouse for efficacy in treating emphysema and other pulmonary diseases and infections as in Example 8.

Example 16

Proteins that Interact Directly with the SP-D Protein

A two-hybrid technique is set up to identify proteins that interact directly with the SP-D protein. These proteins are then be tested on the SP-D (−/−) mouse for efficacy in treating emphysema and other pulmonary diseases and infections as in Example 8.

Example 17

IL-4 Increases SP-D Levels In Vivo

Figure 15:
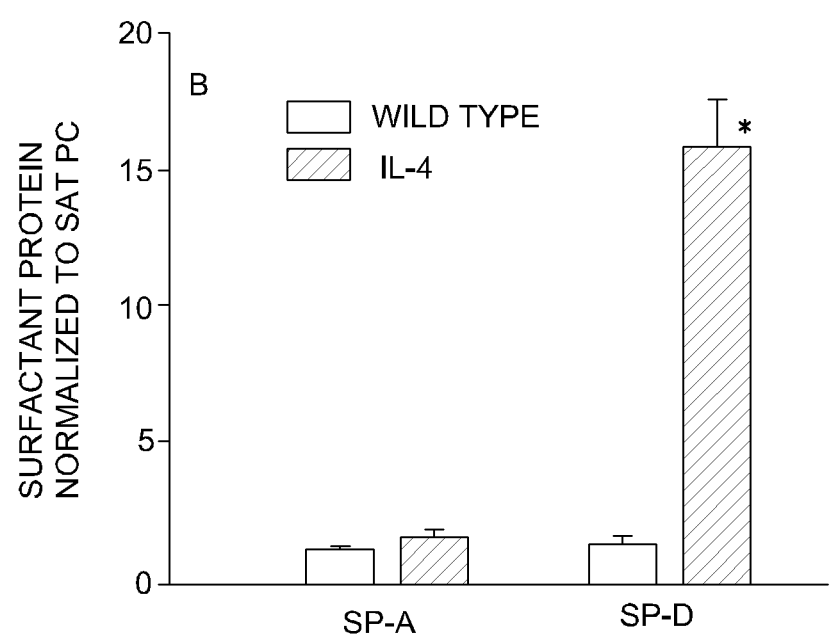
FIG. 15: Quantification of immunoblots of SP-A and SP-D in alveolar washes from wild type and CCSP-IL-4 mice (IL-4 mice). $p<0.01$.
Figure 16A:
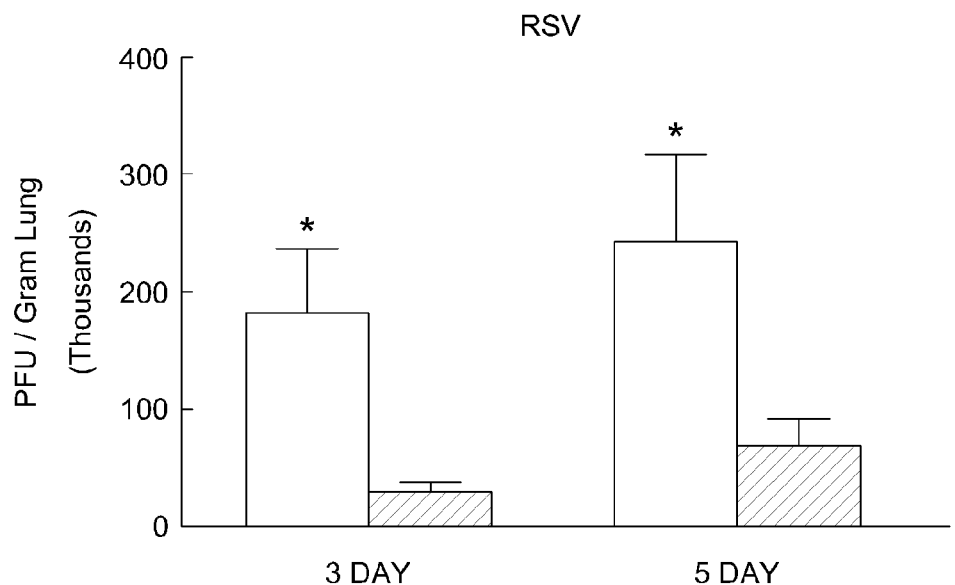
FIGS. 16A and 16B depict either RSV or IAV titers in SP-D (−/−) and wild-type mice, respectively. RSV and IAV titers were determined by quantitative plaque assays of lung homogenates. Viral titers of RSV were significantly greater 3 and 5 days after administration of $10^7$ pfu RSV (FIG. 16A) in SP-D −/− (open bar) compared to wild type (hatched bar) mice. Lung homogenate titers of IAV were significantly greater for SP-D −/− (open bar) compared to wild type (hatched bar) mice 3 and 5 days after infection (FIG. 16B). Data are mean±SEM with n=15 mice per group (FIG. 16A) and n=10 mice per group (FIG. 16B). $*p<0.05$ compared to wild type mice.
Figure 16B:
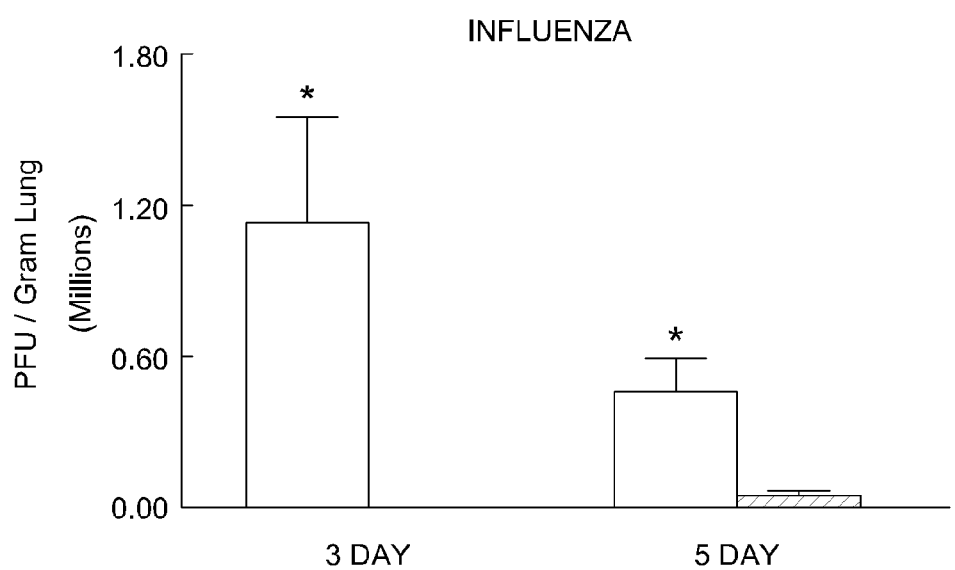
Figure 17A:
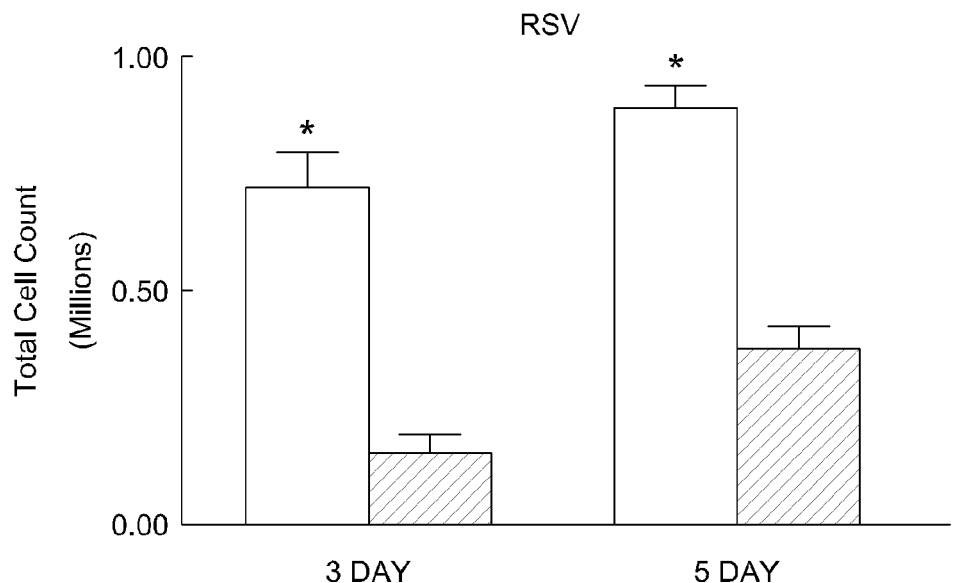
FIGS. 17A and 17B depict total cell counts from mice infected with either RSV or IAV, respectively. Lung cells were recovered by bronchoalveolar lavage, stained with trypan blue and counted under light microscopy. SP-D −/− mice (open bar) had increased total cell counts in BAL fluid 3 and 5 days after RSV infection (FIG. 17A) compared to wild type mice (hatched bar). SP-D −/− (open bar) had increased total cell counts in BAL fluid 3 and 5 days after IAV infection (FIG. 17B). Data are mean±SEM with n=8 mice per group, $*p<0.05$ compared to wild type mice.
Figure 17B:
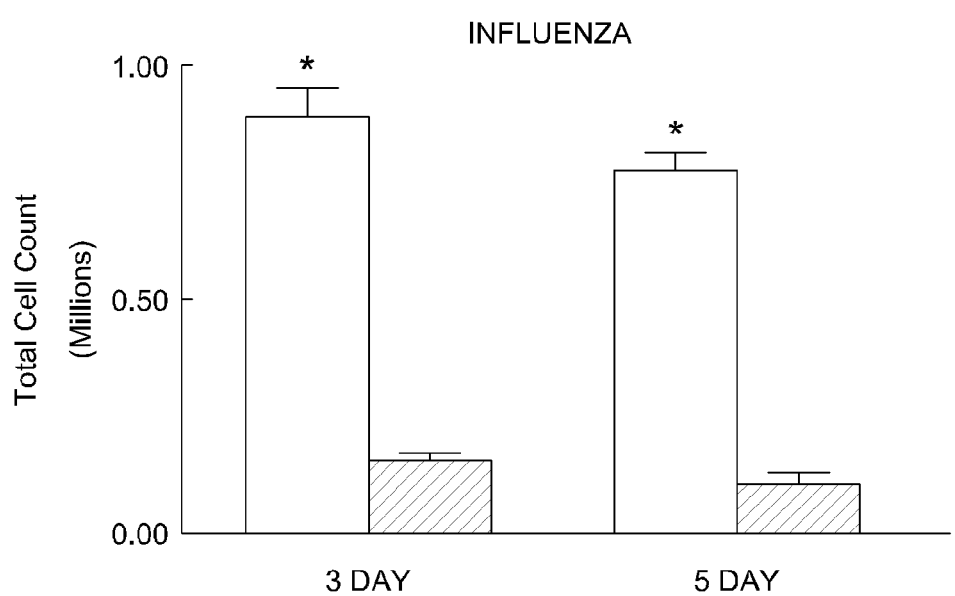
Figure 18A:
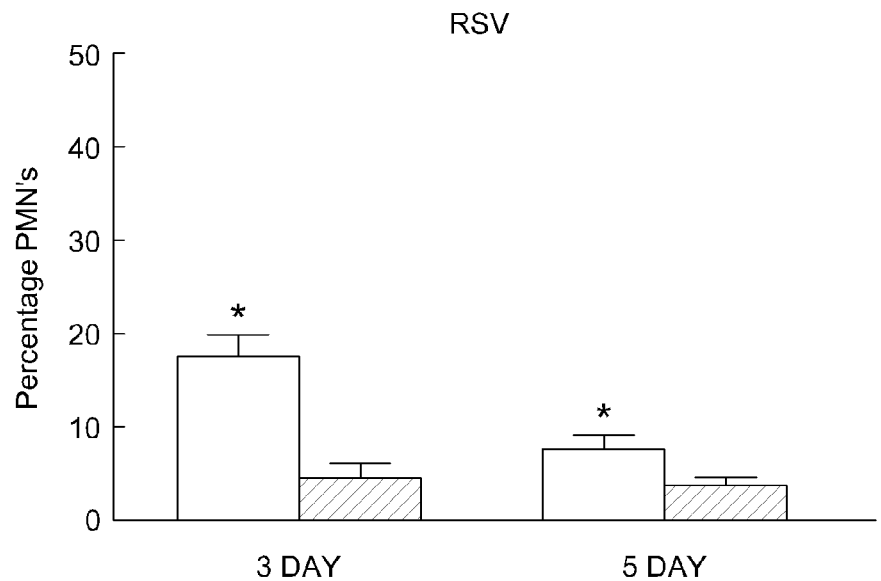
FIGS. 18A and 18B depict percentage PMN in mice infected with either RSV or IAV, respectively. Cytospin preparations of bronchoalveolar lavage fluid were stained with DIFF-QUIK to identify macrophages, lymphocytes and polymorphonuclear leukocytes. The percentage of neutrophils in BAL fluid was significantly greater 3 and 5 days after administration of $10^7$ pfu RSV to SP-D −/− (open bar) compared to wild type (hatched bar) mice (FIG. 18A). Similarly, the percentage of neutrophils in BAL fluid was significantly greater 3 and 5 days after administration of $10^5$ pfu IAV to SP-D −/− (open bar) mice compared to wild type (FIG. 18B). Data are mean±SEM with n=8 mice per group, $*p<0.05$ compared to wild type mice.
Figure 18B:
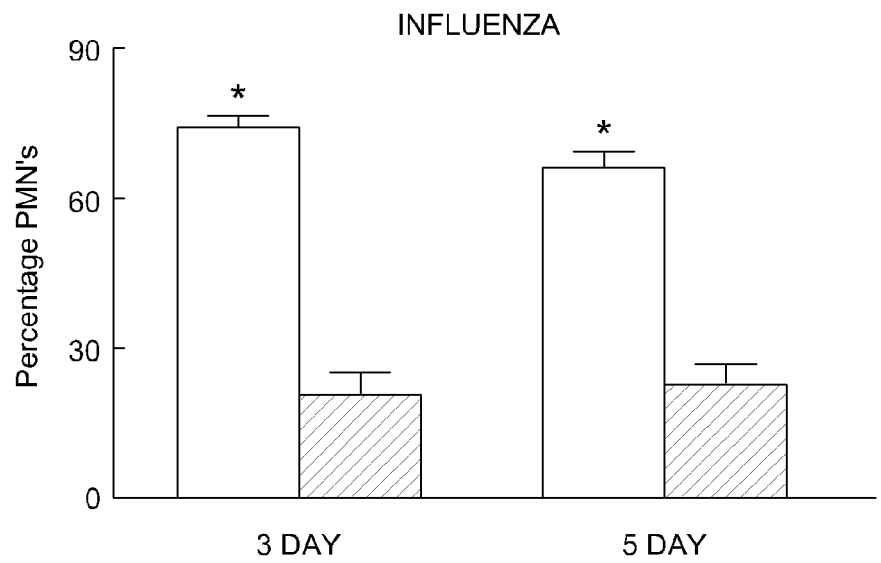

Mice that express IL-4 in Clara cells (CCSP-IL-4) develop chronic airway inflammation and an alveolar proteinosis-like syndrome. In order to identify the role of IL-4 in surfactant homeostasis, lipid and protein metabolism were measured in the lungs of CCSP-IL-4 mice in vivo. Alveolar saturated phosphatidylcholine (Sat PC) pools were increased 6.5 fold and lung tissue Sat PC pools were increased 4.8 fold in the IL-4 transgenic mice (see FIG. 15). SP-D was increased approximately 90 fold in the IL-4 mice compared to wild type mice and was associated with 2.8 fold increased SP-D mRNA (see FIG. 15). The incorporation of palmitate and choline into Sat PC was increased about 2 fold in CCSP-IL-4 mice. Net clearance of Sat PC from the lungs of CCSP-IL-4 mice was 6 fold higher (60 μmol/kg) in the IL-4 mice than in wild type mice (10.3 μmol/kg). Expression of IL-4 in Clara cells increased surfactant lipid synthesis and clearance, establishing a new equilibrium with increased surfactant pools and an alveolar proteinosis associated with a selective increase in SP-D protein, demonstrating a previously unexpected effect of IL-4 in pulmonary surfactant homeostasis and the regulation of SP-D levels by IL-4.

Diagnosis Using SP-D Protein or Sequence

SP-D is important in normal lung function and development. SP-D (−/−) mice are a model for emphysema. This then suggests that mutations in the gene or alleles of the gene for SP-D have a profound effect on pulmonary disease susceptibility. Therefore, a method to identify mutations or alleles, and mutant protein identifies individuals at risk for emphysema, pulmonary infections, and a number of other respiratory diseases. Example 18 and 19 are sample protocols for these diagnostic techniques.

Example 18

Diagnosis of Patients with Mutations in the SP-D Gene

Mutations in the SP-D gene are likely involved in the symptoms and etiology of emphysema. Therefore, mutations are identified by sequence analysis of a statistically significant number of patients. These mutations are used to produce a diagnostic test. Mutations in the SP-D gene are detected in the following ways: PCR analysis of the SP-D gene using appropriate primers is performed. Resulting PCR fragments are analyzed by SSCP and sequenced to determine mutation or allele. Alternatively, differential hybridization of genomic DNA or cDNA is used to detect mutations.

Example 19

Diagnosis of Patients with Mutant SP-D Protein

Monoclonal or polyclonal antibodies which specifically recognize mutant SP-D protein or an allele of SP-D associated with emphysema or other pulmonary diseases are produced. These antibodies are then used to set up an enzyme-linked immunoassay or Western blot assay for susceptibility to these pulmonary diseases. The antibodies of Example 20 can be used for this assay.

Example 20 presents a protocol for the purification of polyclonal or further purification of monoclonal antibodies using transgenic technology.

Example 20

Purification of SP-D Specific Monoclonal and Polyclonal Antibodies

The production of specific polyclonal antibodies with a high reactivity involves extensive purification of the antigen of interest. Several polyclonal antibodies were developed using partially purified antigens for injection which have resulted in antibodies which have a high titer with respect to the antigen of interest and are also reactive to impurities. Solid phase tissue from transgenic mice have been used to remove nonspecific antibodies from these antisera. Surfactant Protein-D (SP-D) was purified using a maltose column with manganese elution. The purified SP-D was injected into New Zealand rabbits in incomplete Freund's adjuvant. The resulting antisera was tested against whole lung lavage on a Western Blot, revealing binding to the SP-D and to other proteins. This antisera was reacted overnight with a solid phased lung homogenate from a null mutant mouse which does not produce any SP-D protein. The antisera was reacted against whole lung lavage after absorption showing reactivities only against SP-D. This antisera was also evaluated in immunohistochemistry experiments which demonstrated very low reactivities to lung sections from SP-D null mutant mice and very specific type II cell reactivities in normal control mice. This technique greatly enhances the ability to prepare highly specific antibodies with high titers and eliminates the need to use blocking agents when using absorbed antibodies.

These antibodies could be used for the diagnosis, purification, and further research into the SP-D protein.

Example 21

SP-D Inhibits Viral Infection

Previous results (Example 13) showed that SP-D has a role in the clearance of RSV from the lungs of mice. Therefore, it was of interest to see if SP-D had a similar role in the clearance of other viruses.

SP-D(−/−) mice were intratracheally infected with influenza A virus and separately with adenovirus. Viral titers and lung inflammation were assessed in SP-D (−/−) mice and wild type mice. Influenza A titers in lung homogenates were significantly increased in SP-D (−/−) compared to wild type mice 3 and 5 days after administration. Significantly increased numbers of inflammatory cells were found in BAL fluid from SP-D (−/−) mice with a greater percentage of PMNs compared to wild type mice, after influenza A infection.

Therefore, SP-D deficient mice are susceptible to influenza A viral infection in vivo and developing markedly increased lung inflammatory responses to the virus and SP-D binds adenovirus in vitro and will likely play a role in clearance of adenovirus in vivo as well.

Example 22

SP-D Inhibits Reactive Lipid Species

SP-D deficient surfactant has increased oxygen-lipid intermediates (toxic lipid reactants). Thus, SP-D inhibits reactive lipid species in the airspace and may have potential benefits for amelioration of reactive oxygen mediated disease, chemically induced lung injury, oxygen, ozone, chemotherapeutic agents and inflammatory diseases, reperfusion injury, drowning, transplantation, and rejection.

Reactive oxygen species were measured by the Lipid Hydroperoxide (LPO) assay kit (Caymen chemicals, Cat. No. 705002). Surfactant was isolated from SP-D knockout and wildtype mice by lung lavage and the lipid peroxidation products measured using redox reactions with ferrous ions. No lipid peroxides were detected in surfactant from wild type mice (n=4) but were readily detected in lavage fluid from SP-D (−/−) mice, 0.896±0.305 ng of lipid peroxidation product/mg of phospholipid (n=4).

Methods and Compositions Containing SP-D to Enhance Clearance of Virus from the Lung There is increasing evidence that SP-D is involved in innate host defense against various bacterial, fungal and viral pathogens. In vitro, SP-D interacts with bacteria, fungi and viruses. SP-D also binds to alveolar macrophages and increases macrophage association with *Escherichia Coli, Pseudomonas aeruginosa, Mycobacterium tuberculosis* and *Pneumocystis carinii*. In vitro, mannose binding protein, conglutinin, SP-A and SP-D neutralize influenza A virus (IAV) and enhance the association of neutrophils with IAV.

A number of viruses are associated with respiratory disease in the upper and lower respiratory tract. These include RSV, influenza, chickenpox, fifth disease (human parvovirus B19), parainfluenza virus types 1-3, cytomegalovirus, rhinovirus, adenovirus, hantavirus and rubella. Influenza A virus infection is airborne and is primarily an infection of the upper respiratory tract. However, during infection, virus spreads to the lower respiratory tract and may result in viral pneumonia or may predispose a patient to secondary bacterial infections. Influenza infections are most frequent in children and young adults yet deaths are most frequent in very young (<1 yr), the elderly and persons of all ages with underlying heart or lung disease. Bronchopulmonary dysplasia has been associated with decreased secretion of SP-D, and cystic fibrosis has been associated with decreased SP-D concentrations in pulmonary washes, conditions that may increase susceptibility to infection by respiratory viruses such as IAV.

Specific as well as nonspecific immune mechanisms take part in the host response to influenza virus. Influenza A virus infection is a lytic infection and causes the breakdown of the blood-tissue barrier early in infection, resulting in the influx of macrophages, neutrophils, and natural killer cells into the lung. Specific immune responses to IAV are initiated by the influx of virus specific T lymphocytes and antibody production, and cytotoxic T lymphocytes are thought to be involved in viral clearance by direct cytolysis of virus-infected cells. Neutrophils also play an important role in viral clearance from the lung. Mice irradiated to reduce the number of peripheral polymorphonuclear leukocytes have increased viral titers after influenza infection in the lung. Defects in neutrophil and monocyte chemotactic, oxidative and bacterial killing functions have been documented in IAV infection. In vitro, neutrophil dysfunction resulting from IAV exposure is diminished when the virus is pre-incubated with SP-D. On the other hand, SP-D has been reported to have no effect on IAV uptake by alveolar macrophages.

Although there is compelling evidence that SP-D enhances host defense against viruses in vitro, its role in the clearance of viral pathogens in vivo has not been demonstrated. Thus, the role for SP-D in viral clearance was clarified in Examples 23-29 in which SP-D deficient mice were infected intranasally with SP-D sensitive and resistant strains of influenza A virus. Rescue experiments were performed using highly purified recombinant SP-D. IAV clearance, lung inflammation, cytokine production, and uptake of virus by macrophages and neutrophil activity were compared in SP-D −/− and SP-D +/+ mice in vivo. The experiments show a role for SP-D in clearance of the virus from the lungs as well as reduction in the inflammatory properties. Thus, SP-D can be used in the treatment of viral infections and the resulting inflammation in the lungs, particularly for the treatment of infections in the very young, very old, immunocompromised, and those with any types of lung deficiencies.

Thus, embodiments include a method for treating viral infections in a patient using SP-D or active SP-D variants. The SP-D can be administered as a protein as in Example 9. Alternatively, the SP-D can be expressed from an adenovirus, or other vector as in Examples 10 and 11. Alternatively, the an active SP-D gene can be upregulated using SP-D transcriptional activators.

Viral infections treatable using SP-D include any pulmonary viral infections, whether primary or secondary, including influenza A, rhinovirus and other viruses which cause the common cold or cold-related symptoms, RSV, chickenpox, fifth disease (human parvovirus B19), parainfluenza virus types 1-3, cytomegalovirus, rhinovirus, adenovirus, hantavirus and rubella.

Alternatively, the inflammation and symptoms associated with viral infections may be treated with SP-D. For example, colds and flus often result in inflammation even after the virus has been cleared. This inflammatory response or an equivalent response can be treated with SP-D.

Patients for which SP-D treatment can be used include all patients with pulmonary viral infections. However, particularly patients with a reduced level of SP-D or inactive SP-D. Such patients include but are not restricted to patients with: asthma, emphysema, cystic fibrosis, patients who are immunocompromised, very young patients, particularly those with under-developed immune systems, and very old patients.

EXAMPLES

In Examples 23-29, influenza A virus (IAV) was administered to SP-D −/− and SP-D +/+ mice in order to identify the role that SP-D plays in viral infection in the lungs. Influenza A virus was used as a prototypical pulmonary virus. In Examples 24-29, the effect on viral clearance, neutrophil MPO activity, CD4 and CD8 T cell proliferation, surfactant protein D concentrations, and cytokine levels was evaluated. Lung viral titers, total cell counts, cytokines, MPO activity and SP-D levels were compared using analysis of variance (ANOVA) and Student's t test. Findings were considered statistically significant at probability levels<0.05.

In Examples 24-29, the pulmonary clearance of intranasally administered Phil/82 strain of influenza A virus was reduced in SP-D −/− mice compared to SP-D +/+ mice. However, the less glycosylated strain Mem/71, which is relatively resistant to SP-D in vitro, was cleared efficiently from the lungs of SP-D −/− mice. In addition, the co-administration of recombinant SP-D normalized viral clearance. Thus, the impaired clearance of IAV can be directly attributed to the deficiency in SP-D rather than to other aspects of the SP-D null phenotype or more global host defense deficits. In this regard, previous results demonstrated that SP-D null mice show no impairment of clearance of Group B *streptococcus* and *Haemophilus influenzae*. Pulmonary inflammation was increased in SP-D deficient mice compared to wild type controls as indicated by increased total cell counts and pro-inflammatory cytokines in the lung after IAV infection. Neutrophil myeloperoxidase activity was decreased in SP-D −/− mice suggesting neutrophil clearance of IAV may be impaired. Pulmonary IAV infection increased SP-D concentrations in wild type mice. These findings demonstrate that SP-D plays an important role in the initial pulmonary host defense against certain strains of IAV and other pulmonary viruses in vivo.

Impaired clearance of IAV from the lungs of SP-D −/− mice supports the importance of SP-D in host defense. SP-D is a member of the C-type-lectin family of polypeptides that includes mannose binding protein, conglutinin and SP-A. C-type lectins share structural features including collagenous amino-terminal and "globular" carboxy-terminal domains, the latter serving as a carbohydrate recognition domain that functions in opsonization. In the presence of calcium, SP-D binds to a variety of glycoconjugates, including di- and mono-saccharides such as maltose, glucose and mannose. Influenza virus has two membrane glycoproteins, the hemagglutinin (HA) and neuraminidase (NA). Collectins bind to oligosaccharides on influenza virus glycoproteins and neutralize virus infectivity in vitro, more heavily glycosylated strains of viruses being the most sensitive. SP-D may enhance viral clearance by binding to the carbohydrate side chain of IAV blocking access of cell surface receptors to the receptor-binding site thus interfering with virus internalization by host cells. In addition, SP-D binds and agglutinates IAV, which may, in part, enhance viral removal from the lung through mucociliary and phagocytic clearance. However, the finding that uptake of the virus by alveolar macrophages is not reduced suggests that SP-D binding, aggregation and uptake by the alveolar macrophages is not a critical determinant of decreased viral killing noted in the SP-D −/− mice.

In the absence of SP-D, IAV viral clearance from the lung was impaired. In addition, lung inflammation was more severe in SP-D −/− mice, suggesting that SP-D plays a role in modulating cytokine production and inflammatory responses during viral infection. SP-D has a further role by binding to and agglutinating IAV that may also enhance IAV removal from the lung through mucociliary clearance and enhanced recruitment and activation of polymorphonuclear leukocytes. Since the airway is the usual portal of entry for influenza virus and other respiratory pathogens, the local production of SP-D may also be involved in innate defense responses to inhaled viruses.

Example 23

Pulmonary Pathology of SP-D −/− Mice after IAV Administration

SP-D −/− mice were produced by targeted gene inactivation as presented in Example 1. Lungs of SP-D −/− mice do not contain detectable SP-D. The original 129/NIH Swiss Black heterozygous mouse was bred to NIH Swiss Black mice, and SP-D −/− and SP-D +/+ colonies maintained. Mice were housed in barrier containment and remained viral free as assessed by serology. Studies were reviewed and approved by the Institutional Animal Care and Use Committee of the Children's Hospital Research Foundation, Cincinnati. Male and female mice of approximately 20-25 grams (35-42 days old) were used.

IAV to be used for administration to the SP-D −/− and SP-D +/+ mice was prepared as follows: IAV strain $H_3N_2$ A/Phillipines/82 (Phil/82) and H3N1 Mem71$_H$-Bel$_N$(Mem71) were a gracious gift from E. M. Anders to K. Hartshorn (University of Melbourne, Melbourne, Australia) and were grown in the chorioallantoic fluid of 10-day-old embryonated hen's eggs. Allantoic fluid was harvested after 48 h of incubation and clarified by centrifugation at 1,000 g for 40 min followed by centrifugation at 135,000 g to precipitate viruses. The virus-containing pellets were resuspended and purified on a discontinuous sucrose density gradient as previously described (Hartshorn, et al. 2000. Enhanced anti-influenza activity of a surfactant protein D and serum conglutinin fusion protein. *Am. J. Physiol. Lung Cell. Mol. Physiol.* 278:L90-L98). Virus stocks were dialyzed against phosphate buffered saline (PBS), separated into aliquots, and stored at −70° C. until use. Hemagglutinin (HA) titers were determined by titration of virus samples in PBS followed by the addition of thoroughly washed human type O red blood cells. The potency of each viral stock was measured by HA and protein assays after samples were thawed from frozen storage at −70° C. The virus was labelled with FITC using the following procedure:

Fluorescent isothiocyanate (FITC) stock was prepared at 1 mg/ml in 1 mol/L sodium carbonate, pH 9.6. FITC-labeled virus (Phil/82) was prepared by incubating concentrated virus stocks with FITC (10:1 mixture by volume of virus in PBS with FITC stock) for 1 hour, followed by dialysis of the mixture for 18 hours against PBS.

Inoculation of FITC-Labelled IAV

Mice were lightly anesthetized with isoflurane and inoculated intranasally with $10^5$ fluorescent foci (ff) of IAV in 50 µl of PBS. Quantitative IAV cultures of lung homogenates were performed 3 and 5 days after inoculation of the animals with IAV. The entire lung was removed, homogenized in 2 ml of sterile PBS, quick-frozen, weighed and stored at −80° C. Madin-Darby canine kidney monolayers were prepared in 96-well plates for the viral focus assay as previously described (Hartshorn, et al. 2000. Enhanced anti-influenza activity of a surfactant protein D and serum conglutinin fusion protein. *Am. J. Physiol. Lung Cell. Mol. Physiol.* 278: L90-L98). The layers were incubated with lung homogenates diluted in PBS containing 2 mM calcium for 45 minutes at 37° C., and the monolayers washed three times in virus-free DMEM containing 1% penicillin and streptomycin. The monolayers were incubated for 7 h at 37° C. in DMEM and repeatedly washed, and the cells were fixed with 80% (vol/vol) acetone for 10 min at −20° C. The monolayers were then incubated with monoclonal antibody directed against IAV nucleoprotein (monoclonal antibody A-3), and then with rhodamine-labeled goat anti-mouse IgG. Fluorescent foci were counted directly by fluorescent microscopy. The resulting titer was divided by the lung weight and reported as fluorescent foci (ff)/gram of lung.

Figure 19A:
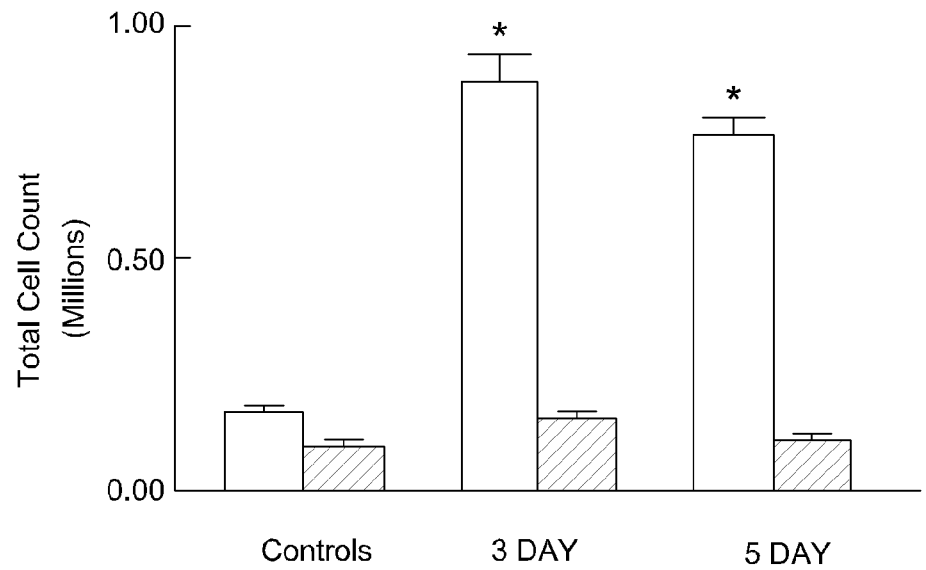
FIGS. 19A and 19B depict either total cell counts or percentage PMN in mice, respectively, and show increased total cell counts and neutrophils in BAL fluid from SP-D −/− mice: Lung cells were recovered by bronchoalveolar lavage, stained with trypan blue and counted under light microscopy. Cytospin preparations of bronchoalveolar lavage fluid were stained with Diff-Quik to identify macrophages, lymphocytes and polymorphonuclear leukocytes. Baseline total cell counts from controls inoculated with PBS were not significantly different in SP-D −/− (open bar) and SP-D +/+ (hatched bar) mice. SP-D −/− mice had increased total cell counts in BAL fluid 3 and 5 days after IAV infection compared to SP-D +/+ mice (FIG. 19A). The percentage of neutrophils in BAL fluid was significantly greater 3 and 5 days after administration of $10^5$ ff IAV to SP-D −/− (open bar) compared to SP-D +/+ (hatched bar) mice (FIG. 19B). Data are mean±SEM with n=8 mice per group, $*p<0.05$ compared to SP-D +/+ mice.
Figure 19B:
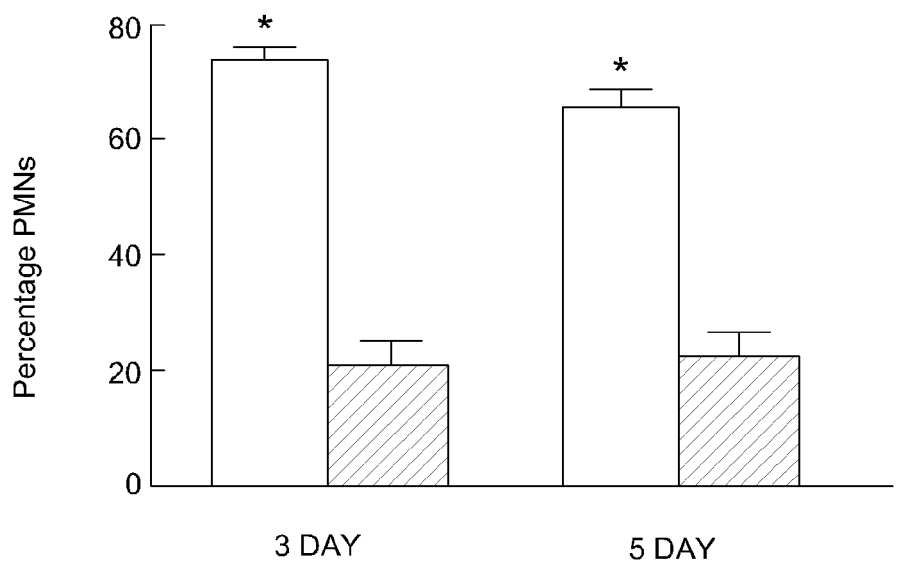

Intranasal administration of IAV ($10^5$ ff) was well tolerated and all animals survived the study period. Mice infected with IAV lost weight during the 4 days post infection. The percentage of weight loss was greater for the SP-D −/− mice with 14.4±1.4%* compared to 1.5±1.0% for the SP-D +/+ mice, mean±SEM, n=6 mice, *p<0.05 compared to SP-D +/+ mice. Increased total cell counts in BALF were observed in SP-D −/− mice 3 and 5 days after IAV infection, see FIGS. 19A and 19B. Baseline total cell counts in BAL fluid from controls inoculated with PBS were not significantly different for the SP-D +/+ and SP-D −/− mice, see FIGS. 19A and 19B. A significantly greater percentage of PMNs was detected in BAL fluid from SP-D −/− compared to SP-D +/+ mice 3 and 5 days post infection, see FIGS. 19A and 19B. Pulmonary infiltrates were not observed in wild type mice inoculated with sterile PBS (n=5).

In Example 24, clearance of IAV was quantitated in SP-D −/− and wild-type mice.

Example 24

Viral Clearance in SP-D −/− Mice

Quantitative IAV cultures of lung homogenates were performed 3 and 5 days after inoculation of the animals with different strains of IAV. Strains of influenza virus differ in the extent of glycosylation of surface glycoproteins. To examine whether strain dependent changes in glycosylation influence SP-D dependent clearance, infection by Mem71$_H$-Bel$_N$ (H3N1) (Mem/71) was compared with Phil/82. Previous studies have shown that Mem/71, which has a less glycosylated hemagglutinin than Phil/82, is relatively resistant to the effects of SP-D in vitro. Mem/71 shows less SP-D dependent viral agglutination and hemagglutination inhibition, decreased enhancement of neutrophil uptake and activation and decreased inhibition of infectivity as compared to SP-D sensitive strains. Significantly, titers in the lung of Mem/71 were similar for SP-D −/− ($6.8 \times 10^3 \pm 1.9 \times 10^3$ ff/gram lung) and SP-D +/+ mice ($5.9 \times 10^3 \pm 1.4 \times 10^3$), mean±SEM, 8 mice per group.

Figure 20:
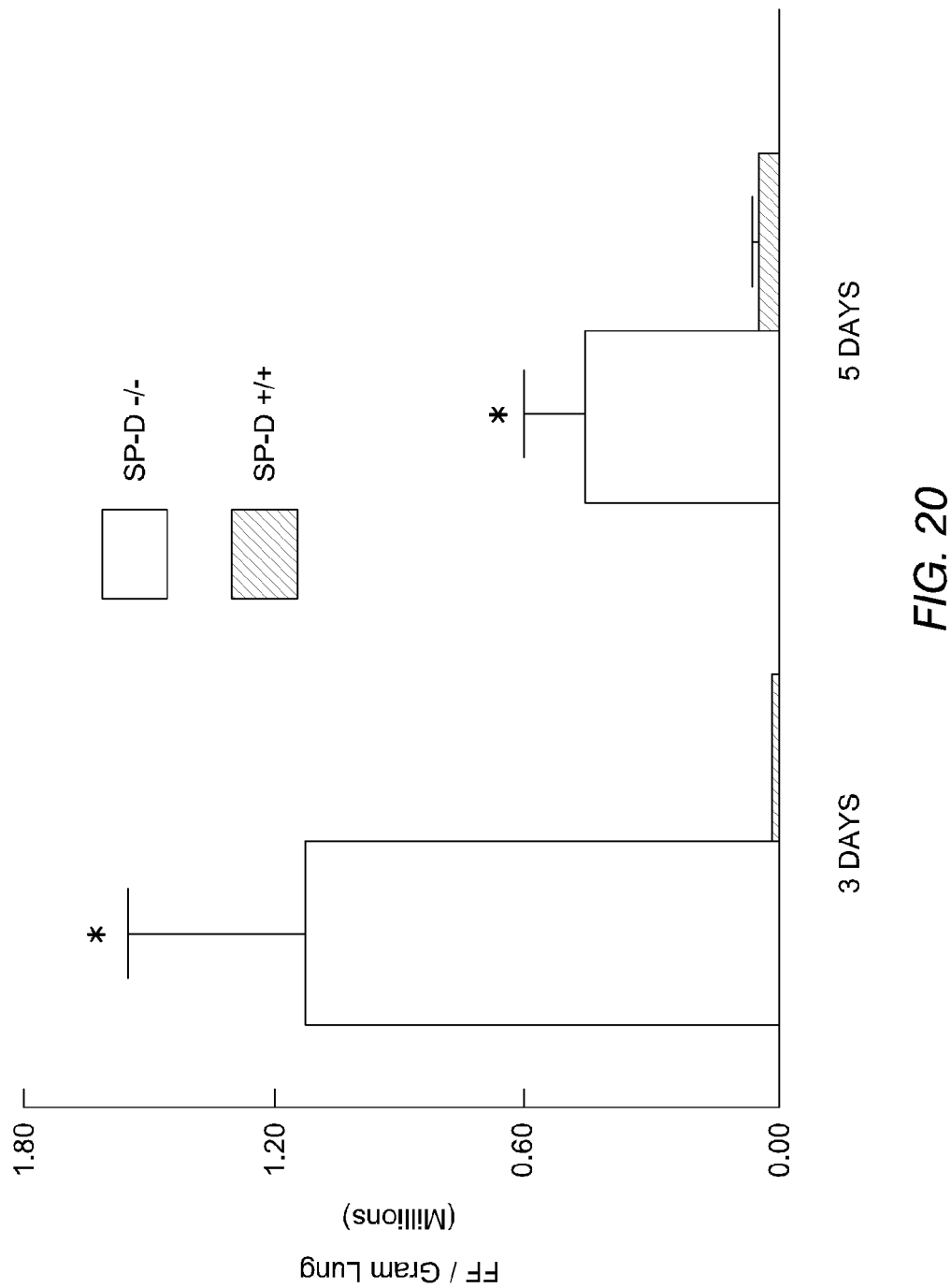
FIG. 20 shows increased viral titers in lung homogenates from SP-D −/− mice: IAV titers were determined by quantitative plaque assays of lung homogenates. Viral titers of IAV were significantly greater 3 and 5 days after administration of $10^5$ ff IAV for SP-D −/− (open bar) compared to SP-D +/+ (hatched bar) mice. Data are mean±SEM with n=10 mice per group, $*p<0.05$ compared to SP-D +/+ mice.

However, increased viral titers of IAV (Phil/82) were observed in the lungs of SP-D −/− mice 3 and 5 days after infection compared to SP-D +/+ mice, see FIG. 20.

Next, human SP-D was administered to the IAV-infected mice to analyze the effect. Human SP-D (hSP-D) was isolated as previously described (Hartshorn, et al. 1996, "Interactions of recombinant human pulmonary surfactant protein D and SP-D multimers with influenza A", Am. J. Physiol. 271: L753-L762). Briefly, CHO-K1 cells (ATCC CCL-61) were transfected with a full-length human cDNA in the pEE14 mammalian expression vector. Secreted SP-D was isolated by maltosyl-agarose affinity chromatography and SP-D dodecamers were resolved from larger multimers and trimers by gel filtration chromatography under non-denaturing conditions. Proteins were concentrated by re-chromatography on maltosyl-agarose. Bound proteins were eluted in HEPES-buffered saline containing 10 mM EDTA and stored at −80° C. The protein concentration was estimated using a dye binding assay with bovine serum albumin as standard. The level of endotoxin contamination was quantified using an end-point chromogenic microplate assay (Chromogenix, Sweden) with *E. coli* 0111:B4 endotoxin as a standard. The endotoxin content of the purified recombinant proteins used for these experiments was <2 ng/ml for stock solutions. Quantitative IAV cultures of lung homogenates were performed 3 days after intranasal inoculation of mice with IAV followed by intratracheal inoculation with PBS or SP-D (5 µg).

Intratracheal co-administration of recombinant SP-D (5 µg) enhanced clearance of A/Phillipines/82 ($H_3N_2$) (Phil/82) virus from the lung of SP-D −/− ($7.5 \times 10^4 \pm 1.4 \times 10^4$*ff/gram lung) compared to untreated SP-D −/− ($1.6 \times 10^5 \pm 4.0 \times 10^4$) mice 3 days after infection, mean±SEM, n=8 mice per group, *p<0.05.

This suggests that SP-D has a role in clearance of virus from the lung and that the administration of SP-D to a deficient animal enhances viral uptake, providing a method for the treatment of pulmonary viral infections.

In Example 25, cytokine levels were analyzed in IAV-infected SP-D−/− and SP-D +/+ mice.

Example 25

Cytokine Levels in Lung Homogenates

Cytokine levels were analyzed 3 and 5 days after IAV infection of SP-D −/− and SP-D +/+ mice. Lung homogenates were centrifuged at 2000 RPM and the supernatants stored at −20° C. Tumor necrosis factor alpha (TNF-α☐), interleukin (IL)-1β☐, IL-6, and macrophage inflammatory protein (MIP)-2 were quantitated using murine sandwich ELISA kits (R&D systems, Minneapolis, Minn.) according to the manufacturer's directions. All plates were read on a microplate reader (Molecular Devices, Menlo Park, Calif.) and analyzed with the use of a computer-assisted analysis program (Softmax; Molecular Devices). Only assays having standard curves with a calculated regression line value>0.95 were accepted for analysis.

Figure 21:
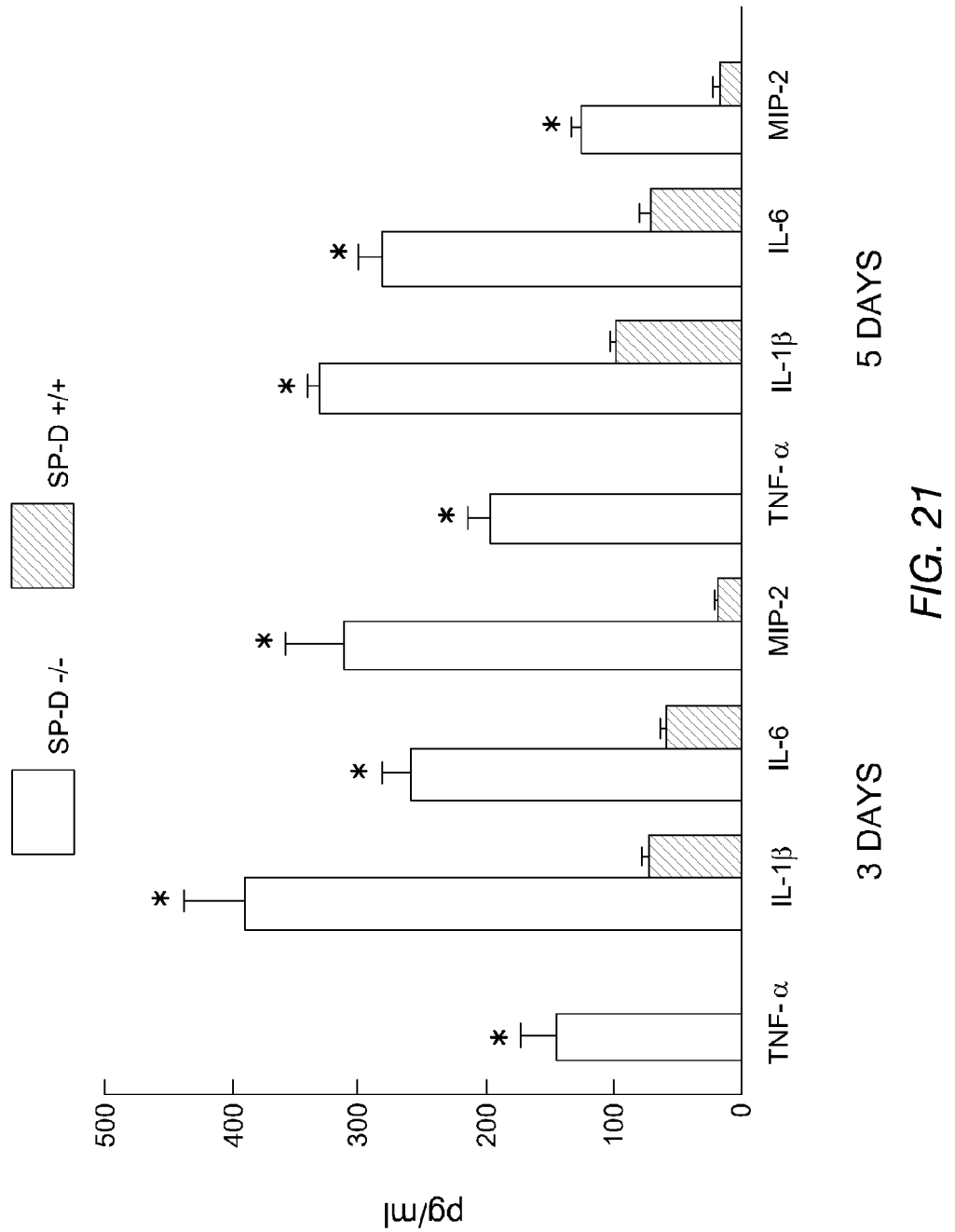
FIG. 21 shows increased pro-inflammatory cytokines in lung homogenates from SP-D −/− mice after IAV infection: Concentrations of TNF-α□, IL-1□, IL-6 and MIP-2 were assessed in lung homogenates from SP-D −/− (open bar) and SP-D +/+(hatched bar) mice. Increased concentrations of the pro-inflammatory cytokines TNF-□α, IL-6, IL-13 and MIP-2 were found in lung homogenates from the SP-D −/− mice 3 and 5 days after IAV infection. Data is expressed as pg/ml and represent mean±SEM with n=10 mice per group. $*p<0.05$ compared to SP-D +/+ mice.

The results were that three and 5 days after IAV infection, pro-inflammatory cytokines TNF-α, IL-1β and IL-6 were significantly increased in lung homogenates from SP-D −/− compared to SP-D +/+ mice, FIG. 21. IFN-γ was increased in the lungs of SP-D −/− mice compared to SP-D +/+ mice after IAV infection. Lungs from the SP-D −/− mice had the greatest concentration of IFN-γ 5 days after IAV infection with 91±20 and 2398±176 µg/ml for SP-D+/+ and SP-D−/− mice respectively, mean±SEM, *p<0.05. MIP-2, a neutrophil chemoattractant, was significantly greater in lung homogenates from SP-D −/− mice after viral infection, see FIG. 21. Intratracheal treatment with SP-D significantly reduced TNF-α (from 67.2±8.9 to 19.0±7.0 µg/ml) and IL-6 (from 481±73 to 295±29*µg/ml) levels in the lung for untreated SP-D−/− and treated SP-D−/− mice, respectively (mean±SEM, *p<0.05). Basal cytokine levels in the lungs of control mice inoculated with sterile PBS were low or absent and were not different in SP-D−/− and SP-D+/+ mice.

After IAV infection, markers of inflammation, including inflammatory cells and cytokines were increased in the lungs of SP-D −/− mice and exogenous recombinant SP-D reduced IAV induced cytokine production. SP-D −/− mice were able to mount an immune response to IAV infection; however, the response was greatly increased compared to wild type controls. Increased cytokine production may have reflected increased cells in BAL fluid after viral infection. Uninfected SP-D −/− mice have modestly increased numbers of alveolar macrophages in the lung, however pro-inflammatory cytokine concentrations were not substantially increased. Increased cytokines, TNF-α, IL-1β, IL-6 and IFN-γ, were demonstrated in the mouse model of IAV infection associated with lymphocytic and mononuclear infiltrates in the lung. The cytokine response to IAV was similar in SP-D −/− mice with elevated TNF-α, IL-1β, IL-6 and IFN-γ, however pulmonary cytokine responses to IAV were significantly greater in SP-D −/− mice than in the wild type mice. Augmented inflammatory responses have also been observed following bacterial challenge. These findings were consistent with the general hypothesis that SP-D plays important anti-inflammatory roles in vivo. It is possible that these effects served to minimize collateral damage to lung tissue while enhancing uptake or clearance.

In Example 26, the effect of SP-D on phagocytosis was assessed.

Example 26

Phagocytosis of IAV by Macrophages

Phagocytosis of FITC-labeled IAV by alveolar macrophages was assessed by flow cytometry. Uptake of virus was similar in SP-D +/+ and SP-D −/− mice (11.1±1.9% and 9.4±1.9% phagocytosis, respectively), 2 hours after IAV infection, mean±SEM. These results suggested that macrophage phagocytosis of IAV is not a major contributor to the decreased clearance of IAV seen in the absence of SP-D, in vivo.

Phagocytosis of IAV by macrophages in vivo was measured by intranasally infecting mice with FITC labeled IAV followed by evaluation of cell associated fluorescence with a flow cytometer. Two hours after infection, macrophages from BAL fluid were incubated in buffer (PBS, 0.2% BSA fraction V, 0.02% sodium azide) with phycoerytherin (PE) conjugated murine CD16/CD32 antibodies (Pharmingen, San Diego, Calif.) for one hour on ice and washed two times in fresh buffer. Trypan blue (0.2 mg/ml) was added to quench fluorescence of extracellular FITC. Cell associated fluorescence was measured on a FACScan flow cytometer, using CELLQuest software (Becton Dickinson, San Jose, Calif.). For each sample of macrophages, 20,000 cells were counted in duplicate and the results expressed as the percentage of macrophage phagocytosis.

Phagocytosis of IAV by alveolar macrophages was similar for SP-D −/− and wild type mice, in vivo. Since macrophage phagocytosis is part of the early, non specific immune response, an early time point was chosen to assess macrophage phagocytosis, however, the optimal time point for assessing viral phagocytosis by macrophages is unknown. In addition, large quantities of ingested FITC-labeled virus are necessary to detect macrophage fluorescence. As indicated in the introduction, previous studies have suggested that SP-D does not enhance the uptake of some strains of IAV by alveolar macrophages in vitro. In the absence of SP-D, macrophage phagocytosis of IAV was similar to wild type mice suggesting that SP-D is not a critical determinant for macrophage clearance of IAV, in vivo.

Example 27

CD4 and CD8 T Lymphocytes in BALF

Figure 22A:
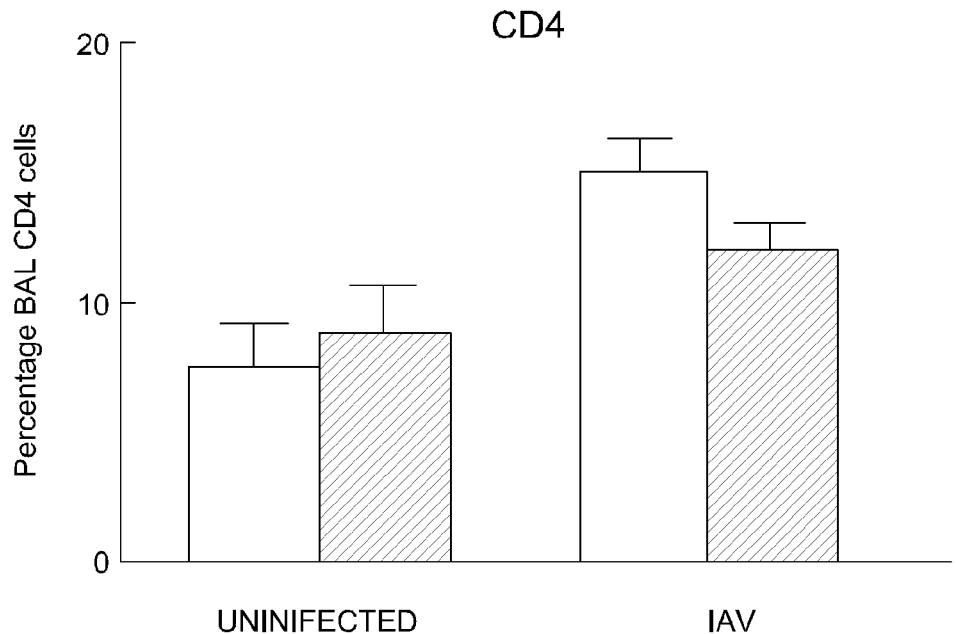
FIGS. 22A and 22B depict either CD4 or CD8 T lymphocytes in BALF after IAV infection, respectively. Three days after IAV infection, CD4 and CD8 T lymphocyte subsets were measured in BALF by flow cytometry with fluorescent isothiocyanate (FITC) conjugated mouse CD4 and phycoerytherin (PE) conjugated mouse CD8 antibodies. There was no difference in the percentage of CD4 (FIG. 22A) and CD8 (FIG. 22B) T lymphocytes in BALF between SP-D −/− (open bar) and SP-D +/+ (hatched bar) mice. CD4 and CD8 T lymphocytes in BALF were similar for uninfected SP-D +/+ and SP-D −/− mice. Data represent mean±SEM with n=8 mice per group, $*p<0.05$ compared SP-D +/+ mice.
Figure 22B:
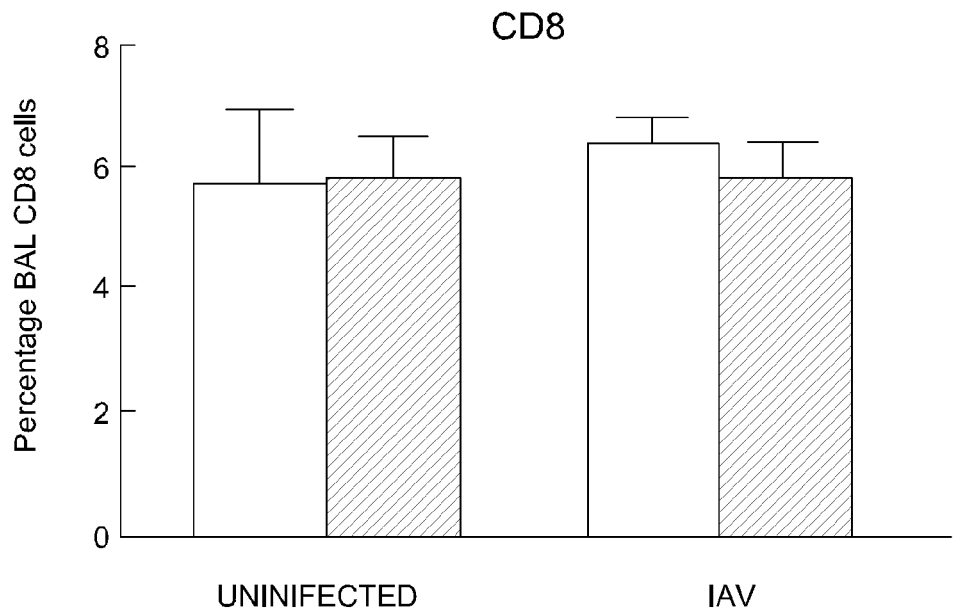

Three days after IAV infection, CD4 (helper T lymphocytes) and CD8 (cytotoxic T lymphocytes) cells were measured in BALF. There was no difference in the percentage of CD4 and CD8 T lymphocytes in BALF between SP-D−/− and SP-D+/+ mice. FIGS. 22A and 22B. The fractions of CD4 and CD8 T lymphocytes in BALF were similar in uninfected SP-D+/+ and SP-D−/− mice, see FIGS. 22A and 22B.

Lung cells were recovered by bronchoalveolar lavage (BAL). Animals were sacrificed as described for viral clearance and lungs were lavaged three times with 1 ml of sterile PBS. The fluid was centrifuged at 2000 RPM for 10 minutes, resuspended in 600 of PBS, total cells stained with trypan blue and counted under light microscopy. Differential cell counts were performed on cytospin preparations stained with Diff-Quick (Scientific Products, McGaw Park, Ind.).

CD4 and CD8 T lymphocytes were measured after intranasal IAV infection, staining of cells in BALF with fluorescent antibodies, followed by evaluation of cell-associated fluorescence by flow cytometry. Three days after infection, cells from BAL fluid were incubated in buffer (PBS, 0.2% BSA fraction V, 0.02% sodium azide) with rat anti-mouse CD16/CD32 antibodies (Fc Block), FITC conjugated mouse CD4 and phycoerytherin (PE) conjugated mouse CD8 antibodies (Pharmingen, San Diego, Calif.) for one hour on ice and washed two times in fresh buffer. Cell associated fluorescence was measured on a FACScan flow cytometer, using CELLQuest software (Becton Dickinson, San Jose, Calif.). For each sample, 20,000 cells were counted and the results expressed as the percentage CD4 and CD8 T lymphocytes in BALF.

Cytotoxic T cells play an important role in IAV clearance form the lung by direct cytolysis of virus-infected cells. In vitro, SP-D inhibits IL-2 dependent, mitogen-stimulated, T lymphocyte proliferation. However, the results showed that in the absence of SP-D, the percentage of CD4 and CD8 T lymphocytes in BALF were similar to that in wild type mice after IAV infection. Although the current study examined the number of T lymphocytes present in BAL fluid following IAV infection; the function and activation state of the T lymphocytes were not examined.

In Example 28, the effect of SP-D on the myeloperoxidase (MPO) activity in neutrophils was examined.

Example 28

Decreased Neutrophil MPO Activity in SP-D −/− Mice

Figure 23:
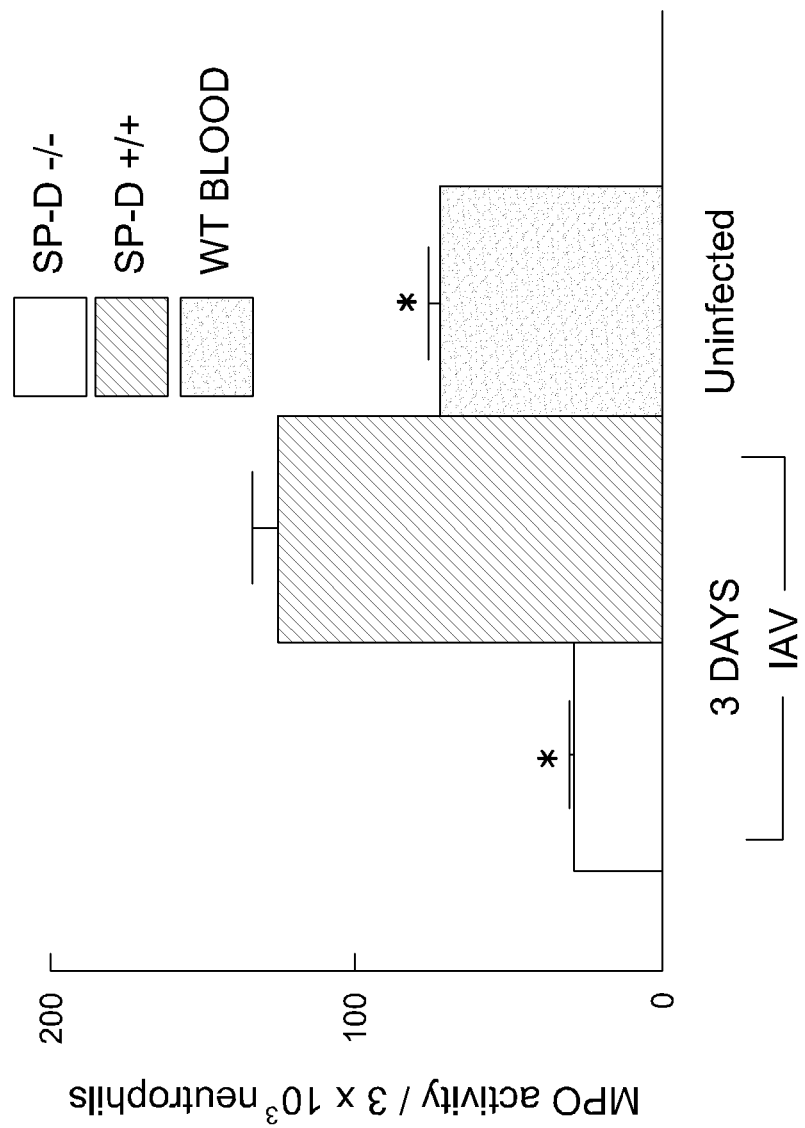
FIG. 23 shows neutrophil myeloperoxidase activity was decreased from SP-D −/− mice: Myeloperoxidase activity was measured in BAL neutrophils 3 days after intranasal infection with IAV at a concentration of $10^6$ ff. Isolated blood neutrophils from uninfected wild type mice were used as controls. Neutrophils were lysed to allow release of MPO from the granules and the MPO activity measured as described in the methods. MPO activity from BAL neutrophils was significantly decreased in SP-D −/− (open bar) compared to SP-D +/+ (hatched bar) mice 3 days after IAV infection. Blood neutrophils from uninfected SP-D +/+ (solid bar, WT blood) mice had significantly greater MPO activity compared to SP-D −/− BAL neutrophils and less MPO activity compared to SP-D +/+BAL neutrophils after infection. Data represent mean±SEM with n=8 mice per group, $*p<0.05$ compared to SP-D +/+.

Myeloperoxidase (MPO) is stored in specific granules of neutrophils. As one measure of neutrophil function, the levels of MPO associated with neutrophils recovered in lung lavage was determined. After IAV infection, MPO activity from isolated BAL neutrophils was significantly decreased in SP-D−/− compared to SP-D+/+ mice, FIG. 23. Control neutrophils isolated from the blood of uninfected SP-D+/+ mice had significantly greater MPO activity compared to BAL neutrophils from IAV infected SP-D−/− mice and significantly less MPO activity compared to BAL neutrophils from IAV infected SP-D+/+ mice, see FIG. 24.

Myeloperoxidase activity was measured in BAL neutrophils 3 days after intranasal infection with IAV at a concentration of $10^6$ ff. A higher concentration of virus was used to provide adequate neutrophils to study. BALF from three wild type mice was pooled to provide sufficient neutrophils, whereas a single SP-D−/− mouse was used. Blood obtained from uninfected SP-D+/+ mice was separated on a gradient of neutrophil isolation medium (NIM-1, Cardinal Associates, Santa Fe, N. Mex.) to isolate blood neutrophils. Neutrophils were added to homogenate buffer (100 mM sodium acetate, pH 6.0; 20 mM ethylenediaminetetraacetic acid [EDTA] pH 7.0; 1% hexadecyl trimethylammonium bromide [HETAB]) in a 96 well microtiter plate in a final volume of 50 µl. The neutrophil mixtures were incubated at 37° C. for 1 hour to lyse the neutrophils and allow release of MPO from the granules. Assay buffer (100 µl) containing 1 mM $H_2O_2$, 1% HETAB, 3.2 mM 3,3'5,5'-tetramethylbenzidine (TMB) was added to each well and readings were taken at 650 nm using a THERMOMAX microplate reader for a period of 4 min. Readings were the average of at least 3 individual wells and MPO activity was reported as maximum MPO activity/4 minutes/$10^3$ neutrophils.

After IAV infection, pulmonary neutrophil accumulation was greater in SP-D −/− mice then in wild type mice. However, neutrophil myeloperoxidase activity normalized per cell was decreased after IAV infection in the SP-D deficient mice. Because the levels were normal in blood neutrophils, it is likely that the recruited cells had undergone a greater degree of degranulation in response to the viral challenge in the absence of SP-D. Defects in neutrophil chemotactic, oxidative and bacterial killing functions have been documented in IAV infection. In addition, it has been shown in animal models that there is a correlation between impairment of function of these cells and predisposition to bacterial superinfection. SP-D enhances the uptake and specific oxidative response to internalized virus in vitro. In addition, SP-D decreases the inhibitory effects of IAV on the neutrophil respiratory burst responses. Although the effects of SP-D and IAV on neutrophil degranulation and MPO activity have not yet been characterized in vitro, the findings emphasize the potential importance of neutrophils for the initial host response to IAV and suggest that SP-D may alter the neutrophil response to internalized virus.

Example 29

IAV Infection Enhances SP-D Accumulation in the Lung

Figure 24:
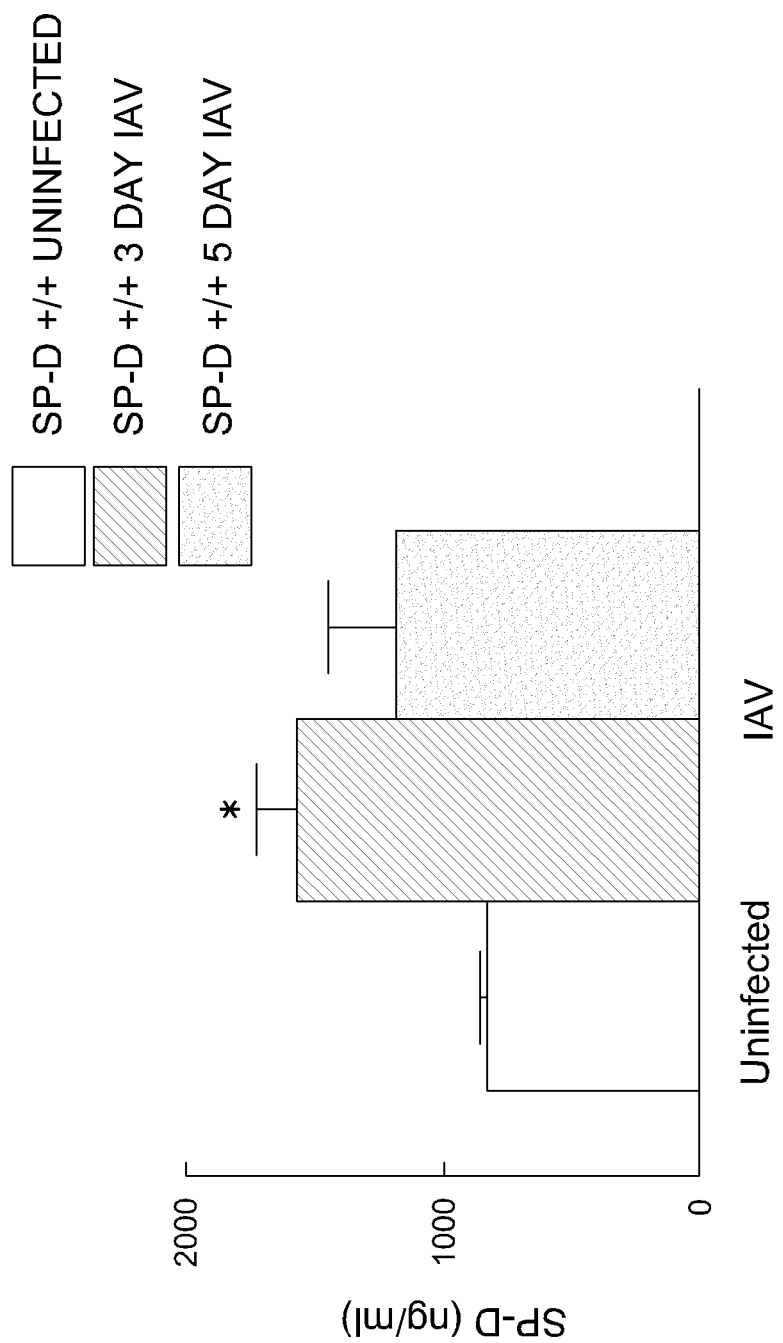
FIG. 24 shows increased SP-D concentrations in the lung following IAV infection: Concentrations of SP-D in lung homogenates were determined with an enzyme-linked immunosorbent assay (ELISA). Three days after IAV infection, SP-D concentrations in the lung of SP-D +/+ (hatched bar) mice were significantly greater compared to uninfected SP-D +/+ (open bar) mice. Five days after IAV infection, SP-D concentrations in the lung of SP-D +/+ mice (solid bar) decreased to levels similar to uninfected SP-D +/+ mice. Data represent mean±SEM with n=10 mice per group, *p<0.05 compared to uninfected SP-D +/+ mice.

Concentrations of SP-D in lung homogenates were increased approximately two fold 3 days following IAV infection in SP-D+/+ mice, see FIG. 24. Five days after IAV infection, SP-D concentrations in the lung of infected SP-D+/+ mice decreased to concentrations similar to uninfected SP-D+/+ mice.

Concentrations of SP-D in lung homogenates were determined with an enzyme-linked immunosorbent assay (ELISA). Three and 5 days after infection with IAV, lungs from infected and uninfected wild type mice were removed and homogenized in 2 ml of PBS. The surfactant protein D concentrations were measured in a double antibody ELISA using rabbit and guinea pig anti-SP-D sera. Each assay plate included a standard curve generated with purified mouse SP-D. All samples were run in duplicate and the concentrations of the samples were calculated by graphing absorbance vs. concentrations of the standard.

SP-D Regulates NF-KB and Matrix Metalloproteinase Production in Alveolar Macrophages Via Oxidant-Sensitive Pathways Targeted gene inactivation of the SP-D gene in mice caused the accumulation of surfactant phospholipids, emphysema, and increased numbers of lipid-laden, foamy alveolar macrophages. Emphysema in SP-D (−/−) mice was associated with increased production of matrix metalloproteinases (MMPs)-2,9,12, hydrogen peroxide ($H_2O_2$), and increased proinflammatory cytokine production following pulmonary infection. While focal production of cytokines, MMPs and $H_2O_2$ may play a role in the development of emphysema in SP-D (−/−) mice, the mechanisms mediating the generation of these molecules have not been identified.

Reactive oxygen species (ROS), including superoxide anion ($O_2^-$), hydroxy radical (OH.), and hydrogen peroxide ($H_2O_2$) have been implicated in the pathogenesis of several lung diseases associated with oxidative stress, including emphysema, adult respiratory distress syndrome, asthma, and lung fibrosis. While ROS play a critical role in host defense, increased ROS generated during acute and chronic inflammation can be cytotoxic, causing oxidative damage to various macromolecules, lipid peroxidation, protein crosslinking, protein fragmentation, DNA damage and strand breaks. Oxidative stress has been associated with activation of transcriptional pathways mediating cellular responses to infection and injury. For example, activity of nuclear factor-κB (NF-κB) and activator protein-1 (AP-1), were stimulated by oxidative stress. Binding sites for NF-κB and AP-1 were identified in the promoters of numerous genes, including proinflammatory cytokines. Likewise, cis-acting elements binding NF-κB and/or AP-1 were present in the promoter regions of the MMP-2, 9, and 12 genes. Therefore, it was hypothesized herein that reactive oxygen species, generated by AMs in SP-D (−/−) mice, might activate redox-sensitive transcription factors, causing increased expression of the MMPs. In the present study, increased ROS were demonstrated in lungs of SP-D (−/−) mice. MMP-2 and MMP-9 production by alveolar macrophages from SP-D (−/−) mice was stimulated by oxidant sensitive pathways including NF-κB activation.

EXAMPLES

In Examples 30-34, the effect of SP-D on metalloproteinase production in alveolar macrophages was assessed. The SP-D(−/−) mouse was used as a model for emphysema and the SP-D (+/+) was compared. Results are presented as means±standard error (SE). Comparison was made by Student's t test. Statistical calculations were performed with the Statview II statistical package (Abacus Concepts, Berkeley, Calif.). A value of P<0.05 was regarded as significant.

SP-D (−/−) mice used in the Examples were generated by targeted gene inactivation as in Example 1.

Isolation of alveolar macrophages (AMs) from bronchoalveolar lavage (BAL) was performed by instilling ten, 1 ml aliquots of phosphate-buffered saline (PBS). BAL fluid from several animals was pooled to provide sufficient numbers of macrophages for each analysis. The lavage was centrifuged at 1200 rpm at 7 min and pelleted cells were resuspended in serum-free RPMI medium containing 1% of Nutriodoma (Boehringer Mannheim, Indianapolis, Ind.), and counted with a hemocytometer. More than 90% of BAL cells were AM in both WT and SP-D (−/−) mice. For some experiments, alveolar macrophages (AMs) were isolated by differential attachment to tissue culture flasks at 37° C. Non-adherent cells were then removed, and fresh, serum-free medium was added. The adherent AMs were maintained in a humidified atmosphere containing 5% $CO_2$ and 95% air until the end of the experiments.

The experiments in Examples 30-32 show that the SP-D signalling is regulates oxidant production or clearance of reactive oxygen species (ROS) by Alveolar macrophages in the lung and that the signalling occurs through the NF-κB pathway. More specifically, SP-D acts by inhibiting the action of NF-κB.

Thus, a method for the treatment of pulmonary diseases associated with over-activation of NF-κB is provided which uses SP-D as an inhibitor is provided. The SP-D can be administered in any of the ways used previously herein or outlined in Examples 9-12.

Example 30

Increased Oxidant Stress in Lungs of SP-D (−/−) Mice

Figure 25:
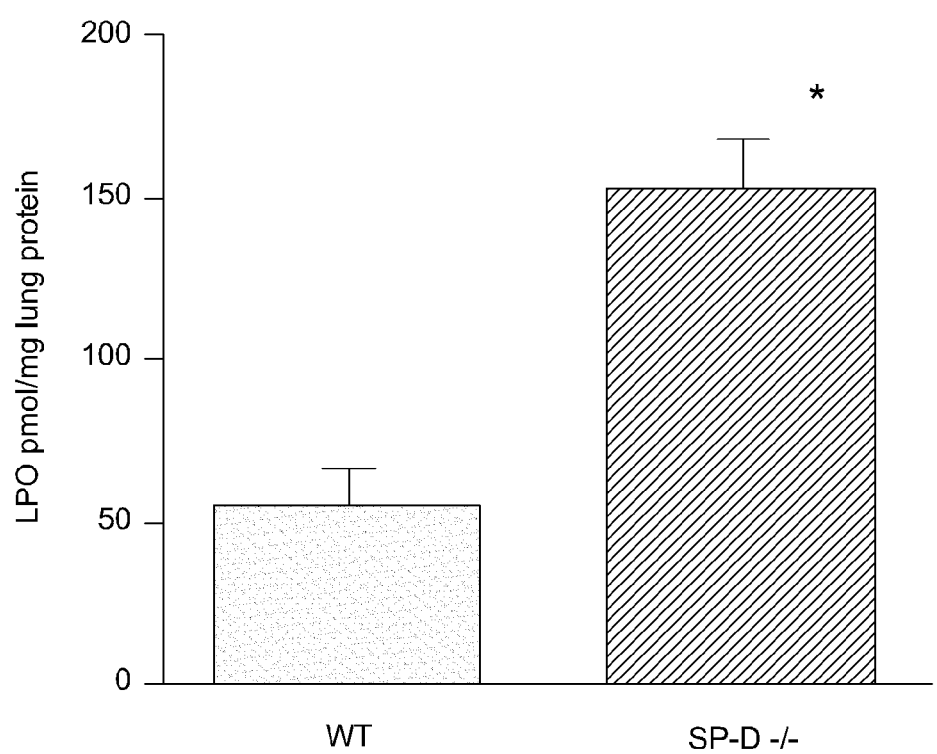
FIG. 25. Lung lipid hydroperoxidase concentrations are increased in lungs of SP-D(−/−) mice. Lung tissues from adult WT and SP-D (−/−) mice were homogenized, and the content of malonaldehyde and 4-hydroxyalkanels measured colorimetrically. LPO was significantly increased in lungs from SP-D (−/−) mice. Values shown are means±SE, n=5, *p<0.05.

To determine whether oxidant stress was increased in the lungs of SP-D (−/−) mice, lipid peroxide (LPO) concentrations were assessed. Lipid hydroperoxide (LPO) concentration was measured in whole lung from SP-D (−/−) and wild type mice using the LPO-586 assay kit (OXIS International, Inc., Portland, Oreg.). Lungs were isolated and homogenized with PBS containing 5 mM butylated hydroxytoluene (BHT) and centrifuged at 15000 rpm for 15 min at 4° C. Supernatants were collected and the content of malonaldehyde and 4-hydroxyalkenals was measured colorimetrically using manufacture's procedures. LPO content of lung homogenates was significantly increased in lungs of SP-D (−/−) compared to those from wild type mice (see FIG. 25).

Figure 26A:
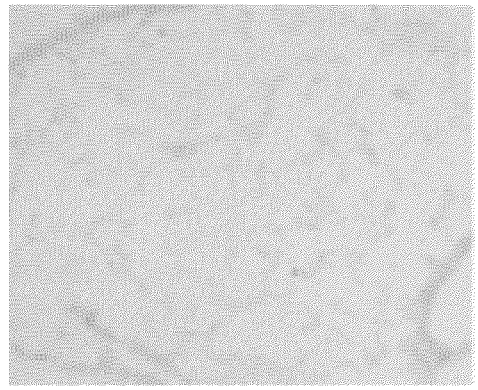
FIGS. 26A and 26B depict frozen sections of lung from either WT or SP-D (−/−) mice, respectively. Increased reactive carbonyls in lungs of SP-D (−/−) mice. Frozen sections of lung from WT and SP-D (−/−) mice were incubated with OHNAH, followed by coupling with diazonium. Reactive carbonyls were observed at the sites of foamy alveolar macrophage infiltration in SP-D (−/−) (FIG. 26B) but not in control mice (FIG. 26A). Figures are representative of three separate experiments.
Figure 26B:
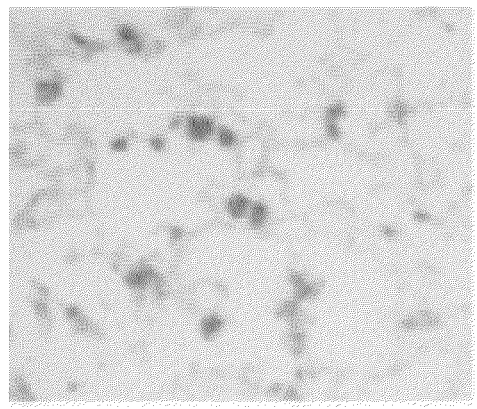

Histochemical detection of lipid peroxidation-derived carbonyls was performed as follows: lung sections (10 μm thick) obtained from frozen tissue specimens were exposed 1 hour at 60° C. to a 0.1% 3-OH-2-naphtoic acid hydrazine (OHNAH) solution in 50% ethanol containing 5% acetic acid. After the reaction, the sections were washed thoroughly in 50% ethanol and stained 5-10 minutes with a 0.1% fast blue B solution in an alcoholic buffer prepared by mixing equal volumes of 100 mM phosphate buffer, pH 7.4, and 95% ethanol. Carbonyls were converted to naphtoic hydrazones by reaction with OHNAH. Coupling with the diazonium salt then yielded violet azo dyes. Histochemical staining with OHNAH tetrazolium demonstrated increased staining in lung sections from SP-D (−/−) mice. The intensity of OHNAH staining in SP-D (−/−) mice was not uniform, being most prominent at the sites of foamy macrophage infiltration (see FIGS. 26A and 26B).

Figure 27A:
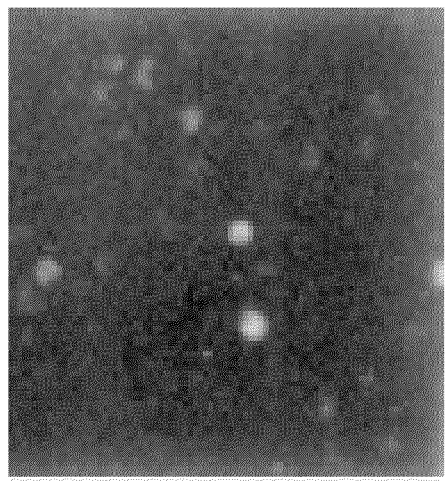
FIGS. 27A and 27B depict AMs from either wild type or SP-D (−/−) mice incubated with CD-CFH for 30 min, respectively. Increased intracellular ROS in alveolar macrophages from SP-D (−/−) mice. Increased fluorescence was observed in AMs from SP-D (−/−) mice (FIG. 27B) compared to those from controls (FIG. 27A). Data are representative of three separate experiments.
Figure 27B:
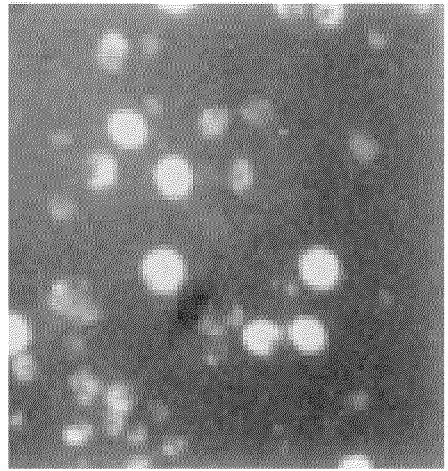
Figure 29A:
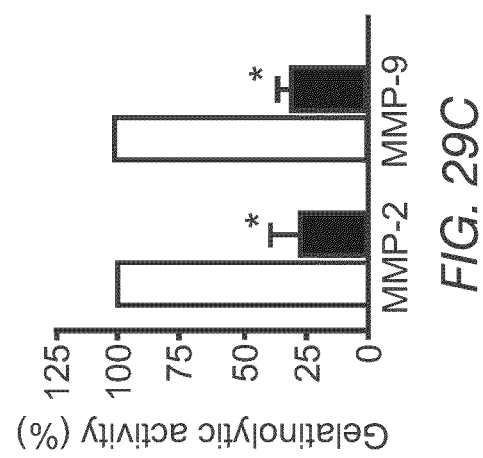
FIGS. 29A, 29B, 29C, and 29D depict effects of antioxidants on MMP expression by AMs from SP-D (−/−) mice. Alveolar macrophages were isolated from SP-D (−/−) mice and treated with 20 mM N-acetylcysteine (NAC) or 200 μM pyrrolidine dithiocarbamate (PDTC). Conditioned media from the AMs were collected after 24 hrs incubation and MMP-2 and 9 activity determined by gelatin zymography. Both NAC (FIG. 29A) and PDTC (FIG. 29B) inhibited gelatinolytic activities of MMP-2 and 9 in the conditioned media from SP-D (−/−) mice. Figures are representative of at least 3 independent experiments. Densitometric analysis of gelatinolytic activity with (solid bar) or without (open bar) treatment showed that both NAC (FIG. 29C) and PDTC (FIG. 29D) significantly inhibited gelatinolytic activities of MMP-2 and 9 in the conditioned media from SP-D (−/−) mice. Values were normalized to matched untreated control±SE, n=3, *p<0.05.
Figure 29C:
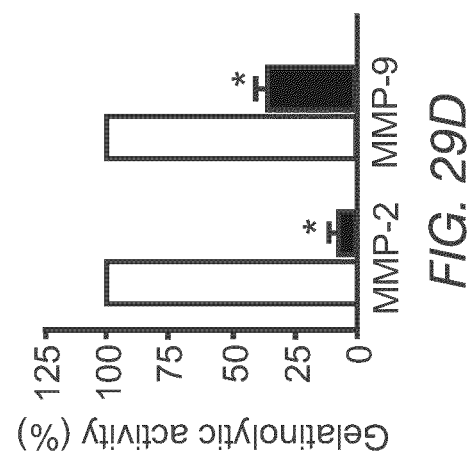
Figure 29B:
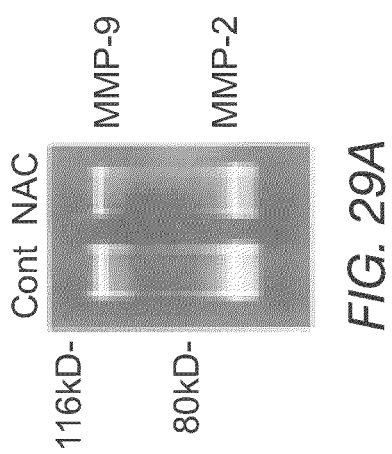
Figure 29D:
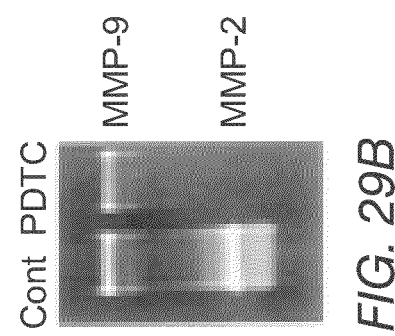

Intracellular reactive oxygen species (ROS) in AMs were determined using CDCFH, an indicator of intracellular peroxides, including $H_2O_2$ and lipid peroxides. CDCFH, 6-carboxy-2',7'-dichlorodihydrofluorescein diacetate (Molecular Probes, Inc., Eugene, Oreg.) is a fluorescent probe. To allow staining, AMs were incubated with 10 μM CDCFH for 30 min, rinsed with PBS, and fixed with 4% paraformaldehyde. Fluorescence was observed with fluoromicroscopy using excitation and emission wavelengths 485 and 530 respectively. Increased CDCFH fluorescence was observed in AMs from SP-D (−/−) compared to those from control mice (FIGS. 27A and 27B). Taken together with previous findings, this demonstrates increased hydrogen peroxide production by AMs from SP-D (−/−) mice, the present data support the concept that oxidative stress is increased in pulmonary tissues in the absence of SP-D.

Example 31

Activation of NF-κB in SP-D (−/−) Mice

ROS activate redox-sensitive transcription factors including NF-κB and AP-1. Thus, it was of interest to determine whether the presence of SP-D correlated with production of either of these transcription factors. Immunostaining for NF-κB p65 was performed as follows: BAL cells were isolated from wild type and SP-D (−/−) mice, cytospun and fixed with cold methanol for 10 min, and washed in PBS. The slides were then incubated at 4° C. overnight with a rabbit anti p65 antibody (Santa Cruz Biotechnology, Santa Cruz, Calif.). After incubation, the slides were washed in PBS and incubated with fluorescein isothiocyanate (FITC)-conjugated goat anti rabbit IgG (Santa Cruz Biotechnology) as a second antibody, and compared to samples prepared identically without primary antibody.

Immunofluorescence staining analysis with anti-NF-κB p65 antibody demonstrated that the p65 subunit of NF-κB was present in the cytoplasm of AMs from both wild type and SP-D (−/−) mice (FIG. 28A). However, in AMs from SP-D (−/−) mice, increased staining for NF-κB p65 was observed;

furthermore, nuclear staining was markedly increased in AMs from SP-D (−/−) mice and was almost never detected in AMs from WT mice. NF-κB activity was determined in nuclear extracts from SP-D (−/−) mice by assessing binding to a consensus NF-κB oligonucleotide in EMSA (FIG. 28B). Increased NF-κB binding was observed in nuclear extracts from AMs of SP-D (−/−) mice. Binding of the nuclear extract to the NF-κB site was inhibited by co-incubation with the unlabeled NF-κB oligonucleotide, supporting the specificity of the EMSAs. Likewise, AP-1 binding activity was increased in nuclear extracts from AMs of SP-D (−/−) mice. Supershift assay for NF-κB showed that the protein/DNA complex contained both components of NF-κB p50 and p65, but not c-Rel (FIG. 28C).

Thus, SP-D deficiency caused increased oxidative stress in pulmonary tissues associated with redox-sensitive enhancement of NF-κB activity, and increased metalloproteinase production by AMs. Since NF-κB is a critical mediator of transcriptional responses during inflammation, these findings support the concept that SP-D regulates both oxidant production and inflammatory responses by AMs. SP-D suppresses steady state NF-κB activation and metalloproteinase expression that may contribute to the emphysema characteristic of SP-D (−/−) mice. The increased nuclear translocation and activity of NF-κB seen in the AMs from SP-D (−/−) mice may influence the heightened inflammatory responses of AMs from these mice during pulmonary infections.

Increased oxidative stress in the lungs of SP-D (−/−) mice was supported by the increased production of reactive oxygen species by AMs, increased content of oxidized lipid species, reactive carbonyls, and CDCFH fluorescence. However, the mechanism underlying the oxidative stress in the lungs of SP-D (−/−) mice, remains unclear, and may relate either to increased oxidant production, decreased antioxidant activity, or failure to clear reactive oxygen species. The present studies support the concept that NF-κB activation by AMs was mediated, at least in part, by apocynin and DPI sensitive pathways, supporting a role of NADPH oxidase or other oxidases in the process. Recently NF-κB activation pathway by NADPH oxidase in alcoholic liver injury was also reported. However the specificity of these inhibitors for various oxidases has not been established. Indeed, DPI inhibits a wide range of flavoproteins including NADPH oxidase and complex I within the mitochondrial electron transport chain. Therefore, it is possible that pathways other than NADPH oxidase are involved in this process. Recent studies by Bridges et al. also demonstrated that SP-A and SP-D prevented oxidation of unsaturated phospholipids in vitro supporting a direct antioxidant function for these proteins. This activity may be particularly important in the lungs of SP-D (−\−) mice, wherein concentrations of alveolar lipids are markedly increased and concentrations of SP-A are relatively low. Large aggregate surfactant from SP-D (−\−) mice contained increased lipid peroxide species, perhaps reflecting increased oxidant production or decreased oxidant clearance by the lung.

Example 32

Antioxidants Inhibit MMP Expression by AMs from SP-D (−/−) Mice

To determine whether increased oxidant production mediated the expression of MMPs by AMs from SP-D (−/−) mice, the cells were treated with N-acetylcysteine (NAC) and pyrrolidine dithiocarbamate (PDTC), both antioxidant reagents as follows: AMs from SP-D (−/−) mice were pooled and placed in culture at a concentration of $5 \times 10^5$ cells per well in serum-free RPMI medium. The AMs were treated with 20 mM N-acetylcysteine (NAC), 200 µM pyrolidine dithiocarbamate (PDTC), 1 µM diphenylene iodonium chloride (DPI) (Sigma, St. Louis, Mo.), or 1 mM apocynin (Aldrich, Milwaukee, Wis.). Cells were also incubated with a 10 µM SN-50 (Calbiochem, LaJolla, Calif.), an inhibitor of NF-κB nuclear import. After 6 h incubation, supernatants were removed and the cells were washed and incubated with fresh media including the reagents for 24 h. At the concentrations used, these agents did not alter macrophage viability, as determined by trypan blue exclusion or LDH measurement (Roche, Indianapolis, Ind.). RAW 264.7 murine macrophage cell line was obtained from the American Type Culture Collection (Rockville, Md.) and maintained in DMEM containing 10% FBS, 10 mM HEPES, 50 U/ml penicillin and 50 µg/mL streptomycin. $2 \times 10^5$ cells in 24-well plates were incubated with or without 10 µM menadione (Sigma, St. Louis, Mo.) for 24 hours.

Gelatinolytic activity in the culture media of untreated and treated cells was analyzed by SDS-PAGE zymography (FIGS. 29A-29D). Gelatin Zymography was performed as follows: MMP activities were measured in macrophage-conditioned media. Proteinases in the conditioned media were concentrated by incubation with gelatin-agarose beads (Amersham Pharmacia, Arlington Heights, Ill.) for 2 h at 4° C. The beads were pelleted and washed, and proteinases eluted by incubation in sample buffer for 45 min at 37° C. The samples then were electrophoresed into 10% Zymogram gelatin gels (NOVEX, San Diego, Calif.). After electrophoresis, gels were washed twice with 2.5% Triton X-100 (37° C., 30 min) and incubated for 16 h with 40 mM Tris-HCl (pH 7.5), 10 mM $CaCl_2$, and 1 µM $ZnCl_2$. Gels were stained with 0.5% (wt/vol) Coomassie blue in 50% methanol and 10% acetic acid for 30 min, then destained. MMPs were detected as clear bands against a blue background.

Treatment of AMs from SP-D (−/−) mice with NAC and PDTC reduced gelatinolytic activity consistent with mobility of MMP-2 and 9. Since NADPH oxidases are important sources of ROS in macrophages, it was assessed whether ROS generated by NADPH oxidases or other oxidases mediated the increased MMP expression characteristic of SP-D (−/−) mice. AMs from SP-D (−/−) mice were incubated with NADPH oxidase inhibitors, diphenyleneiodonium chloride (DPI) and apocynin. SDS-PAGE-zymography demonstrated that both of NADPH oxidase inhibitors markedly suppressed MMP enzymatic activity (FIG. 30A) Likewise, apocynin reduced MMP-2 and 9 mRNA in cultured AMs from SP-D (−/−) (FIG. 30B).

To assess whether apocyanin affected binding of nuclear extracts, the following protocol was used: Nuclear extracts were obtained using a modified method previously described (Sever Chroneos, et al. Am. J. Physiol. 277:L79). Lavaged cells were lysed with Buffer A (10 mM Hepes, 10 mM KCl, 0.1 mM EDTA, 1.5 mM $MgCl_2$, 0.2% Nonidet P-40 (NP-40), 1 mM DTT, 0.5 mM PMSF), followed by vortexing to shear the cytoplasmic membranes. Nuclei were pelleted by centrifugation at 3000 rpm for 3 min at 4° C. in a microcentrifuge. Nuclear proteins were extracted with high-salt buffer C (20 mM Hepes, 25% glycerol, 1.5 mM $MgCl_2$, 0.1 mM EDTA, 1.5 mM $MgCl_2$, 420 mM NaCl, 1 mM DTT, 0.5 mM PMSF) and stored at −80° C. Total nuclear protein concentrations were determined by bicinchoninic acid (BCA) method.

Figure 31A:
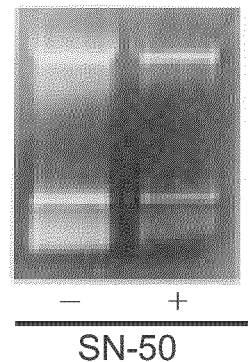
FIGS. 31A and 31B depict SN-50 inhibits MMP expression by AMs from SP-D (−/−) mice. AMs isolated from SP-D (−/−) mice were treated with SN-50, a synthetic NF-κB inhibitory peptide. Conditioned media from the AMs was subjected to zymography in gelatin substrate. SN-50 significantly reduced gelatinolytic activities of MMP-2 and 9 (FIG. 31A). The zymogram is representative of three separate experiments. Densitometric analysis of gelatinolytic activity with (solid bar) or without (open bar) treatment showed that SN-50 inhibited gelatinolytic activities of MMP-2 and 9 in the conditioned media from SP-D (−/−) mice (FIG. 31B). Values were normalized to matched untreated control±SE, n=3, *p<0.05.
Figure 31B:
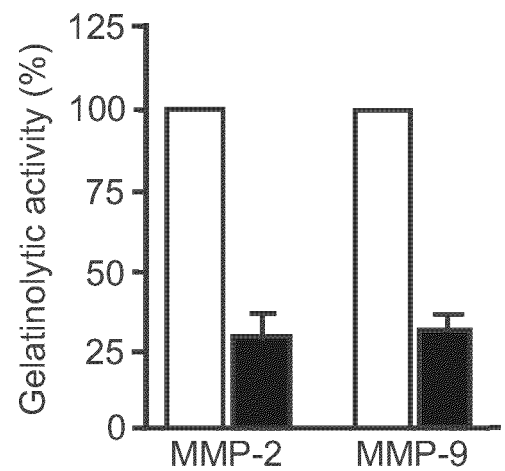

Apocynin reduced binding of nuclear extracts from AMs isolated from SP-D (−\−) mice to a NF-κB oligonucleotide (FIG. 30C). Apocynin also decreased DNA binding activity to an AP-1 oligonucleotide. AMs were cultured with SN-50, a synthetic inhibitory peptide that blocks nuclear import of NF-κB. SN-50 markedly suppressed MMP-2 and 9 production by AM from SP-D (−/−) mice (FIGS. 31A and 31B).

To assess whether ROS directly stimulated MMP production, RAW 264.7 macrophages were incubated with 10 μM of menadione, a ROS generator, for 24 hours. MMP-9 production was increased by menadione as assessed by zymography.

Foamy macrophages are a prominent feature of the lung pathology in SP-D (−\−) mice. The increased oxidant production and foamy alveolar macrophage formation seen in SP-D (−\−) mice are reminiscent of findings in atheromas, wherein uptake of oxidized lipids by tissue macrophages further induced reactive oxygen species, and enhanced macrophage activation. While lung lipid concentrations are markedly increased in SP-D (−/−) mice, it is not likely that increased lipid content alone is a sufficient stimulus to generate the activated foamy macrophages. Indeed, similarly increased surfactant lipid concentrations and foamy macrophages were observed in GM-CSF and common B chain receptor deficient mice without the increased oxidant production or alveolar macrophage activation seen in the SP-D (−/−) mice. Taken together, the present findings support the concept that SP-D signaling is required for the regulation of oxidant production or clearance of ROS by AMs in the lung. Recent findings that SP-D binds to CD14 via its carbohydrate recognition domain, inhibiting CD14 lipopolysaccharide (LPS) interactions, suggests a mechanism by which alveolar macrophage activity may be modulated by SP-D. Since LPS-CD14 interactions may also influence NADPH oxidase and NF-κB, these pathways may mediate the increased inflammatory responses seen during pulmonary infections in the SP-D (−/−) mice. It was also observed herein that the addition of mouse (5 μg/ml) SP-D in vitro, did not reduce MMP production by AMs from SP-D (−/−) mice. This finding suggests that direct signaling via SP-D was not sufficient to inhibit MMP production by AMs from SP-D (−/−) mice in vitro, and that activation of AMs may be mediated indirectly by chemical messengers generated in the lungs of SP-D deficient mice.

SP-D plays an important role in the modulation of pulmonary infection, caused by numerous pathogens. SP-D binds to various microorganisms and their products, including gram-negative and gram-positive bacteria, respiratory viruses, fungi, and endotoxin. In vitro studies support the role of SP-D in the binding and aggregation of pathogens, enhancing their phagocytosis and killing. Paradoxically, in the presence of some pathogens, oxidant production and killing by AMs in vitro was increased by SP-D, findings that contrast with the marked activation of endogenous oxidant production seen in AMs from the SP-D deficient mice. Thus SP-D actions on effector cells may be mediated by complex interactions among various receptors that may uniquely recognize the pathogen, SP-D-pathogen complexes, or SP-D. Since SP-D also binds to various lipid components, including phosphatidylinositol and glucosylceramide, known second messengers involved in inflammatory responses, SP-D may also indirectly influence cell signaling by interacting with such molecules.

The work set out in Examples 30-32 demonstrates that the excess reactive oxygen species generated in the absence of SP-D, activate the redox sensitive transcription factor, NF-κB. Thus, SP-D appears to play a central role in the regulation of NF-κB activity in AMs. Since NF-κB regulates numerous proinflammatory response genes expressed by AMs, including IL-1β, TNF-α, IL-6, MIP-2, and metalloproteinases-9, SP-D dependent pathways may be important modulators of the general response of the AM to infection and inflammation. Indeed, in recent studies, increased production of the cytokines TNF-α, IL-6, and IL-1β was observed following pulmonary infection by bacterial pathogens in SP-D (−/−) mice, supporting the concept that SP-D orchestrates both steady state and infection induced proinflammatory cytokine production by AMs.

In the present studies, SN-50, a selective NF-κB inhibitor, suppressed MMP-2, MMP-9 production. SN-50 is known to inhibit nuclear import of NF-κB, thereby inhibiting its transcriptional activity. An NF-κB element is present in the promoter region of the MMP-9 gene, supporting the concept that SN-50 may suppress MMP-9 production by blocking NF-κB activity. However, NF-κB binding sites have not been detected in the promoter region of the MMP-2, and it is unclear whether the inhibitory effects of SN-50 on MMP-2 production are regulated by direct or indirect effects on MMP-2 transcription. Alternatively, NF-κB may bind to and enhance expression of other transcription factors, including AP-1 and p53, that may increase MMP-2 expression directly or through protein-protein interactions. Finally, SN-50 shares the nuclear localization sequence which competes for the nuclear import of endogenous NF-κB. The specificity of SN-50 for NF-κB nuclear import has been questioned since other nuclear proteins share this nuclear import system. Nonetheless, present findings support the concept that SP-D plays a central role in the modulation of metalloproteinase expression in AMs by influencing NF-κB activity.

The present study demonstrates an oxidant dependent activation of NF-κB and enhanced metalloproteinase expression by AMs from SP-D (−/−) mice that may be involved in the pathogenesis of emphysema characteristic of this model. Oxidants derived from air pollution, cigarette smoking, and activated inflammatory cells have been implicated in the pathogenesis of emphysema in human lung disease. Findings that SP-D concentrations are reduced in lung lavage from smoking individuals and patients with cystic fibrosis supports a potential role for SP-D in the regulation of oxidant induced lung inflammation.

Example 33

Treatment of Colds and Flu and their Symptoms with SP-D

Because SP-D has a role in both the clearance of virus from the lungs and the reduction in inflammation, it is well-suited for use in the treatment of the infection and symptoms of colds and flus. Many patients experience continued coughing and discomfort even after the clearance of virus from the body. Thus, the use of SP-D allows for suppression of inflammation and, a reduction in the symptoms associated with it. Thus, a patient with the flu is treated with SP-D protein for 1-2 weeks until symptoms completely disappear.

The SP-D protein structure and domains have been characterized, as have many of the collectins (Hansen, et al. Immunobiology 1998 August; 199(2):165-189). The protein is synthesized as dodecamers consisting of four homotrimers each stabilized by disulfide bonds (Zhang, et al. J. Biol. Chem. 2001 Jun. 1; 276(22):19214-19219). Studies have shown that SP-D is a 43 kDa polypeptide with a short NH2-terminal domain, a collagen-like sequence, and a C-terminal lectin domain (Crouch et al. J. Biol. Chem. 1994 Jun. 24; 269(25):17311-17319). The carbohydrate recognition domains have been mapped in detail as have the N-terminal and collagen domains. The carbohydrate recognition domain (CRD) can be expressed as a fusion protein or alone and is still able to bind carbohydrates (Kishore, et al. Biochem J. 1996 Sep. 1; 318(Pt 2):505-511). In addition, chimeric proteins containing various domains from the different collectins have been produced (white, et al. J. Immunol. 2000 Aug. 15; 165 (4):2108-2115). Variants lacking both the amino terminal region and the collagen-like region were generated and analyzed (Ogasawara et al. J. Biol. Chem 1995 Aug. 11; 270(32): 19052-19058). The crystal structure of the trimeric alpha-helical coiled coil and the lectin domains of the SP-D protein have been analyzed (Hakansson, et al. Structure Fold Des. 1999 Mar. 15; 7(3):255-264). Thus, with the extensive characterization of SP-D, chimeras, and variants described in the field, one of skill in the art would be able to use this information to identify active variants of SP-D which would still be active in the methods disclosed herein. Although, variants which are as active or more active are desired, it is envisioned that variants which are 80% or more active would still be useful.

Example 34

SP-D and Active Variants

SP-D variants which are still able to have the activity needed are produced. The activity may be as a surfactant, anti-inflammatory, or activity against infectious agents. In particular, the SP-D is still able to bind to the cell of choice, viruses, fungi, bacteria, or white blood cells. Much is known about the domains and amino acid sequence of the SP-D needed for the specific activities. For example, the ability to bind to allergens, lipopolysaccharides (of Gram negative bacteria), and the interaction with phospholipids is associated with the carbohydrate recognition domains (CRDs). Thus, the CRD is an important domain in the activity of the protein, particularly in binding to bacteria, fungi, and viruses. Variants of SP-D are produced which contain an active CRD. Preferably, the variants are truncated or mutated in regions of SP-D other than the CRD. Variants with minor amino acid changes in the CRD region may be produced, particularly with amino acid changes which do not affect the activity, such as like amino acid changes (basic amino acid to basic amino acid). In addition, chimeras which incorporate domains from other collectins or C-type lectins are envisioned.

The neck region of SP-D is believed to be important as a dimerizing or trimerizing region to bring together three CRDs and allowing multivalency and, thus, strong binding. Thus, bivalent, trivalent, and monovalent variants are envisioned which contain mutations or deletions in the neck region.

Chimeras containing domains from other collectins are envisioned which may, in fact, be more active than wild type SP-D. For example, a chimera of human serum mannose binding lectin (MBL) and SP-D was produced containing the N terminus and collagen domain of human SP-D and the neck region and CRD of human MBL to create a novel collectin. The chimera bound to influenza A virus (IAV), inhibited IAV hemagglutination activity and infectivity, and induced aggregation of viral particles to a much greater extent than MBL (White et al. *J. Immunol.* 2000 Aug. 15; 165(4):2108-15). A second chimera containing bovine serum conglutinin and the amino terminus and collagen domain of rat pulmonary SP-D fused to the neck and CRD of conglutinin also showed a high ability to inhibit IAV infection.

Thus, active variants are variants of SP-D which still possess at least 50% of the activity of wild-type SP-D, preferably 60%, 65%, 70%, 75%, 80%, 85%, 90%, 95%, 100% or more activity. Examples include truncations in which parts of the protein which are not important for activity are removed, point mutations in which parts of the protein which are not necessary for activity are mutated. Particularly advantageous mutations include mutations that either do not change the amino acid coded for or those that change from a like amino acid to a like amino acid, for example a basic amino acid. In addition, clearly the chimera which use domains from other collectins produce highly active versions of SP-D which can be used in the presently claimed invention.

The patient is treated as in Examples 12-14 in which SP-D variant protein of the vectors which express the SP-D variants are administered to the patient as needed until the pathogen is cleared from the body and the symptoms abate. Alternatively, the SP-D variant is administered to a patient with emphysema or other forms of lung abnormalities or pathologies as in Examples 9-11.

Example 35 rhSP-D Treatment in Premature Lambs

Premature lambs were delivered by cesarean section at 130 days' gestational age (GA) (full term is 150 days GA) and tracheostomized as previously described (Kramer B W, et al. Surfactant protein A recruits neutrophils into the lungs of ventilated preterm lambs. *Am J Respir Crit Care Med* 2001; 163:158-165; Ikegami M, et al. Intratracheal recombinant surfactant protein D prevents endotoxin shock in the newborn preterm lamb. *Am J Respir Crit Care Med* 2006; 173:1342-1347). Premature newborn lambs were resuscitated with 100% $O_2$, a peak inspiratory pressure (PIP) of 40 cm $H_2O$, 4 cm $H_2O$ positive end-expiratory pressure (PEEP), and a respiratory rate of 40/min using a pressure-limited ventilator (Sechrist Industries, Anaheim, Calif.). To avoid overstretch of the premature newborn infant lung during manual ventilation, the clinical resuscitation bag has a pressure relief valve set at 40 cm $H_2O$, and therefore PIP for resuscitation was limited to 40 cm $H_2O$.

Premature lambs at 130 days GA require surfactant treatment to survive. At 20 minutes of age, two groups of lambs were treated with SURVANTA® (Abbott Laboratories, Columbus, Ohio) mixed with rhSP-D (+rhSP-D group) or buffer (control group) using two boluses for instillation (Ueda T, et al. Distribution of surfactant and ventilation in surfactant-treated preterm lambs. *J Appl Physiol* 1994; 76:45-55). rhSP-D was synthesized as previously described (Ikegami M, et al. Intratracheal recombinant surfactant protein D prevents endotoxin shock in the newborn preterm lamb. *Am J Respir Crit Care Med* 2006; 173:1342-1347; Ikegami M, et al. Surfactant protein-D and surfactant inhibit endotoxin induced pulmonary inflammation. *Chest* 2007; 132:1447-1454; Ikegami M, et al. Surfactant protein-D regulates the postnatal maturation of pulmonary surfactant lipid pool sizes. *J Appl Physiol* 2009; 106:1545-1552). Seven milli-grams of rhSP-D in 5 ml buffer (20 mM Tris, 200 mM NaCl, 1 mM ethylenediaminetetraacetic acid, pH 7.4) or 5 ml buffer alone were mixed with a clinical treatment dose of SURVANTA® (100 mg/4 ml/kg)—amounts that are similar to both SP-D and surfactant lipid pool sizes in the normal term newborn lung (Ikegami M, et al. Surfactant protein-D regulates the postnatal maturation of pulmonary surfactant lipid pool sizes. *J Appl Physiol* 2009; 106:1545-1552; Ikegami M, Jobe A H. Surfactant metabolism. *Semin Perinatol* 1993; 17:233-240). After surfactant treatment, the PIP was decreased to regulate tidal volume ($V_T$) at 8 to 9 ml/kg (Bicore Monitoring Systems, Anaheim, Calif.), and $F_{iO2}$ was adjusted to maintain a target $P_{O2}$ of 100 to 150 mm Hg. Ventilatory rate, inspiratory time of 0.6 seconds, and PEEP were not changed.

A five hour study period was chosen to detect changes in proinflammatory cytokine mRNAs induced by initial ventilation (Naik A S, et al. Effects of ventilation with different positive end-expiratory pressures on cytokine expression in the preterm lamb lung. *Am J Respir Crit Care Med* 2001; 164:494-498). After five hours, lambs were ventilated with $F_{iO2}=1$ for five minutes, then given 100 mg pentobarbital intravascularly, after which the endotracheal tube was clamped to permit oxygen absorption atelectasis (Ikegami M, et al. Intratracheal recombinant surfactant protein D prevents endotoxin shock in the newborn preterm lamb. *Am J Respir Crit Care Med* 2006; 173:1342-1347; Ikegami M, Jobe A. Postnatal lung inflammation increased by ventilation of preterm lambs exposed antenatally to *E. coli* endotoxin. *Pediatr Res* 2002; 52:356-362). After the thorax was opened, the deflation limb of pressure-volume curve was measured (Kramer B W, et al. Surfactant protein A recruits neutrophils into the lungs of ventilated preterm lambs. *Am J Respir Crit Care Med* 2001; 163:158-165; Ikegami M, et al. Intratracheal recombinant surfactant protein D prevents endotoxin shock in the newborn preterm lamb. *Am J Respir Crit Care Med* 2006; 173:1342-1347). Lung tissue of the right lower lobe was frozen in liquid nitrogen for RNA isolation and measurement of neutrophil elastase (NE) activity (Lowry O H, et al. Protein measurement with the Folin phenol reagent. *J Biol Chem* 1951; 193:265-275; Watterberg K L, et al. Secretory leukocyte protease inhibitor and lung inflammation in developing bronchopulmonary dysplasia. *J Pediatr* 1994; 125:264-269). NE is a potent serine proteinase, responsible for tissue destruction in the adult lung with emphysema (Shapiro S D, et al. Neutrophil elastase contributes to cigarette smoke-induced emphysema in mice. *Am J Pathol* 2003; 163:2329-2335). In the preterm newborn lung, increased NE activity affects lung remodeling and increases alveolar epithelial apoptosis and the development of BPD (Watterberg K L, et al. Secretory leukocyte protease inhibitor and lung inflammation in developing bronchopulmonary dysplasia. *J Pediatr* 1994; 125:264-269; Yasumatsu R, et al. SERPINB1 upregulation is associated with in vivo complex formation with neutrophil elastase and cathepsin G in a baboon model of bronchopulmonary dysplasia. *Am J Physiol Lung Cell Mol Physiol* 2006; 291:L619-L627). NE activity was assessed by a spectrophotometric assay using a chromogenic substrate specific for NE, N-methoxy-succinyl-Ala-Ala-Pro-Val pNA (Yasumatsu R, et al. SERPINB1 upregulation is associated with in vivo complex formation with neutrophil elastase and cathepsin G in a baboon model of bronchopulmonary dysplasia. *Am J Physiol Lung Cell Mol Physiol* 2006; 291:L619-L627).

Sequences of primers for quantitative reverse transcriptase-polymerase chain reaction were: IL-8: 5'-TGGC-CAGGATTCACGAGTTC (SEQ ID NO:7) and 5'-TCTGT-GAGGTAGAAAGATGACTGAGATATT (SEQ ID NO:8); IL-6: 5'-GGAGGAAAAAGATGGATGCTTCCAA (SEQ ID NO:9) and 5'-CAGCAGTGGTTTTGATCAAGCAA (SEQ ID NO:10); IL-1β: 5'-GGCTCTCCACCTCCTCTCA (SEQ ID NO:11) and 5'-AGCTCATGCAGAACACCTT (SEQ ID NO:12); tumor necrosis factor (TNF)-α: 5'-GCCGGAATAC-CTGGACTATGC (SEQ ID NO:13) and 5'-CAGGGCGAT-GATCCCAAAGTAG (SEQ ID NO:14); keratinocyte-derived chemokine (KC): 5'-TGCCAGTGCCTGCAGAC (SEQ ID NO:15) and 5'-AGTGGCTATGACTTCGGTTTGG (SEQ ID NO:16); monocyte chemotactic protein 1 (MCP1): 5'-CCCCGACTATCTGTTTCCACAAC (SEQ ID NO:17) and 5'-CCTGGAAGGGCTTCTGATCTG (SEQ ID NO:18); and ovine ribosomal protein L32 5'-GCAGAAGAT-TCAAGGGCCAGATC (SEQ ID NO:19) and 5'-GGTTTTCTTGTTGCTCCCGTAAC (SEQ ID NO:20).

Lung tissue of the right middle lobe was homogenized in 0.9% NaCl and supernatant after centrifugation at 1,000×g for 15 minutes and frozen for ELISA of proinflammatory cytokine proteins (Kramer B W, et al. Surfactant protein A recruits neutrophils into the lungs of ventilated preterm lambs. *Am J Respir Crit Care Med* 2001; 163:158-165; Ikegami M, et al. Intratracheal recombinant surfactant protein D prevents endotoxin shock in the newborn preterm lamb. *Am J Respir Crit Care Med* 2006; 173:1342-1347). BALF was recovered from the left lung (Ikegami M, et al. Whitsett J A. Intratracheal recombinant surfactant protein D prevents endotoxin shock in the newborn preterm lamb. *Am J Respir Crit Care Med* 2006; 173:1342-1347) for further analyses. Total proteins were analyzed (Lowry O H, et al. Protein measurement with the Folin phenol reagent. *J Biol Chem* 1951; 193:265-275) in the supernatant of BALF after 10 minutes of centrifugation at 284×g. The right upper lobe was inflation-fixed at 30 cm $H_2O$ for morphology (Ikegami M, et al. Surfactant protein-D regulates the postnatal maturation of pulmonary surfactant lipid pool sizes. *J Appl Physiol* 2009; 106:1545-1552). The amount of rhSP-D in aliquots of BALF was analyzed by ELISA (Ikegami M, et al. Whitsett JA. Intratracheal recombinant surfactant protein D prevents endotoxin shock in the newborn preterm lamb. *Am J Respir Crit Care Med* 2006; 173:1342-1347).

Results are given as means±SEM. Comparisons between +rhSP-D and control groups were made with two-tailed unpaired t tests. For multiple groups, one-way analysis of variance (ANOVA) followed by Bonferroni-Dunn test, or two-way repeated measures ANOVA were used. Significance was accepted at a P value <0.05.

Example 36

Lung Function Following rhSP-D Treatment

Figure 32:
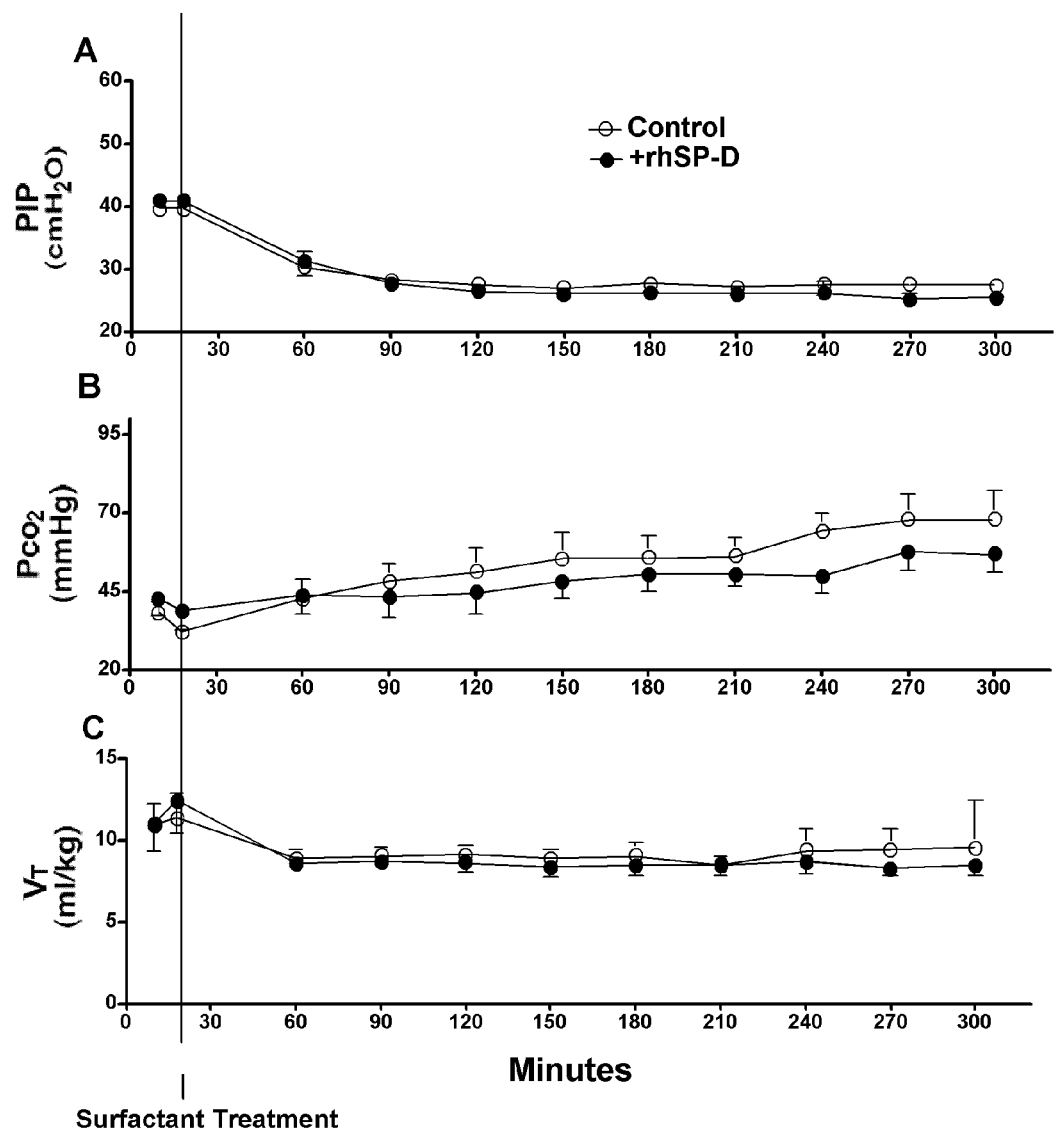
FIG. 32. Treatment with recombinant human surfactant protein D (rhSP-D) does not alter lung physiology in premature lambs. Premature newborn lambs were resuscitated after birth by ventilation with a peak inspiratory pressure (PIP) of $H_2O$, resulting in a mean $P_{CO_2}$ of 40 mm Hg (B) and a mean $V_T$ of 11 ml/kg (C) for rhSP-D treated lambs and controls. Surfactant was given at 20 minutes of age and ventilation was changed to regulate $V_T$ at 8 to 9 ml/kg (C), requiring a mean PIP of 27 cm $H_2O$ (A) for rhSP-D treated lambs and controls.

Six control and six rhSP-D-treated lambs were studied. Sex (three male and three female per group), cord blood pH (7.36±0.04 [control], 7.36±0.05 [+SP-D]), body weight (3.0±0.3 [control], 3.0±0.1 kg [+SP-D]), and lung weight (116±15 [control], 115±5 g [+SP-D]) were similar between +rhSP-D and control groups. Blood pressure, heart rate, hematocrit, glucose, sodium, potassium, and calcium in the blood samples were recorded every 30 minutes and were normal throughout the study period (data not shown). Rectal temperature was maintained at the normal body temperature for sheep (38.5° C.) by means of heating pads, radiant heat, and plastic bodycovering wrap. Ventilation was regulated well for both groups. Lambs were resuscitated with PIP 40 cm $H_2O$ for 20 minutes after birth (FIG. 32A), which resulted in mean $Pco_2$ of 40 mm Hg (FIG. 32B) and $V_T$ of 11 ml/kg (FIG. 32C) for both groups. After surfactant treatment was given at 20 minutes of age, ventilation was changed to regulate $V_T$ at 8 to 9 ml/kg (FIG. 32C) and required a mean PIP of 27 cm $H_2O$ (FIG. 32A) for both groups. These results indicate that lung immaturity, as well as ventilatory stress used to support premature lambs, were comparable between the groups.

Figure 33:
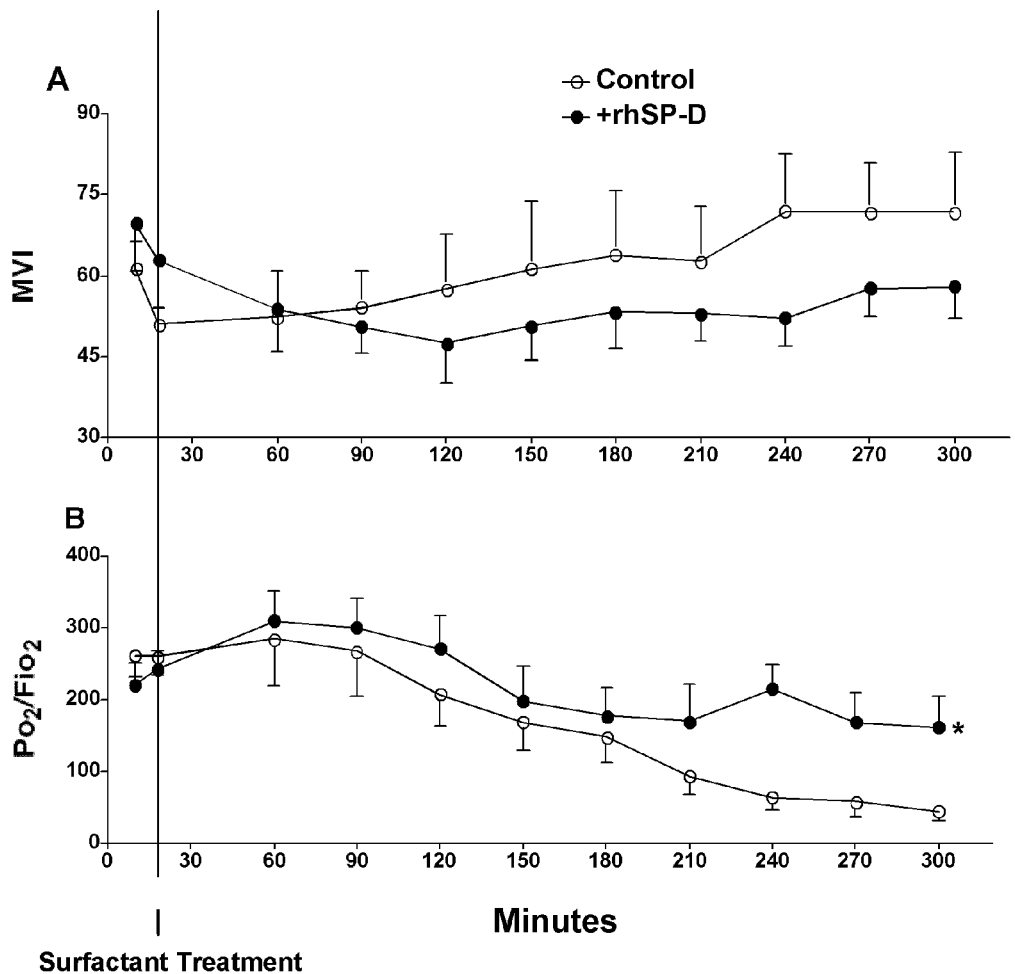
FIG. 33. Effects of rhSP-D treatment on lung function. (A) The modified ventilation index (MVI) was calculated as peak inspiratory pressure×$P_{CO_2}$×respiratory rate/1,000. Although not significant, MVI tends to be better (lower) for the group treated with rhSP-D (+rhSP-D) at later times. (B) $Po_2/Fio_2$ was higher in the +rhSP-D group compared with the control group (*P<0.01 by two-way repeated measures analysis of variance (ANOVA) (overall comparison of control versus +rhSP-D group)). $Po_2/Fio_2$ was significantly decreased after 210 minutes in the control group (P<0.05 vs. 18 min by one-way ANOVA).

A modified ventilation index was calculated as PIP×$Pco_2$× respiratory rate/1,000 (Norden M A, et al. Predictors of survival for infants with congenital diaphragmatic hernia. *J Pediatr Surg* 1994; 29:1442-1446). Although it did not reach statistical significance, the mean modified ventilation index was better for the +rhSP-D group after 240 minutes (FIG. 33A). High $Fi_{O2}$ (0.75-1.0) was used for both groups to maintain $Po_2$ at the target. Premature lambs at this GA have patent ductus arteriosis, and $P_{O2}/Fi_{O2}$ may not be directly associated with lung function. Nevertheless, $P_{O2}/Fi_{O2}$ was higher in the +rhSP-D group than the control group (P<0.01 by two-way repeated measures ANOVA) (FIG. 33B). $Po_2/Fio_2$ was significantly decreased after 210 minutes (P<0.05 by one-way ANOVA) in the control group.

Figure 34:
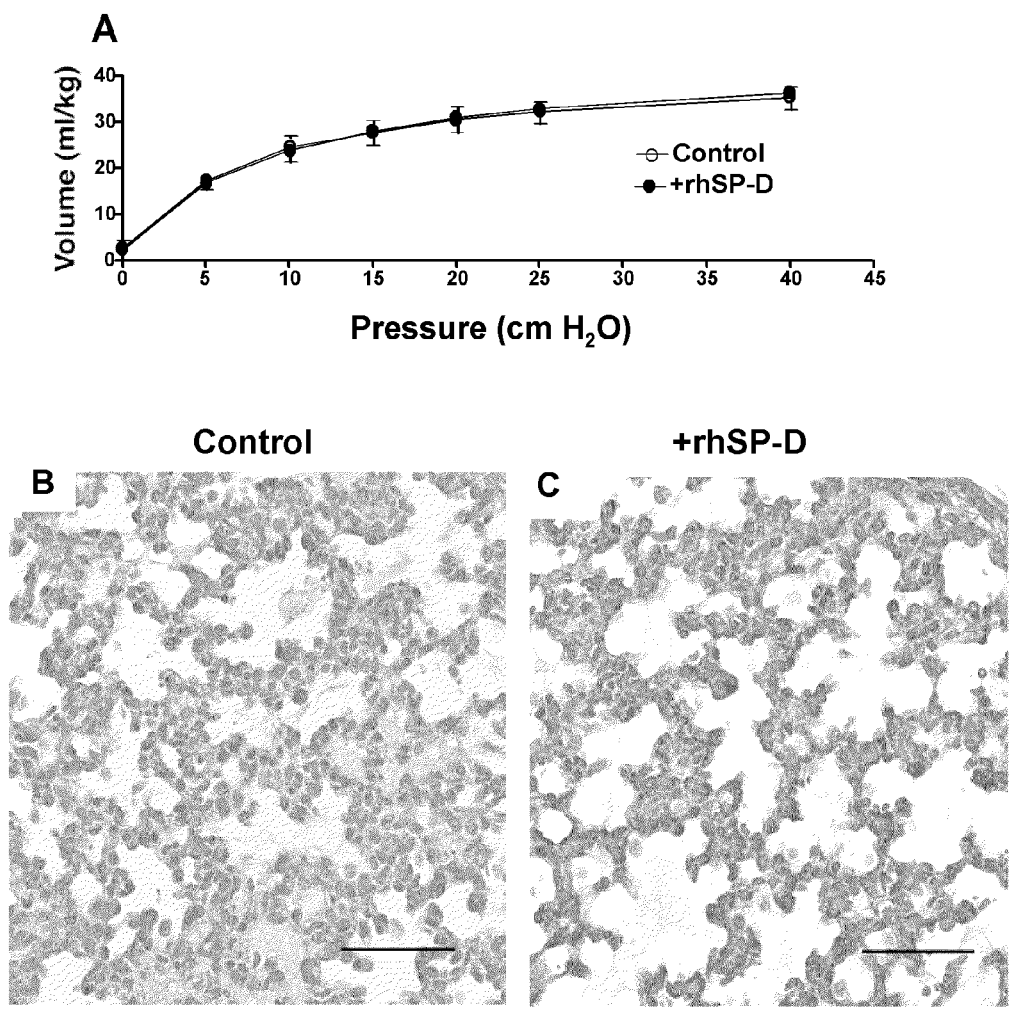
FIG. 34. Treatment with rhSP-D does not alter pressure-volume curves or lung histology in premature lambs. (A) The deflation limbs of pressure-volume curves were not different between the rhSP-D treated lambs and controls. (B, C) Lung histology assessed after staining with hematoxylin and eosin was similar for both groups. Histology was typical of immature lung, including thickened alveolar septal walls and patchy atelectasis. More alveolar fluid was observed in control lambs than in lambs treated with rhSP-D (+rhSP-D). Scale bar: 100 μm.

The deflation limb of pressure-volume curves was not different between the groups (FIG. 34A). Likewise, lung morphology was similar for both groups, with typical findings consistent with immaturity, including thickened alveolar septal walls and patchy atelectasis. More fluid was noted in alveoli of the control lambs compared with the +rhSP-D lambs (FIGS. 34B and 34C).

Example 37

Pulmonary Inflammation Following rhSP-D Treatment

Previous studies indicated a lack of inflammation as detected in BALF and lung tissue from 130-day GA lambs killed at delivery without ventilation (Naik A S, et al. Effects of ventilation with different positive end-expiratory pressures on cytokine expression in the preterm lamb lung. *Am J Respir Crit Care Med* 2001; 164:494-498; Ikegami M, Jobe A. Postnatal lung inflammation increased by ventilation of pre term lambs exposed antenatally to *E. coli* endotoxin. *Pediatr Res* 2002; 52:356-362).

Figure 35:
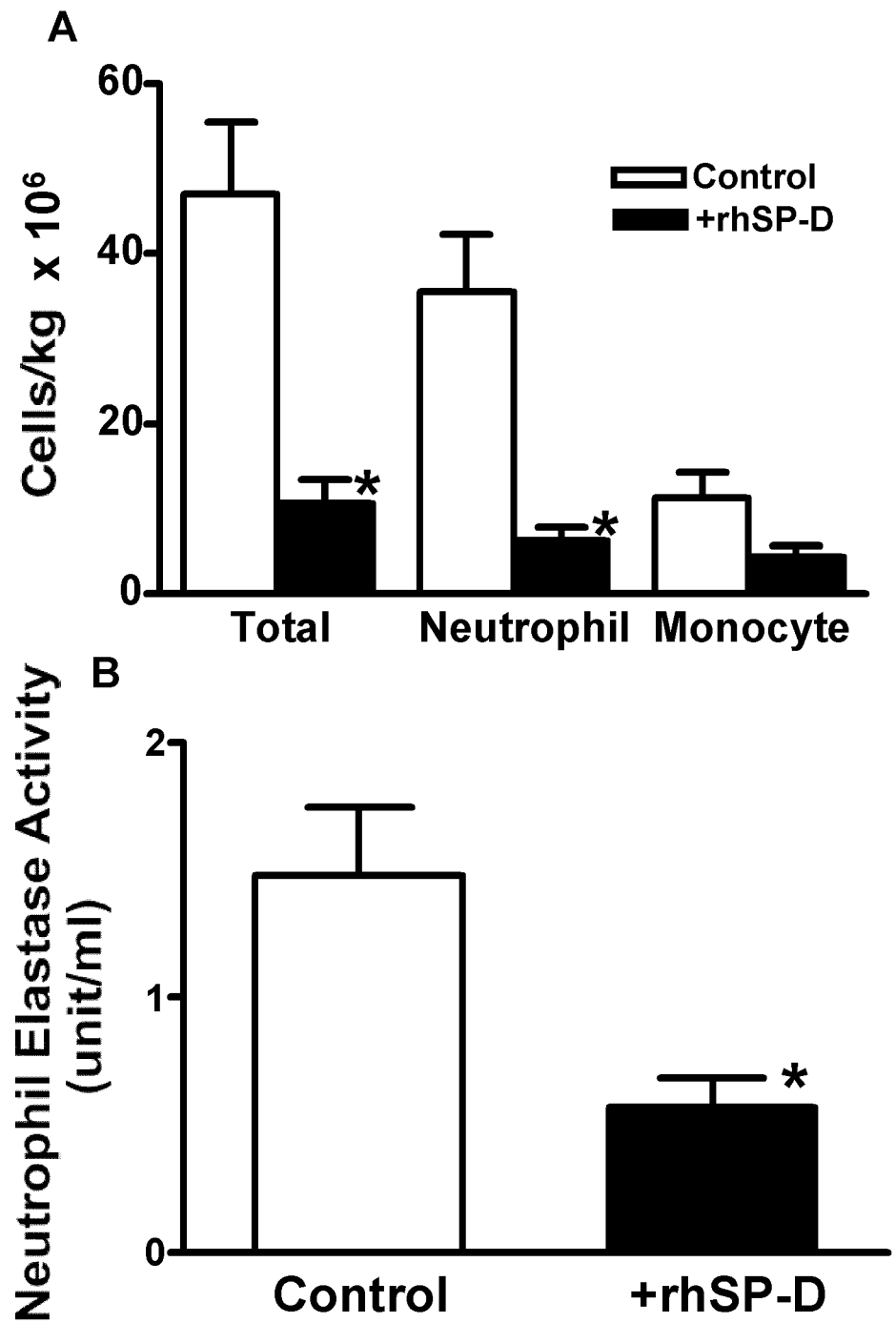
FIG. 35. Treatment with rhSP-D decreases the number of inflammatory cells in BALF and decreases neutrophil elastase (NE) activity. (A) Increased total inflammatory cells and neutrophils in BALF induced by ventilation were suppressed by rhSP-D. (B) NE activity was assessed by a spectrophotometric assay using a chromogenic substrate specific for NE. Treatment with rhSP-D-containing SURVANTA® decreased NE activity (*P<0.05 versus the control group).
Figure 36:
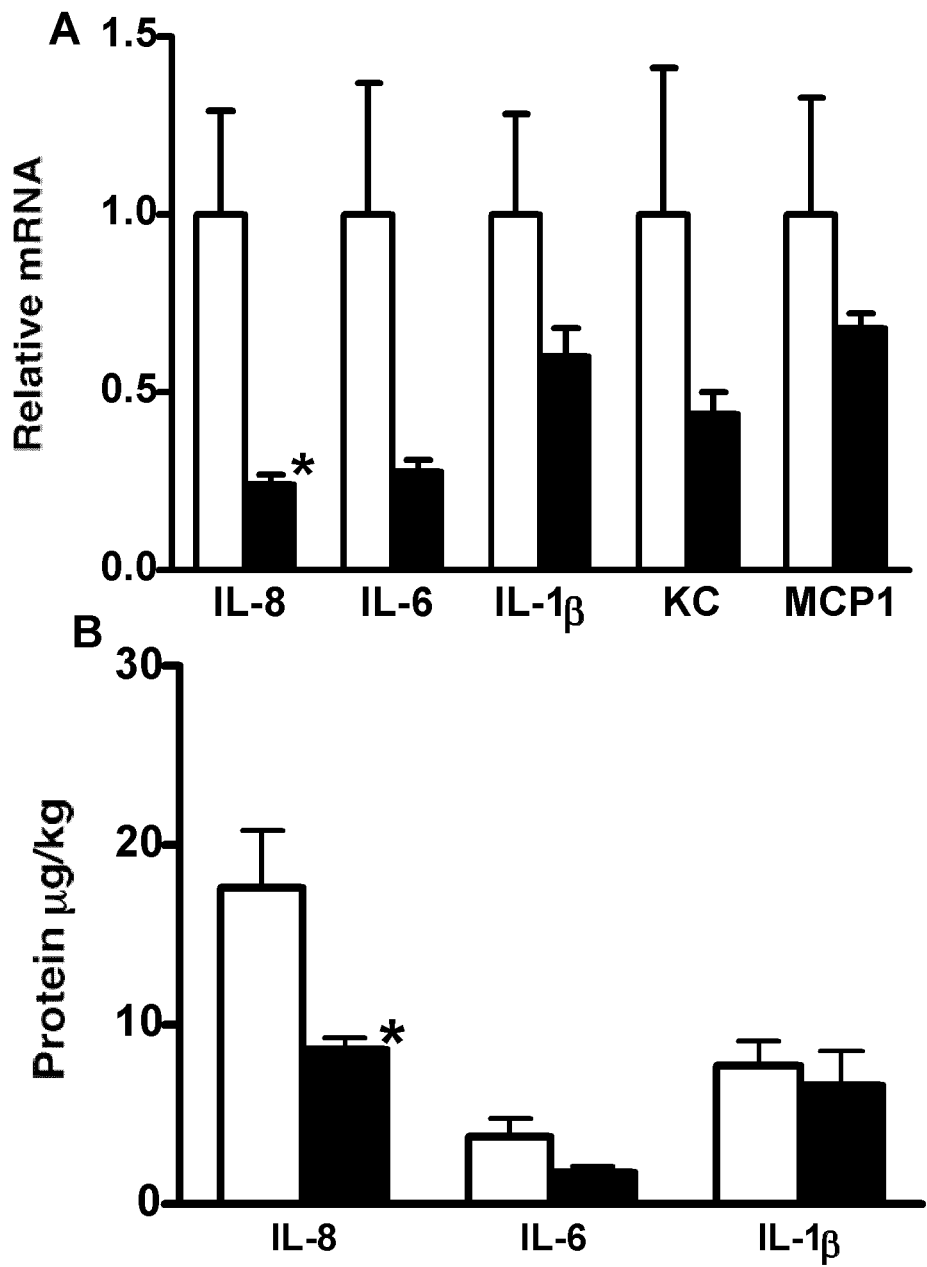
FIG. 36. Treatment with rhSP-D decreases the number of proinflammatory markers in lung homogenates. (A) Increased expression of interleukin-8 (IL-8) mRNA was significantly suppressed by rhSP-D treatment. Although not significant (due to the large variation in the control group), mean values of interleukin-6 (IL-6), interleukin-1β (IL-1β), keratinocyte-derived chemokine (KC), and monocyte chemotactic protein 1 (MCP1) were generally lower in the +rhSP-D group. (B) IL-8 protein in lung homogenates was significantly decreased by rhSP-D treatment (*P<0.05 versus the control group), while IL-1β was not influenced by rhSP-D treatment.

Despite the use of a lung-protective ventilatory strategy, five hours of ventilation was associated with lung inflammation in the control lambs. In contrast, lung inflammation was decreased in all the lambs treated with rhSP-D. Inflammatory cells in the pellets collected by centrifugation were counted using trypan blue and differential cell counts were performed on the stained cytospin preparation (Kramer B W, et al. Surfactant protein A recruits neutrophils into the lungs of ventilated preterm lambs. *Am J Respir Crit Care Med* 2001; 163: 158-165; Naik A S, et al. Effects of ventilation with different positive end-expiratory pressures on cytokine expression in the preterm lamb lung. *Am J Respir Crit Care Med* 2001; 164:494-498). Total inflammatory cell numbers and neutrophils were significantly decreased by rhSP-D (FIG. 35A). Increased NE activity has been associated with the development of BPD (Watterberg K L, et al. Secretory leukocyte protease inhibitor and lung inflammation in developing bronchopulmonary dysplasia. *J Pediatr* 1994; 125:264-269; Yasumatsu R, et al. SERPINB1 upregulation is associated with in vivo complex formation with neutrophil elastase and cathepsin G in a baboon model of bronchopulmonary dysplasia. *Am J Physiol Lung Cell Mol Physiol* 2006; 291:L619-L627). The addition of rhSP-D to SURVANTA® decreased NE activity in the lung (FIG. 35B). Expression of IL-8, IL-6, IL-1β, TNF-α, KC, and MCP1 mRNA were analyzed by reverse transcriptase-polymerase chain reaction (FIG. 36A), and IL-8, IL-6, and IL-1β proteins in the supernatants of lung homogenates were measured by ELISA (FIG. 36B). Ovine ribosomal protein L32 was used as a reference RNA. Proinflammatory cytokine IL-8 (mRNA and protein), which plays a major role in neutrophil recruitment, was significantly decreased in the lung of rhSP-D-treated lambs. Although not statistically significant, mean IL-6 mRNA expression (P=0.06), and IL-6 protein (P=0.1) in the lung were lower in the +rhSP-D group. IL-1β protein and mRNA were not significantly influenced by rhSP-D treatment. Expression of TNF-α mRNA was similarly present at low levels in both groups (data not shown). KC, a functional homolog of IL-8, is critical for neutrophil recruitment and known to increase in ventilation-induced lung injury in adults (Belperio J A, et al. Critical role for CXCR2 and CXCR2 ligands during the pathogenesis of ventilator-induced lung injury. *J Clin Invest* 2002; 110:1703-1716). MCP1 possesses potent chemotactic activity for monocytes. Because of the large variation in lung inflammation in the control lambs, KC and MCP1 mRNA in the lung were not significantly different between the two groups, although mean levels were decreased by rhSP-D treatment.

The CD45 antibody recognizes the leukocyte common antigen and is present on cells of hematopoietic origin, except for erythroid cells and platelets. CD45-positive cells were isolated from BALF using magnetic cell separation (Miltenyi Biotech Inc., Auburn, Calif.) and CD14, CD11b, and CD44 were analyzed by flow cytometry (data not shown). CD14-positive cells were not detected in either group, suggesting that lung inflammation was not associated with infection. Both CD11b and CD44 influence vascular-to-tissue migration of neutrophils and monocytes to the sites of inflammation (Weirich E, et al. Neutrophil CD11b expression as a diagnostic marker for early-onset neonatal infection. *J Pediatr* 1998; 132:445-451). Treatment with rhSP-D did not influence expression of CD11b or CD44, suggesting that suppression of neutrophil recruitment by rhSP-D in the lung was independent of changes in CD11b and CD44.

After instillation of 7 mg of rhSP-D, 6.7±0.2 mg rhSP-D was recovered in BALF 4.7 hours after treatment. The slow clearance of exogenous rhSP-D from the lung is consistent with previous findings (Ikegami M, Jobe AH. Surfactant metabolism. *Semin Perinatol* 1993; 17:233-240), supporting the low rate of surfactant clearance in the preterm lung. Human SP-D was not detected in BALF from control lambs.

Example 38

Increased Resistance Against Surfactant Inhibition Following rhSP-D Treatment

Surface tension was measured by captive bubble surfactometer (Schoel M, et al. The captive bubble method for the evaluation of pulmonary surfactant: surface tension, area, and volume calculations. *Biochim Biophys Acta* 1994; 1200:281-290) on 3 µL of samples containing 15 µg/µL SURVANTA® and 2% rhSP-D or buffer in the presence or absence of surfactant inhibitor (21 µg/µL plasma protein) (Ikegami M, et al. Characteristics of surfactant from SP-A deficient mice. *Am J Physiol Lung Cell Mol Physiol* 1998; 275:L247-L25). This amount of plasma protein relative to SURVANTA® was 30% lower than the concentration that is known to inhibit the activity of SURVANTA® in the ventilated premature newborn lamb lung in vivo (Wada K, et al. Tidal volume effects on surfactant treatment responses with the initiation of ventilation in preterm lambs. *J Appl Physiol* 1997; 83:1054-1061). The influence of rhSP-D on the ultrastructure of SURVANTA® was studied as previously described (Schmiedl A, et al. Influence of plasma and inflammatory proteins on the ultrastructure of exogenous surfactant. *J Electron Microsc (Tokyo)* 2004; 53:407-416).

Figure 37:
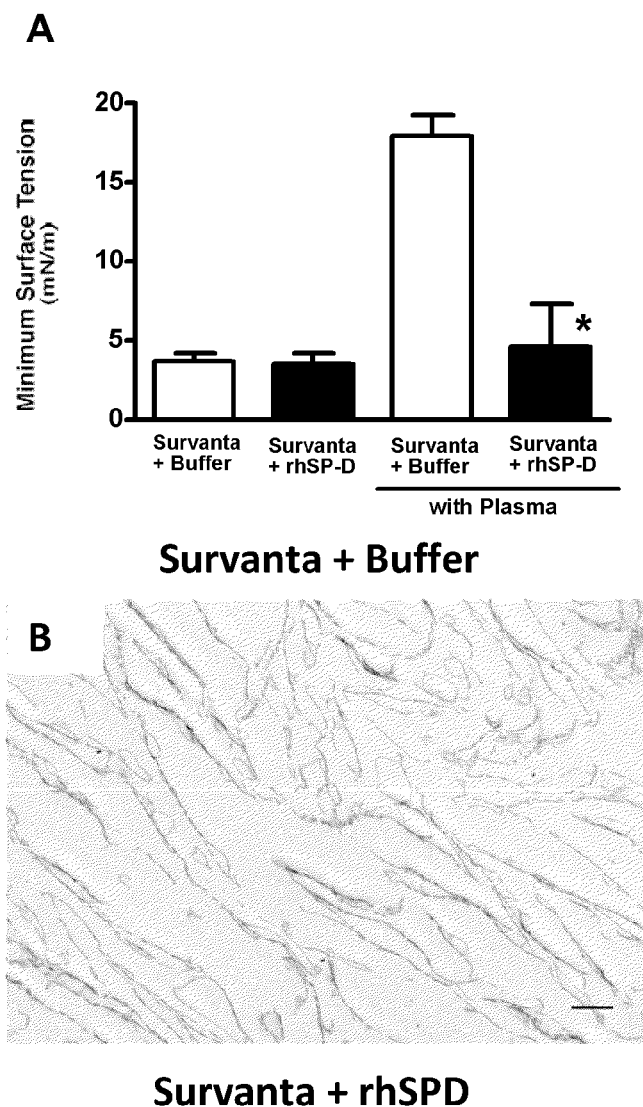
FIG. 37. Addition of rhSP-D to surfactant increased resistance against surfactant inhibition. (A) Surface tension was measured by a captive bubble surfactometer. SURVANTA®+buffer had high surface activity, and minimum surface tension was low and was not influenced by addition of rhSP-D. Plasma protein inhibited the surface tension-lowering properties of SURVANTA®, and minimum surface tension was increased. The addition of rhSP-D rendered the SURVANTA® more resistant to plasma protein inhibition, with low minimum surface tension in the presence of plasma protein (n=3, *P<0.05 versus SURVANTA®+buffer with plasma). (B, C) Representative electron micrographs of SURVANTA® mixed with buffer or rhSP-D. Addition of rhSP-D changed the ultrastructure of SURVANTA® from simple lipid layers to the mixture of multiple lipid layers and lipid aggregates (n=3 per group). Scale bar: 500 nm.

Minimum surface tension of SURVANTA® with (+rhSP-D) or without rhSP-D (+buffer) in the presence or absence of a surfactant inhibitor (plasma protein) was measured with a captive bubble surfactometer (FIG. 37A). The minimum surface tension was low with or without rhSP-D—consistent with the high surface activity of SURVANTA® and similarity of lung function and pressure-volume curves seen in both +rhSP-D-treated and control lambs. Immediately after mixing with plasma, surfactant mixtures were applied to the bubble. Plasma proteins inhibited the surface tension-lowering properties of SURVANTA®, with the minimum surface tension being increased to greater than 15 mN/m. The addition of 2% rhSP-D to SURVANTA® rendered the SURVANTA® more resistant to plasma protein inhibition, the minimum surface tension remaining low in the presence of plasma proteins. Because SP-D influences surfactant ultrastructure in the alveolus by causing lysis of surfactant lipid layers (Ikegami M, et al. Surfactant protein-D regulates the postnatal maturation of pulmonary surfactant lipid pool sizes. *J Appl Physiol* 2009; 106:1545-1552), ultrastructure of the surfactant mixtures used for treatment was assessed. The simple lipid layers formed by SURVANTA® (FIG. 37B) were changed by the addition of rhSP-D, causing the formation of lipid aggregates and multilayers (FIG. 37C). These changes in the ultrastructure of SURVANTA® caused by rhSP-D may be related to its resistance to inhibition of surface activity by plasma protein. Although proteins in BALF in both the control group (60±7 mg/kg) and +rhSP-D group (57±11 mg/kg) were threefold higher than that in non-ventilated premature lambs seen in previous studies (Naik A S, et al.

Effects of ventilation with different positive end-expiratory pressures on cytokine expression in the preterm lamb lung. *Am J Respir Crit Care Med* 2001; 164:494-498; Ikegami M, Jobe A. Postnatal lung inflammation increased by ventilation of preterm lambs exposed antenatally to *E. coli* endotoxin. *Pediatr Res* 2002; 52:356-362), they were not high enough to inhibit the function of the large amount of SURVANTA® given to the lambs. Inhibition of surfactant function by plasma protein occurs when alveolar proteins are increased above 200 mg/kg (Wada K, et al. Tidal volume effects on surfactant treatment responses with the initiation of ventilation in preterm lambs. *J Appl Physiol* 1997; 83:1054-1061).

Example 39 rhSP-D and Animal Surfactant Treatment in a Premature Infant rhSP-D and natural animal surfactants, including SURVANTA®, INFASURF®, and CUROSURF®, are administered to premature infants. The combinations of rhSP-D and each of the natural animal surfactants are tested clinically against the natural surfactants alone (i.e., a test for superior effects). The premature infants are assessed clinically for the prevention and/or treatment of neonatal respiratory distress syndrome (RDS), and for the prevention of bronchopulmonary dysplasia (as these conditions are defined by one of skill in the art at the time of the study). Study endpoints include the percentage of infants recovering from RDS and the incidence of BPD in the study population.

Example 40 rhSP-D and Synthetic Surfactant Treatment in a Premature Infant rhSP-D and a synthetic surfactant, with or without any component of surfactant protein, are administered to premature infants. The combination of rhSP-D and the synthetic surfactant is tested clinically against the synthetic surfactant alone (i.e., a test for superiority), and/or a natural surfactant alone (i.e., a test for superiority), and/or the combination of rhSP-D and a natural surfactant (i.e., a test for equivalence or superiority). The premature infants are assessed clinically for the prevention and/or treatment of neonatal respiratory distress syndrome (RDS), and for the prevention of bronchopulmonary dysplasia (as these conditions are defined by one of skill in the art at the time of the study). Study endpoints include the percentage of infants recovering from RDS and the incidence of BPD in the study population.

What is claimed is:

1. A method for treating in a patient at risk of developing bronchopulmonary dysplasia (BPD), comprising:
   identifying a patient at risk for developing BPD;
   administering recombinant human surfactant protein D (rhSP-D) and a surfactant formulation in the absence of surfactant protein A (SP-A) to the patient in need thereof, in an amount effective to reduce the risk of developing BPD.

2. The method of claim 1, wherein the rhSP-D and the surfactant formulation are administered simultaneously.

3. The method of claim 1, wherein the rhSP-D and the surfactant formulation are administered in an aerosol of an aqueous solution.

4. The method of claim 3, wherein the solution comprises a buffer, sodium chloride, and ethylenediaminetetraacetic acid.

5. The method of claim 1, wherein the surfactant formulation comprises at least one phospholipid.

6. The method of claim 1, wherein the surfactant formulation comprises at least one protein selected from the group consisting of surfactant protein B (SP-B), and surfactant protein C (SP-C).

7. The method of claim 1, wherein the surfactant formulation comprises a synthetic surfactant protein.

8. The method of claim 1, wherein the dosage of the rhSP-D is about 0.1 mg to about 10 mg per kg body weight.

9. The method of claim 8, wherein the dosage of the rhSP-D is about 1 mg to about 2 mg per kg body weight.

10. The method of claim 1, wherein the patient is a neonate.

11. A method for reducing the risk of developing bronchopulmonary dysplasia (BPD) in a mammal, comprising:
    administering recombinant human SP-D (rhSP-D) and a surfactant formulation in the absence of surfactant protein A (SP-A) to a mammal in need thereof, in an amount effective to reduce the risk of developing BPD in the mammal.

12. The method of claim 11, wherein the rhSP-D and the surfactant formulation are administered simultaneously.

13. The method of claim 11, wherein the rhSP-D and the surfactant formulation are administered in an aerosol of an aqueous solution.

14. The method of claim 13, wherein the solution comprises a buffer, sodium chloride, and ethylenediaminetetraacetic acid.

15. The method of claim 12, wherein the surfactant formulation comprises at least one phospholipid.

16. The method of claim 11, wherein the BPD is associated with injury from mechanical ventilation.

17. The method of claim 11, wherein the surfactant formulation further comprises at least one protein selected from the group consisting of surfactant protein B (SP-B), and surfactant protein C (SP-C).

18. The method of claim 11, wherein the surfactant formulation further comprises a synthetic surfactant protein.

19. The method of claim 11, wherein the dosage of the rhSP-D is about 0.1 mg to about 10 mg per kg body weight.

20. The method of claim 19, wherein the dosage of the rhSP-D is about 1 mg to about 2 mg per kg body weight.

21. The method of claim 11, wherein the mammal is an infant.

\* \* \* \* \*

SEQUENCE LISTING

```
<160> NUMBER OF SEQ ID NOS: 20

<210> SEQ ID NO 1
<211> LENGTH: 25
<212> TYPE: DNA
<213> ORGANISM: Mus musculus

<400> SEQUENCE: 1
tctgcgggtt ctctgcgtcc tgtgc                                              25

<210> SEQ ID NO 2
<211> LENGTH: 25
<212> TYPE: DNA
<213> ORGANISM: Mus musculus

<400> SEQUENCE: 2
gtgccctgga agcggaacgg aaact                                              25

<210> SEQ ID NO 3
<211> LENGTH: 21
<212> TYPE: DNA
<213> ORGANISM: Mus musculus

<400> SEQUENCE: 3
ttctctggac gtcaaatgtg g                                                  21

<210> SEQ ID NO 4
<211> LENGTH: 24
<212> TYPE: DNA
<213> ORGANISM: Mus musculus
```

```
<400> SEQUENCE: 4
caaagaagga gccctagttc aagg                                              24

<210> SEQ ID NO 5
<211> LENGTH: 21
<212> TYPE: DNA
<213> ORGANISM: Mus musculus

<400> SEQUENCE: 5
gtgggccgct ctaggcacca a                                                 21

<210> SEQ ID NO 6
<211> LENGTH: 24
<212> TYPE: DNA
<213> ORGANISM: Mus musculus

<400> SEQUENCE: 6
ctctttgatg tcacgcagga tttc                                              24

<210> SEQ ID NO 7
<211> LENGTH: 20
<212> TYPE: DNA
<213> ORGANISM: Homo sapiens

<400> SEQUENCE: 7
tggccaggat tcacgagttc                                                   20

<210> SEQ ID NO 8
<211> LENGTH: 30
<212> TYPE: DNA
<213> ORGANISM: Homo sapiens

<400> SEQUENCE: 8
tctgtgaggt agaaagatga ctgagatatt                                        30

<210> SEQ ID NO 9
<211> LENGTH: 25
<212> TYPE: DNA
<213> ORGANISM: Homo sapiens

<400> SEQUENCE: 9
ggaggaaaaa gatggatgct tccaa                                             25

<210> SEQ ID NO 10
<211> LENGTH: 23
<212> TYPE: DNA
<213> ORGANISM: Homo sapiens

<400> SEQUENCE: 10
cagcagtggt tttgatcaag caa                                               23

<210> SEQ ID NO 11
<211> LENGTH: 19
<212> TYPE: DNA
<213> ORGANISM: Homo sapiens

<400> SEQUENCE: 11
ggctctccac ctcctctca                                                    19

<210> SEQ ID NO 12
<211> LENGTH: 19
<212> TYPE: DNA
<213> ORGANISM: Homo sapiens
```

```
<400> SEQUENCE: 12
agctcatgca gaacacctt                                              19

<210> SEQ ID NO 13
<211> LENGTH: 21
<212> TYPE: DNA
<213> ORGANISM: Homo sapiens

<400> SEQUENCE: 13
gccggaatac ctggactatg c                                           21

<210> SEQ ID NO 14
<211> LENGTH: 22
<212> TYPE: DNA
<213> ORGANISM: Homo sapiens

<400> SEQUENCE: 14
cagggcgatg atcccaaagt ag                                          22

<210> SEQ ID NO 15
<211> LENGTH: 17
<212> TYPE: DNA
<213> ORGANISM: Homo sapiens

<400> SEQUENCE: 15
tgccagtgcc tgcagac                                                17

<210> SEQ ID NO 16
<211> LENGTH: 22
<212> TYPE: DNA
<213> ORGANISM: Homo sapiens

<400> SEQUENCE: 16
agtggctatg acttcggttt gg                                          22

<210> SEQ ID NO 17
<211> LENGTH: 23
<212> TYPE: DNA
<213> ORGANISM: Homo sapiens

<400> SEQUENCE: 17
ccccgactat ctgtttccac aac                                         23

<210> SEQ ID NO 18
<211> LENGTH: 21
<212> TYPE: DNA
<213> ORGANISM: Homo sapiens

<400> SEQUENCE: 18
cctggaaggg cttctgatct g                                           21

<210> SEQ ID NO 19
<211> LENGTH: 23
<212> TYPE: DNA
<213> ORGANISM: Homo sapiens

<400> SEQUENCE: 19
gcagaagatt caagggccag atc                                         23

<210> SEQ ID NO 20
<211> LENGTH: 23
<212> TYPE: DNA
```

```
<213> ORGANISM: Homo sapiens

<400> SEQUENCE: 20
ggttttcttg ttgctcccgt aac                                                    23
```